US008227484B2

(12) United States Patent
Yakatan et al.

(10) Patent No.: US 8,227,484 B2
(45) Date of Patent: *Jul. 24, 2012

(54) PHARMACEUTICAL COMPOSITIONS COMPRISING DEXTROMETHORPHAN AND QUINIDINE FOR THE TREATMENT OF NEUROLOGICAL DISORDERS

(75) Inventors: Gerald Yakatan, Del Mar, CA (US); James Berg, San Diego, CA (US); Laura Pope, Carlsbad, CA (US); Richard Alan Smith, La Jolla, CA (US)

(73) Assignee: Avanir Pharmaceuticals, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/415,067

(22) Filed: Mar. 8, 2012

(65) Prior Publication Data

US 2012/0165363 A1 Jun. 28, 2012

Related U.S. Application Data

(63) Continuation of application No. 12/699,408, filed on Feb. 3, 2010, which is a continuation of application No. 11/035,213, filed on Jan. 12, 2005, now Pat. No. 7,659,282, which is a continuation of application No. PCT/US03/22303, filed on Jul. 17, 2003.

(60) Provisional application No. 60/396,661, filed on Jul. 17, 2002.

(51) Int. Cl.

| | |
|---|---|
| ***A01N 43/90*** | (2006.01) |
| ***A01N 43/42*** | (2006.01) |
| ***A61K 31/44*** | (2006.01) |

(52) U.S. Cl. ........................................ 514/289; 514/305

(58) Field of Classification Search .................. 514/289, 514/305

See application file for complete search history.

(56) References Cited

U.S. PATENT DOCUMENTS

| | | | | |
|---|---|---|---|---|
| 3,536,809 | A | 10/1970 | Appelzweig | |
| 3,598,123 | A | 8/1971 | Zaffaroni | |
| 3,845,770 | A | 11/1974 | Theeuwes et al. | |
| 3,916,899 | A | 11/1975 | Theeuwes et al. | |
| 4,008,719 | A | 2/1977 | Theeuwes et al. | |
| 4,316,888 | A | 2/1982 | Nelson | |
| 4,806,543 | A | 2/1989 | Choi | |
| 5,034,400 | A | 7/1991 | Olney | |
| 5,166,207 | A | 11/1992 | Smith | |
| 5,206,248 | A | 4/1993 | Smith | |
| 5,321,012 | A | 6/1994 | Mayer et al. | |
| 5,350,756 | A | 9/1994 | Smith | |
| 5,352,683 | A | 10/1994 | Mayer et al. | |
| 5,366,980 | A | 11/1994 | Smith | |
| 5,502,058 | A | 3/1996 | Mayer et al. | |
| 5,556,838 | A | 9/1996 | Mayer et al. | |
| 5,863,927 | A | 1/1999 | Smith et al. | |
| 6,207,674 | B1 | 3/2001 | Smith | |
| 7,659,282 | B2 * | 2/2010 | Yakatan et al. | 514/289 |
| 2002/0068718 | A1 | 6/2002 | Pierce | |
| 2004/0087479 | A1 | 5/2004 | Sosnowski et al. | |

FOREIGN PATENT DOCUMENTS

| | | |
|---|---|---|
| WO | WO 96/09044 | 3/1996 |
| WO | WO 00/17366 | 3/2000 |
| WO | WO 00/59486 | 10/2000 |

OTHER PUBLICATIONS

U.S. Appl. No. 12/699,408, filed Feb. 2010, Yakatan et al.*

Abdel-Rahman et al., "Potent Inhibition of Cytochrome P-450 2D6-Mediated Dextromethorphan *O*-Demethylation by Terbinafine," Drug Metab. Dispos. , Jul. 1999; 27(7); 770-775.

Abdul et al., "The antitussive effect of dextromethorphan in relation to CYP2D6 activity," Br. J. Clin. Pharmacol. , Sep. 1999; 48(3); 382-387.

Albers, G. W., et al., "Safety and tolerance of oral dextromethorphan in patients at risk for brain ischemia," 1991, Stroke, 22,:1075-1077.

Andersen et al., "Citalopram for Post-Stroke Pathological Crying"1993, Lancet, 342, 837-839.

Andersen et al., "Pathoanatomic correlation between poststroke pathological crying and damage to brain areas involved in serotonergic neurotransmission," 1994, Stroke, 25, 1050-1052.

Applebaum, J. S., et al, "Dextromethorphan in the treatment of ALS: A pilot study," Abstract No. 960S (p. 393) in Neurology 41 (Suppl. 1), Mar. 1991.

Askmark et al., "A pilot trial of dextromethorphan in amyotrophic lateral sclerosis," 1993, J. Neurol. Neurosurg. Psychiatry, 56:197-200.

Beck et al., "Internal Consistencies of the Original and Revised Beck Depression Inventory,"1984, J. Clin. Psychol. 40, 1365-1367.

Ben Abraham, et al., "Dextromethorphan for phantom pain attenuation in cancer amputees: a double-blind crossover trial involving three patients", Clin J Pain, (2002) 18: 282-285.

Bensimon, et al., "A controlled trial of Riluzole in amyotrophic lateral sclerosis", N Eng J Med. (1994) 330:585-91.

Bertelsen et al., "Apparent Mechanism-Based Inhibition of Homan CYP2D6 in Vitro by Paroxetine: Comparison with Fluoxetine and Quinidine," Mar. 2003;31(3):289-93.

Bisaga, A., et al, "Opiate withdrawal with dextromethorphan [letter]," Amer. J. Psychiatry 154: 584 (1997).

Blin et al., : "A controlled one-year trial of dextromethorphan in amyotrophic lateral sclerosis,"1996, Clin. Neuropahrmacol. 19; 189-192. Brinn, R., et al, "Sparteine oxidation is practically abolished in quinidine-treated patients," Br. J. Clin. Pharmacol. 22: 194-197, 1986.

Broly, et al. "Effect of quinidine on the dextromethorphan O-demethylase activity of microsomal fractions from human liver", Br J Clin Pharmacol. (1989) 28(1): 29-36.

Broly, et al., "Inhibitory studies of mexiletine and dextromethorphan oxidation in human liver microsomes", Biochem Pharmacol. (1990) 39:1045-1053.

Broly, et al., CA 111: 89742z, 1989.

Broly, et al., CA 112: 210493v, 1990.

Brooks, "Personality change after severe head injury" Acta Neurochirurgica Suppl. (1988) 44: 59-64.

(Continued)

*Primary Examiner* — ShengJun Wang

*Assistant Examiner* — Kara R McMillian

(74) *Attorney, Agent, or Firm* — Kilpatrick, Townsend & Stockton LLP

(57) ABSTRACT

Pharmaceutical compositions and methods for treating neurological disorders by administering same are provided. The compositions comprise dextromethorphan in combination with quinidine.

17 Claims, 5 Drawing Sheets

OTHER PUBLICATIONS

Brosen, K., et al, "Extensive metabolizers of debrisoquin become poor metabolizers during quinidine treatment," Pharmacol. Toxicol. 60: 312-314, 1987.
Capon et al., "The influence of CYP2D6 polymorphism and quinidine on the disposition and antitussive effect of dextromethorphan in humans," Sep. 1996, Clin. Pharmacol. Ther., 60(3), 295-307.
Carpenter et al., "Dextromethorphan and dextrorphan as calcium channel antagonists," Brain Res., Jan. 26, 1988 439(1-2):372-5.
Chase, et al., "Antiparkinsonian and antidyskinetic activity of drugs targeting central glutamatergic mechanisms", J Neurol. (2000) 247 Suppl 2:II36-II42.
Choi D., "Dextrorphan and dextromethorphan attenuate glutamate neurotoxicity," *Brain Res*., 403 (1987) 333-6.
Choi, et al. Dextrorphan and Levorphanol Selectivity Block N-Methyl-d-Aspartate Receptor-Mediated Neurotoxicity on Cortical Neurons, The Journal of Pharmacology and Experimental Therapeutics, vol. 242, No. 2, (1987) pp. 713-720.
Cottrell, et al., "Original Papers: The Affective Symptomatology of Disseminated Sclerosis.: A Study of 100 Cases," J. Neurol. Psychopathol., 1926; 7:1-30.
Craviso, et al., "High-affinity dextromethorphan binding sites in guinea pig brain. I. Initial characterization", Mol Pharmacol., (1983) 23(3):619-628.
Craviso, et al., "High-affinity dextromethorphan binding sites in guinea pig brain. II. Competition experiments", Mol Pharmacol. (1983) 23(3):629-40.
Dark et al., "Pathology Laughing and Crying," Austr. N. Zeal. J. Psychiatry, 1996; 30:472-9.
Dayer, et al. "Dextromethorphan O-demethylation in liver microsomes as a prototype creation to monitor cytochrome P-450 db1 activity", Clin Pharmacol Ther., (1989) 45(1):34-40.
Debonnel et al., "Modulation of NMDA and Dopaminerigic Neutrotransmissions by Sigman Ligands: Possible Implications for the Treatment of Psychiatric Disorders," Life Sci., 1996; 58:721-34.
Dere, et al., "NMDA-recptor antagonism via dextromethorphan and ifenprodil modulates graded anxiety test performance of C57BL/6 mice", Behav. Pharmacol. (2004) 14(3)245-249; Abstract 1 page.
Desmeules, et al., "Contribution of cytochrome P-4502D6 phenotype to the neuromodulatory effects of dextromethorphan", J Pharmacol Exp Ther., (1999) 288(2): 607-612.
Dickenson, A.H., "A cure for wind up: NMDA receptor antagonists as potential analgesics," Trends in Pharm. Sci. 11: 307-309, 1990.
Dickenson, et al., "Dextromethorphan and levorphanol on dorsal horn nociceptive neurones in the rat", Neuropharmacology (1991)30: 1303-1308.
Dickenson, et al., "Evidence for a role of the NMDA receptor in the frequency dependent potentiation of deep rat dorsal horn nociceptive neurons following C fibre stimulation," Neuropharmacology (1987) 26(8): 1235-1238.
Doble, "The pharmacology and mechanism of action of riluzole," Neurology (1996) 47(6 Suppl 4):S233-41.
Droll, et al., "Comparison of three CYP2D6 probe substrates and genotype in Ghanaians, Chinese and Caucasions," Pharmacogenetics (1998) 8(4): 325-333.
Due Nielsen, et al., CA 112: 171691m, 1990.
Feinstein et al., "Prevalence and Neurobehavorial Correlates of Pathological Laughing and Crying in Multiple Sclerosis," Arch. Neurol., 1997; 54:1116-21.
Fernandes et al., "Treatment of codeine dependence with inhibitors of cytochrome P450 2D6," J Clin Psychopharmacol. Jun. 2002;22(3):326-9.
France, et al., "Analgesic effects of phencyclidine-like drugs in rhesus monkeys," J Pharmacol Exp Ther., (1989) 250(1): 197-201.
Frison etal., "Repeated measures in clinical trials: analysis using mean summary statistics and its implications for design," *Stat. Med*., 11 (1992) 1685-704.
Funck-Brentano et al., "Effect of Low Dose Quinidine on Encainide Pharmacokinetics and Pharmacodynamics, Influence of Genetic Polymorphism," J. Pharmacol. Exp. Ther., Apr. 1989, 249(1):134-42.
Funck-Brentano et al., "Genetically-determined interaction between propafenone and low dose quinidine: Role of active metabolites in Modulating net Drug Effect," Br. J. Clin. Pharmacol., Apr. 1989, 27(4):435-44.
Gallagher, J.P., "Pathological Laughter and Crying in ALS: a Search for their Origin," Acta Neurol. Scand. 1989; 80:114-7.
Gorski et al. "Characterization of dextromethorphan N-demethylation by human liver microsomes. Contribution of the cytochrome P450 3A (CYP3A) subfamily," Biochem Pharmacol. Jul. 5, 1994;48(1):173-82.
Gould. 1986, "Salt selection for basic drugs," International Journal of Pharmaceutics, vol. 33, pp. 201-217.
Granvil et al., "4-Hydroxylation of Debrisoquine by Human CYP1A1 and Its Inhibition by Quinidine and Quinine," J Pharmacol Exp Ther. Jun. 2002;301(3):1025-32.
Grass, et al, "N-methyl-D-aspartate receptor antagonists potentiate morphine's antinociceptive effect in the rat", Acta Physiol Scand. (1996) 158(3): 269-73.
Gredal et al., "A Clinical Trial of Dextromethorphan in Amyotrophic Lateral Sclerosis," Acta Neurol. Scand. 1997; 96: 8-13.
Guttendorf, R. J., et al, "Simplified phenotyping with dextromethorphan by thin-layer chromatography," Ther. Drug. Monit. 10: 490-498, 1988.
Guzey et al. "Change from the CYP2D6 extensive metabolizer to the poor metabolizer phenotype during treatment With bupropion," Ther Drug Monit. Jun. 2002;24(3):436-7.
Heiskanen, et al., "Analgesic effects of dextromethorphan and morphine in patients with chronic pain", Pain (2002) 96(3): 261-267.
Hildebrand et al., "Determination of Dextromethorphan Metabolizer Phenotype in Healthy Volunteers," Eur. J. Clin. Pharmacol., 1989; 36:315-318.
Hoffmann, et al, "Dextromethorphan potentiates morphine antinociception, but does not reverse tolerance in rats", Neuroreport (1996) 7(3): 838-40.
Holford et al., "The effect of quinidine and its metabolites on the electrocardiogram and systolic time intervals: concentration—effect relationships," Br. J. Clin. Pharmacol. 11 (1981) 187-95.
Hollander et al., "High-dose Dextromethorphan in Amyotrophic Lateral Sclerosi: Phase I Safety and Pharmacokinetic Studies," Ann. Neurol., 1994; 36:920-4.
Hou et al. "Determination of dextromethorphan metabolic phenotype by salivary analysis with a reference to genotype in Chinese patients receiving renal hemodialysis," Clin Pharmacol Ther. Apr. 1996;59(4):411-7.
House et al., "Emotionalism After Stroke," BMJ, 1989; 298:991-4.
Iannoccone et al., "Pharmacologic Treatment of Emotional Lability," Clin. Neuropharm., 1996; 19:532-5.
Inaba, T., et al, "Quinidine: Potent inhibition of sparteine and debrisoquin oxidation in vivo," Br. J. Clin. Pharmacol. 22: 199-200, 1986.
International Preliminary Examination Report in equivalent PCT International Application No. PCT/US2003/022303.
Jackson et al. "Amyotrophic Lateral Sclerosis," Semin. Neurol. 1998; 18:27-39.
Jerusalem et al., "ALS", Neurology, 1996; 47:S218-20.
Jurima-Romet et al. "Evidence for the catalysis of dextromethorphan O-demethylation by a CYP2D6-like enzyme in pig liver," Toxicol In Vitro. Jun. 2000;14(3):253-63.
Kalin et al, "Opiate modulation of separation-induced distress in non-human primates," Brain Research 440: 285-292, 1988.
Kalin, et al., CA 108: 124860y, 1988.
Kaufer et al. "Validation of the NPI-Q, a brief clinical form of the Neuropsychiatric Inventory," J Neuropsychiatry Clin Neurosci 12 (2000) 233-9.
Kauppila, et al, "Dextromethorphan potentiates the effect of morphine in rats with peripheral neuropathy," Neuroreport (1998) 9(6): 1071-4.
Kerry et al. "The role of CYP2D6 in primary and secondary oxidative metabolism of dextromethorphan: in vitro studies using human liver microsomes," Br J Clin Pharmacol. Sep. 1994;38(3):243-8.
Kim et al., "Metabolism to Dextrorphan is not essential for Dextromethorphan's Anticonvulsant Activity Against Kainate in Mice," Life Sci., 2003; 72: 769-783.

Klein, et al., "The effect of prototypic sigma ligands on the binding of [3H] dextromethorphan to guinea pig brain," Neurosci Lett., (1989) 97(1-2):175-80.
Koppel, C., et al, "Urinary metabolism of dextromethorphan in man," Arzneim.-Forsch./Drug Research 37: 1304-1306, 1987.
Koyuncuoglu, et al, "The treatment of heroin addicts with dextromethorphan: a double-blind comparison of dextromethorphan with chlorpromazine", Int J Clin Pharmacol Ther Toxicol. (1990) 28(4): 147-52.
Kronbach, et al., "High-performance liquid chromatographic assays for bufuralol 1'-hydroxylase, debrisoquine 4-hydroxylase, and dextromethorphan O-demethylase in microsomes and purified cytochrome P-450 isozymes of human liver", Anal Biochem. (1987) 162(1):24-32.
Kupfer , A., et al "Dextromethorphan as a safe probe for debrisoquine hydroxylation polymorphism," Lancet (1984) 2:517-518.
Kwiecinski, "Symptomatic treatment and palliative care of ALS", Neurol Neurochir Pol. (2001) 35:51-9, abstract only.
Largent, et al., "Structural determinants of sigma receptor affinity", Mol Pharmacol. (1987) 32(6):772-84.
Liu et al., "Dextromethorphan protects dopaminergic neurons against inflammation-mediated degeneration through inhibition of microglial activation", J Pharmacol Exp Ther. (2003) 305(1):212-218.
Manning, et al, "Continuous co-administration of dextromethorphan or MK-801 with morphine: attenuation of morphine dependence and naloxone-reversible attenuation of morphine tolerance," Pain (1996) 67: 79-88.
Mao, et al, "Oral administration of dextromethorphan prevents the development of morphine tolerance and dependence in rats," Pain (1996) 67: 361-8.
Mao, J., et al, "Intrathecal treatment with dextrorphan or ketamine potently reduces pain-related behaviors in a rat model of peripheral mononeuropathy," Brain Research 605: 164-168, 1993.
Maurice et al., "The Interaction between Neuroactive Steroids and the σ1 receptor function: Behavioral Consequences and Therapeutic opportunities," Brain Res. Brain Res. Rev., 2001; 37:116-32.
McCarthy, J.P., "Some less familiar drugs of abuse," Med. J. Australia 1971 (2): 1078-1081.
McDonald et al. "Recommended diagnostic criteria for multiple sclerosis: guidelines from the International Panel on the diagnosis of multiple sclerosis," Ann. Neurol. 50 (2001) 121-7.
McQuay, H.J., et al, "Dextromethorphan for the treatment of neurophatic pain: a double-blind randomised controlled crossover trial with integral n-of-1 design," Pain 59: 127-133, 1994.
Metman et al., "Dextromethorphan improves levodopa-induced dyskinesias in Parkinson's disease," Neurol. 51 (1998) 203-6.
Miller et al., Practice Parameter: The Care of the Patient with Amyotrophic Lateral Sclerosis, (An Evidence-based Review) Neurol., 1999; 52:1311-23.
Moghadamnia et al., "Physiologically based modelling of inhibition of metabolism and assessment of the relative potency of drug and metabolite: dextromethorphan vs. dextrorphan using quinidine inhibition," Br J Clin Pharmacol. Jul. 2003;56(1):57-67.
Moore et al. "A self report measure of affective lability," J. Neurol. Neurosurg. and Psychiatry. 63 (1997) 89-93.
Muller et al. Brain Injury. 77 (1996) 1309-11.
Musacchio et al. "Effects of dextromethorphan site ligands and allosteric modifiers on the binding of (+)-[3H]3-(-3-hydroxyphenyl)-N-(1-propyl)piperidine," Mol. Pharmacol. 35 (1989) 1-5.
Musacchio, et al., "Dextromethorphan binding sites in the guinea pig brain", Cell Mol Neurobiol., (1988) 8(2):149-56.
Musacchio, et al., "High affinity dextromethorphan binding sites in guinea pig brain: further characterization and allosteric interactions", J Pharmacol Exp Ther., (1988) 247(2):424-31.
Netzer et al., "Dextromethorphan Blocks N-Methyl-D-aspartate-induced Currents and voltage-operated inward currents in cultured cortical Neurons," Eur. J. Pharmacol., 1993; 238: 209-216.
Nielsen, M. D., et al, "A dose-effect study of the in vivo inhibitory effect of quinidine on sparteine oxidation in man," Br. J. Clin. Pharmacol. 29: 299-304, 1990.
Otton, et al., In vitro evidence against the oxidation of quinidine by the sparteine/debrisoquine monooxygenase of human liver, Drug Metab Dispos. (1988) 16(1):15-7.
Otton, et al., "Use of quinidine inhibition to define the role of the sparteine/debrisoquine cytochrome P450 in metoprolol oxidation by human liver microsomes", J Pharmacol Exp Ther., (1988) 247(1):242-7.
Palmer GC, "Neroprotections by NMDA Receptor Anatagonists in a Variety of Neropathologies," Curr. Drug Targets, 2001; 2:241-271.
Parvivzi, et al., "Pathological laughter and crying—A link to the cerebellum", Brain, 2001;124:1708-19.
PCT Search Report in equivalent PCT International Application No. PCT/US2003/022303.
Physician's Desk Reference, 44th Edition, 1990, pp. 670-671 (Medical Economics Company, 1990).
Plesan, et al, "Comparison of ketamine and dextromethorphan in potentiating the antinociceptive effect of morphine in rats," Anesth Analg. (1998) 86(4): 825-9,.
Poeck, K., "Pathophysiology of emotional disorders associated with brain damage," In: P.J. Vinken, G.W. Bruyn, editors. Handbook of Clinical Neurology. Amsterdam: North-Holland Publishing Company 1969; pp. 343-367.
Pope et al. J. Clin. Pharmacol. 39 (1999) 984.
Pope et al., "A Single-Dose and Multiple-Dose Pharmacokinetic Study with a Product Containing Dextromethorphan and Quinidine (AVP-923) in Poor and Exensive Metabolizers" 2002, vol. 42, No. 9, 59. Abstract Only.
Pope, et al., "Pharmacokinetics of dextromethorphan after single or multiple dosing in combination with quinidine in extensive and poor metabolizers", J Clin Pharmacol. (2004) 44(10):1132-1142.
Computer Folder named ACCP circa 1999.
Ramachander, et al., "Determination of dextrorphan in plasma and evaluation of bioavailability of dextromethorphan hydrobromide in humans," J Pharm Sci. (1977) 66(7):1047-8.
Smith et al., "The treatment of affective lability with dextromethorphan", Neurology, (1995) 45:604P.
Starkstein et al., "Prevalence and Clinical Correlates of Pathological affective display in Alzheimer's disease, ,"J. Neurol. Neurosurg. Psychiatry, 1995; 59:55-64.
Steinberg et al. "Dose escalation safety and tolerance study of the N-methyl-D-aspartate antagonist dextromethorphan in neurosurgery patients," J Neurosurg. 84 (1996) 860-6.
Tortella, F.C., et al, "Dextromethorphan and neuromodulation: old drug coughs up new activities," Trends in Pharm. Sci. 10: 501-507, 1989.
Tyndale et al. "Characterization of Cytochrome P-450 2D1 Activity in Rat Brain: High-Affinity Kinetics for Dextromethorphan," Drug Metab Dispos. Aug. 1999;27(8):924-30.
Udaka et al., "Pathologic Laughing and Crying Treated with Levodopa," Arch. Neurol. 1984, 41: 1095-1096.
Vetticaden et al., "Phenotypic Differences in Dextromethorphan Metabolism," Pharm. Res., Jan. 1989, 6(1):13-9.
Vinik, "Diabetic neuropathy: pathogenesis and therapy," Am J Med., (1999) 107: 17S-26S. cited by other.
Voirol et al. "Cytochrome P-450 activities in human and rat brain microsomes," Brain Res. Feb. 14, 2000;855(2):235-43.
von Moltke et al., "Multiple human cytochromes contribute to biotransformation of dextromethorphan in-vitro: role of CYP2C9, CYP2C19, CYP2D6, and CYP3A," J Pharm Pharmacol., (1998) 50(9): 997-1004.
Robinson, B. "Validation of a Caregiver Strain Index," Journal of Gerontology 38 (1983) 344-8.
Ross, et al., "Pathological display of affect in patients with depression and right frontal brain damage. An alternative mechanism," J Nerv Ment Dis. (1987) 175(3):165-72.
Sang et al., "Dextromethorphan and Memantine in Painful Diabetic Neuropathy and Postherpetic Neuralgia," Anesthesiology, 2002; 96: 1053-1061.
Sang, "NMDA-receptor antagonists in neuropathic pain: experimental methods to clinical trials," Pain Symptom Manage. (2000) 19(1 Suppl): S21-25.

Schadel et al., "Pharmacokinetics of Dextromethorphan and Metabolites i Humans: Influence of the CYP2D Phenotype and Quinidine Inhibition," J. Clin. Psychopharmacol., 1995; 15:263-9.

Schiffer et al., "Treatment of Pathologic Laughing and Weeping with Mithriptyline," N. Engl. J. Med. 1985, 312: 1480-1482.

Schmid et al., "Polymorphic Dextromethorphan Metabolism: Co-Segregation of Oxicative O-Demethylation with Debrisoquin Hydroxylation," Clin. Pharmacol. Ther., 1985; 38: 618-624.

Schmider et al., "Metabolism of dextromethorphan in vitro: involvement of cytochromes P450 2D6 and 3A3/4, with a possible role of 2E1," Biopharm Drug Dispos. Apr. 1997;18(3):227-40.

Shaw et al., "Brain Sciences in Psychiatry," London: Butterworth, 1982 (Contents pages only) 3 pages.

Shin et al., "Effect of Antipsychotic Drugs on Human Liver Cytochrome P-450 (CYP) Isoforms In Vitro: Preferential Inhibition of CYP2D6," Drug Metab Dispos. Sep. 1999;27(9):1078-84.

Walker, E. O., and Hunt, V. P., "An open label trial of dextromethorphan in Huntington's Disease," Clin. Neuropharmacol. 12: 322-330 (1989).

Weinbroum, et al., "The role of dextromethorphan in pain control," Can J Anaesth., 2000: 47: 585-596.

Wienkers et al. "Multiple Cytochrome P450 Enzymes Responsible for the Oxidative Metabolism of the Substituted (*S*)-3-Phenylpiperidine, (*S,S*)-3[3-(Methylsulfonyl)phenyl]-1-propylpiperidine Hydrochloride, in Human Liver Microsomes," Drug Metab Dispos. Dec. 2002;30(12):1372-7.

Wilson, S.A. Kinner, "Some Problems in Neurology," J. Neurol. Psychopathol., 1924; IV:299-333.

Wolf et al., "Treatment of "emotional Incontinence" with Levodopa," Neurol., 1979; 29:1435-6.

Yamamoto et al. "Differences in Cytochrome P450 Forms Involved in the Metabolism of *N,N*-Dipropyl-2-[4-methoxy-3-(2-phenylethoxy)phenyl]ethylamine monohydrochloride (NE-100), a Novel Sigma Ligand, in Human Liver and Intestine," Drug Metab Dispos. Jan. 2003;31(1):60-6.

Zhang et al. "Dextromethorphan: Enhancing its Systemic Availability by Way of Low-dose QWuinidine-mediated Inhibition of Cytochrome P4502D6," Clin. Pharm. Ther., 51(6) :647-655, 1992.

Zhang et al. "Dextromethorphan (DMT) and Quinidine: A Drug Interaction of Potential Therapeutic Utility," 1991, Pharmaceutical Research, vol. 8, No. 10, PPDM 8353. Abstract Only.

* cited by examiner

PHARMACEUTICAL COMPOSITIONS COMPRISING DEXTROMETHORPHAN AND QUINIDINE FOR THE TREATMENT OF NEUROLOGICAL DISORDERS

RELATED APPLICATION

This application is a continuation, under 35 U.S.C. §120, of International Patent Application No. PCT/US2003/022303, filed on Jul. 17, 2003 under the Patent Cooperation Treaty (PCT), which was published by the International Bureau in English on Jan. 22, 2004, which designates the United States and claims the benefit of U.S. Provisional Application No. 60/396,661, filed Jul. 17, 2002.

FIELD OF THE INVENTION

Pharmaceutical compositions and methods for treating neurological disorders are provided. The compositions comprise dextromethorphan in combination with quinidine.

BACKGROUND OF THE INVENTION

Patients suffering from neurodegenerative diseases or brain damage such as is caused by stroke or head injury often are afflicted with emotional problems associated with the disease or injury. The terms emotional lability and pseudobulbar affect are used by psychiatrists and neurologists to refer to a set of symptoms that are often observed in patients who have suffered a brain insult such as a head injury, stroke, brain tumor, or encephalitis, or who are suffering from a progressive neurodegenerative disease such as Amyotrophic Lateral Sclerosis (ALS, also called motor neuron disease or Lou Gehrig's disease), Parkinson's disease, Alzheimer's disease, or multiple sclerosis. In the great majority of such cases, emotional lability occurs in patients who have bilateral damage (damage which affects both hemispheres of the brain) involving subcortical forebrain structures.

Emotional lability, which is distinct from clinical forms of reactive or endogenous depression, is characterized by intermittent spasmodic outbursts of emotion (usually manifested as intense or even explosive crying or laughing) at inappropriate times or in the absence of any particular provocation. Emotional lability or pseudobulbar affect is also referred to by the terms emotionalism, emotional incontinence, emotional discontrol, excessive emotionalism, and pathological laughing and crying. The feelings that accompany emotional lability are often described in words such as "disconnectedness," since patients are fully aware that an outburst is not appropriate in a particular situation, but they do not have control over their emotional displays.

Emotional lability or pseudobulbar affect becomes a clinical problem when the inability to control emotional outbursts interferes in a substantial way with the ability to engage in family, personal, or business affairs. For example, a businessman suffering from early-stage ALS or Parkinson's disease might become unable to sit through business meetings, or a patient might become unable to go out in public, such as to a restaurant or movie, due to transient but intense inability to keep from crying or laughing at inappropriate times in front of other people. These symptoms can occur even though the patient still has more than enough energy and stamina to do the physical tasks necessary to interact with other people. Such outbursts, along with the feelings of annoyance, inadequacy, and confusion that they usually generate and the visible effects they have on other people, can severely aggravate the other symptoms of the disease; they lead to feelings of ostracism, alienation, and isolation, and they can render it very difficult for friends and family members to provide tolerant and caring emotional support for the patient.

SUMMARY OF THE INVENTION

There remains a need for additional or improved forms of treatment for emotional lability and other chronic disorders, such as chronic pain. Such a treatment preferably provides at least some degree of improvement compared to other known drugs, in at least some patients. A method for treating emotional lability in at least some patients suffering from neurologic impairment, such as a progressive neurologic disease, is desirable.

A method of treating emotional lability, pseudobulbar affect, and other chronic conditions in human patients who are in need of such treatment, without oversedation or otherwise significantly interfering with consciousness or alertness is provided. The treatment involves administering dextromethorphan in combination with a minimum dosage of quinidine.

In a first embodiment, a method for treating pseudobulbar affect or emotional lability is provided, the method including administering to a patient in need thereof dextromethorphan in combination with quinidine, wherein an amount of dextromethorphan administered includes from about 20 mg/day to about 200 mg/day, and wherein an amount of quinidine administered includes from about 10 mg/day to less than about 50 mg/day.

In an aspect of the first embodiment, the pseudobulbar affect or emotional lability is caused by a neurodegenerative disease or condition or a brain injury.

In a second embodiment, a method for treating neuropathic pain is provided, the method including administering to a patient in need thereof dextromethorphan in combination with quinidine, wherein an amount of dextromethorphan administered includes from about 20 mg/day to about 200 mg/day, and wherein an amount of quinidine administered includes from about 10 mg/day to less than about 50 mg/day.

In a third embodiment, a method for treating a neurodegenerative disease or condition is provided, the method including administering to a patient in need thereof dextromethorphan in combination with quinidine, wherein an amount of dextromethorphan administered includes from about 20 mg/day to about 200 mg/day, and wherein an amount of quinidine administered includes from about 10 mg/day to less than about 50 mg/day.

In an aspect of the third embodiment, the neurodegenerative disease or condition is selected from the group consisting of amyotrophic lateral sclerosis, multiple sclerosis, Parkinson's disease, and Alzheimer's disease.

In a fourth embodiment, a method for treating a brain injury is provided, the method including administering to a patient in need thereof dextromethorphan in combination with quinidine, wherein an amount of dextromethorphan administered includes from about 20 mg/day to about 200 mg/day, and wherein an amount of quinidine administered includes from about 10 mg/day to less than about 50 mg/day.

In an aspect of the fourth embodiment, the brain injury is selected from the group consisting of stroke, traumatic brain injury, ischemic event, hypoxic event, and neuronal death.

In aspects of the first through fourth embodiments, the dextromethorphan and the quinidine are administered as one combined dose per day.

In aspects of the first through fourth embodiments, the dextromethorphan and the quinidine are administered as at least two combined doses per day.

In aspects of the first through fourth embodiments, the amount of quinidine administered includes from about 20 mg/day to about 45 mg/day.

In aspects of the first through fourth embodiments, the amount of dextromethorphan administered includes from about 20 mg/day to about 60 mg/day.

In aspects of the first through fourth embodiments, at least one of the quinidine and the dextromethorphan is in a form of a pharmaceutically acceptable salt.

In aspects of the first through fourth embodiments, the pharmaceutically acceptable salt is selected from the group consisting of salts of alkali metals, salts of lithium, salts of sodium, salts of potassium, salts of alkaline earth metals, salts of calcium, salts of magnesium, salts of lysine, salts of N,N'-dibenzylethylenediamine, salts of chloroprocaine, salts of choline, salts of diethanolamine, salts of ethylenediamine, salts of meglumine, salts of procaine, salts of tris, salts of free acids, salts of free bases, inorganic salts, salts of sulfate, salts of hydrochloride, and salts of hydrobromide.

In aspects of the first through fourth embodiments, the quinidine includes quinidine sulfate and the dextromethorphan includes dextromethorphan hydrobromide, and wherein an amount of quinidine sulfate administered includes from about 30 mg/day to 60 mg/day and wherein an amount of dextromethorphan hydrobromide administered includes from about 30 mg/day to about 60 mg/day.

In a fifth embodiment, a method for treating pseudobulbar affect or emotional lability is provided, the method including administering to a patient in need thereof dextromethorphan in combination with quinidine, wherein the dextromethorphan and the quinidine are administered in a combined dose, and wherein a weight ratio of dextromethorphan to quinidine in the combined dose is about 1:1.25 or less.

In an aspect of the fifth embodiment, the pseudobulbar affect or emotional lability is caused by a neurodegenerative disease or condition or a brain injury.

In a sixth embodiment, a method for treating neuropathic pain is provided, the method including administering to a patient in need thereof dextromethorphan in combination with quinidine, wherein the dextromethorphan and the quinidine are administered in a combined dose, and wherein a weight ratio of dextromethorphan to quinidine in the combined dose is about 1:1.25 or less.

In a seventh embodiment, a method for treating a neurodegenerative disease or condition is provided, the method including administering to a patient in need thereof dextromethorphan in combination with quinidine, wherein the dextromethorphan and the quinidine are administered in a combined dose, and wherein a weight ratio of dextromethorphan to quinidine in the combined dose is about 1:1.25 or less.

In an aspect of the seventh embodiment, the neurodegenerative disease or condition is selected from the group consisting of amyotrophic lateral sclerosis, multiple sclerosis, Parkinson's disease, and Alzheimer's disease.

In an eighth embodiment, a method for treating a brain injury is provided, the method including administering to a patient in need thereof dextromethorphan in combination with quinidine, wherein the dextromethorphan and the quinidine are administered in a combined dose, and wherein a weight ratio of dextromethorphan to quinidine in the combined dose is about 1:1.25 or less.

In an aspect of the eighth embodiment, the brain injury is selected from the group consisting of stroke, traumatic brain injury, ischemic event, hypoxic event, and neuronal death.

In aspects of the fifth through eighth embodiments, the weight ratio of dextromethorphan to quinidine in the combined dose is about 1:0.75 or less.

In aspects of the fifth through eighth embodiments, the amount of quinidine administered includes from about 20 mg/day to about 45 mg/day, and wherein the amount of dextromethorphan administered includes from about 20 mg/day to about 60 mg/day.

In aspects of the fifth through eighth embodiments, at least one of the quinidine and the dextromethorphan is in a form of a pharmaceutically acceptable salt.

In aspects of the fifth through eighth embodiments, the pharmaceutically acceptable salt is selected from the group consisting of salts of alkali metals, salts of lithium, salts of sodium, salts of potassium, salts of alkaline earth metals, salts of calcium, salts of magnesium, salts of lysine, salts of N,N'-dibenzylethylenediamine, salts of chloroprocaine, salts of choline, salts of diethanolamine, salts of ethylenediamine, salts of meglumine, salts of procaine, salts of tris, salts of free acids, salts of free bases, inorganic salts, salts of sulfate, salts of hydrochloride, and salts of hydrobromide.

In aspects of the fifth through eighth embodiments, the quinidine includes quinidine sulfate and the dextromethorphan includes dextromethorphan hydrobromide, and wherein an amount of quinidine sulfate administered includes from about 30 mg/day to about 60 mg/day and wherein an amount of dextromethorphan hydrobromide administered includes from about 30 mg/day to about 60 mg/day.

In aspects of the fifth through eighth embodiments, one combined dose is administered per day.

In aspects of the fifth through eighth embodiments, two or more combined doses are administered per day.

In a ninth embodiment, a pharmaceutical composition suitable for use in treating pseudobulbar affect or emotional lability is provided, the composition including a tablet or a capsule, the tablet or capsule including dextromethorphan and quinidine, wherein a weight ratio of dextromethorphan to quinidine is about 1:1.25 or less.

In an aspect of the ninth embodiment, the pseudobulbar affect or emotional lability is caused by a neurodegenerative disease or condition or a brain injury.

In a tenth embodiment, a pharmaceutical composition suitable for use in treating neuropathic pain is provided, the composition including a tablet or a capsule, the tablet or capsule including dextromethorphan and quinidine, wherein a weight ratio of dextromethorphan to quinidine is about 1:1.25 or less.

In an eleventh embodiment, a pharmaceutical composition suitable for use in treating a neurodegenerative disease or condition is provided, the composition including a tablet or a capsule, the tablet or capsule including dextromethorphan and quinidine, wherein a weight ratio of dextromethorphan to quinidine is about 1:1.25 or less.

In an aspect of the eleventh embodiment, the neurodegenerative disease or condition is selected from the group consisting of amyotrophic lateral sclerosis, multiple sclerosis, Parkinson's disease, and Alzheimer's disease.

In a twelfth embodiment, a pharmaceutical composition suitable for use in a brain injury is provided, the composition including a tablet or a capsule, the tablet or capsule including dextromethorphan and quinidine, wherein a weight ratio of dextromethorphan to quinidine is about 1:1.25 or less.

In an aspect of the twelfth embodiment, the brain injury is selected from the group consisting of stroke, traumatic brain injury, ischemic event, hypoxic event, and neuronal death.

In aspects of the ninth through twelfth embodiments, the weight ratio of dextromethorphan to quinidine is about 1:0.75 or less.

In aspects of the ninth through twelfth embodiments, the quinidine is present in an amount of from about 20 mg to about 45 mg, and wherein the dextromethorphan is present in an amount of from about 20 mg to about 60 mg.

In aspects of the ninth through twelfth embodiments, at least one of the quinidine and the dextromethorphan is in a form of a pharmaceutically acceptable salt.

In aspects of the ninth through twelfth embodiments, the pharmaceutically acceptable salt is selected from the group consisting of salts of alkali metals, salts of lithium, salts of sodium, salts of potassium, salts of alkaline earth metals, salts of calcium, salts of magnesium, salts of lysine, salts of N,N'-dibenzylethylenediamine, salts of chloroprocaine, salts of choline, salts of diethanolamine, salts of ethylenediamine, salts of meglumine, salts of procaine, salts of tris, salts of free acids, salts of free bases, inorganic salts, salts of sulfate, salts of hydrochloride, and salts of hydrobromide.

In aspects of the ninth through twelfth embodiments, the quinidine includes quinidine sulfate and the dextromethorphan includes dextromethorphan hydrobromide, wherein the quinidine sulfate is present in an amount of from about 30 mg to about 60 mg, and wherein the dextromethorphan hydrobromide is present in an amount of from about 30 mg to about 60 mg.

In a thirteenth embodiment, use of dextromethorphan and quinidine in the preparation of a medicament for treating pseudobulbar affect or emotional lability is provided, wherein the medicament includes a capsule or a tablet, and wherein dextromethorphan and quinidine are present in the capsule or tablet at a weight ratio of dextromethorphan to quinidine of 1:1.25 or less.

In an aspect of the thirteenth embodiment, the pseudobulbar affect or emotional lability is caused by a neurodegenerative disease or condition or a brain injury.

In a fourteenth embodiment, use of dextromethorphan and quinidine in the preparation of a medicament for treating neuropathic pain is provided, wherein the medicament includes a capsule or a tablet, and wherein dextromethorphan and quinidine are present in the capsule or tablet at a weight ratio of dextromethorphan to quinidine of 1:1.25 or less.

In a fifteenth embodiment, use of dextromethorphan and quinidine in the preparation of a medicament for treating a neurodegenerative disease or condition is provided, wherein the medicament includes a capsule or a tablet, and wherein dextromethorphan and quinidine are present in the capsule or tablet at a weight ratio of dextromethorphan to quinidine of 1:1.25 or less.

In an aspect of the fifteenth embodiment, the neurodegenerative disease or condition is selected from the group consisting of amyotrophic lateral sclerosis, multiple sclerosis, Parkinson's disease, and Alzheimer's disease.

In a sixteenth embodiment, use of dextromethorphan and quinidine in the preparation of a medicament for treating a brain injury is provided, wherein the medicament includes a capsule or a tablet, and wherein dextromethorphan and quinidine are present in the capsule or tablet at a weight ratio of dextromethorphan to quinidine of 1:1.25 or less.

In an aspect of the sixteenth embodiment, the brain injury is selected from the group consisting of stroke, traumatic brain injury, ischemic event, hypoxic event, and neuronal death.

In aspects of the thirteenth through sixteenth embodiments, dextromethorphan and quinidine are present in the capsule or tablet at a weight ratio of dextromethorphan to quinidine of 1:0.75 or less.

In aspects of the thirteenth through sixteenth embodiments, at least one of the quinidine and the dextromethorphan is in a form of a pharmaceutically acceptable salt.

In aspects of the thirteenth through sixteenth embodiments, the pharmaceutically acceptable salt is selected from the group consisting of salts of alkali metals, salts of lithium, salts of sodium, salts of potassium, salts of alkaline earth metals, salts of calcium, salts of magnesium, salts of lysine, salts of N,N'-dibenzylethylenediamine, salts of chloroprocaine, salts of choline, salts of diethanolamine, salts of ethylenediamine, salts of meglumine, salts of procaine, salts of tris, salts of free acids, salts of free bases, inorganic salts, salts of sulfate, salts of hydrochloride, and salts of hydrobromide.

In aspects of the thirteenth through sixteenth embodiments, the quinidine includes quinidine sulfate and the dextromethorphan includes dextromethorphan hydrobromide, wherein the quinidine sulfate is present in an amount of from about 30 mg to about 60 mg, and wherein the dextromethorphan hydrobromide is present in an amount of from about 30 mg to about 60 mg.

In aspects of the thirteenth through sixteenth embodiments, the quinidine is present in an amount of from about 20 mg to about 45 mg, and wherein the dextromethorphan is present in an amount of from about 20 mg to about 60 mg.

DETAILED DESCRIPTION OF THE PREFERRED EMBODIMENT

Figure 1:
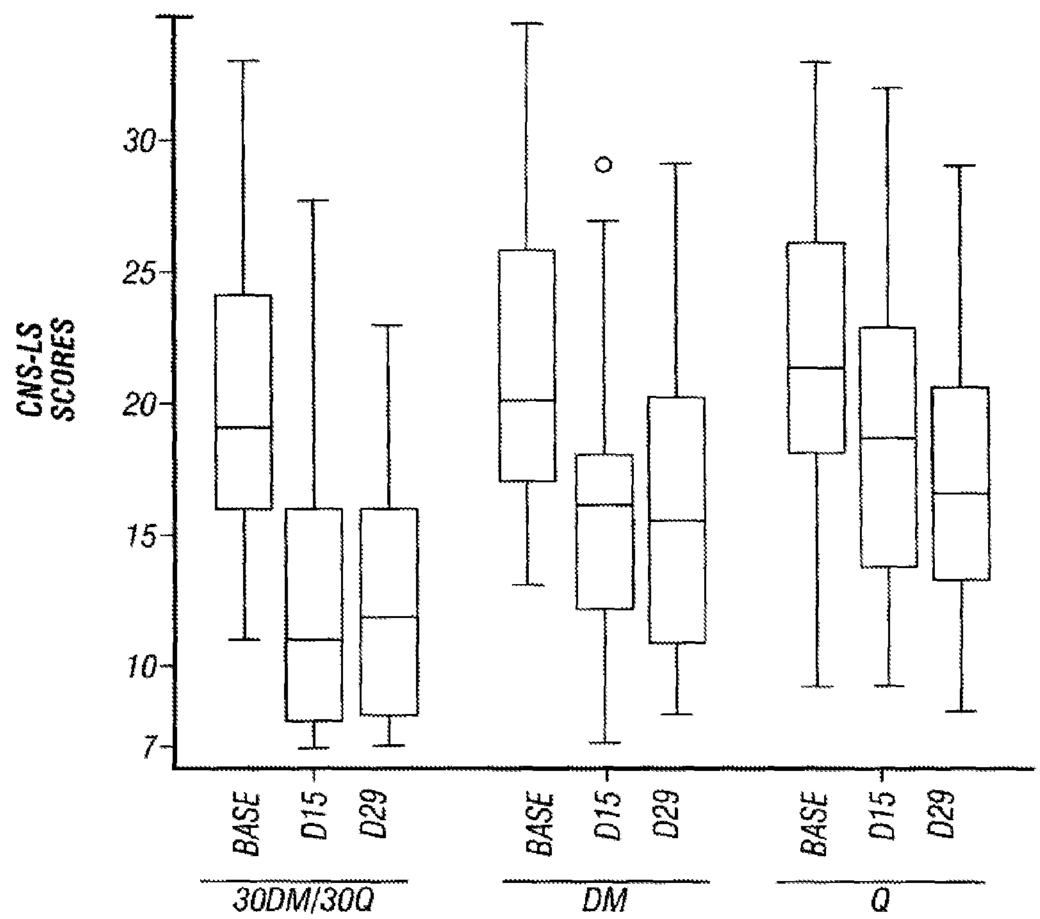
FIG. 1 provides a box plot of CNS-LS scores for Clinical Study #4. The distributions of CNS-LS scores are symmetrical and contain only one outlier. These distributions support the use of ANCOVA for the analysis of the CNS-LS scores. As prospectively specified in the study protocol, the differences in mean improvement in CNS-LS cores, adjusted for center and baseline CNS-LS scores, were analyzed by using linear regression according to the ANCOVA method of Frison and Pocock. The results of this analysis are in Table 30. The results of the additional analyses without any adjustments or with an adjustment for baseline CNS-LS score alone are also in this table.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Emotional lability or pseudobulbar affect is associated with a number of neurological diseases, such as stroke (House et al., BMJ, 1989; 298:991-4), multiple sclerosis (MS) (Cotrell et al., J. Neurol. Psychopathol., 1926; 7:1-30; Feinstein et al., Arch. Neurol., 1997; 54:1116-21), amyotrophic lateral sclerosis (ALS) (Miller et al., Neurol., 1999; 52:1311-23; Jackson et al., Semin. Neurol. 1998; 18:27-39; Poeck, K., Pathophysiology of emotional disorders associated with brain damage. In: P. J. Vinken, G. W. Bruyn, editors. Handbook of Clinical Neurology. Amsterdam: North-Holland Publishing Company 1969; pp. 343-67), Alzheimer's disease (Starkstein et al., J. Neurol. Neurosurg. Psychiatry, 1995; 59:55-64), and traumatic brain injury (Brooks, N., Acta Neurochirurgica Suppl., 44 1988; 59-64). Studies have suggested that pseudobulbar affect occurs in up to 50% of patients with ALS (Gallagher, J. P., Acta Neurol. Scand. 1989; 80:114-7).

Emotional lability or pseudobulbar affect in the context of neurological injury can be considered a disconnection syndrome resulting from loss of cortical communication with the brainstem or cerebellum Wilson SAK, *J.* Neurol. Psychopathol., 1924; IV:299-333; Parvivzi et al., Brain, 2001; 124: 1708-19). At the neurotransmitter level, disruptions of ascending and descending serotonergic pathways arising in the brainstem, and dysregulation of dopaminergic projections to the striatum and cortex have been implicated (Andersen et al., Stroke, 1994; 25:1050-2; Ross et al., J. Nerv. Ment. Dis., 1987; 175:165-72; Shaw et al., Brain Sciences in Psychiatry, London: Butterworth, 1982; Udaka et al., Arch. Neurol. 1984; 41:1095-6).

A body of evidence suggests that pseudobulbar affect can be modulated through pharmacologic intervention. In 1979, Wolf reported that levodopa was effective in subjects with pathological laughing (Wolf et al., Neurol., 1979; 29:1435-6.). However, in a follow-up study, only 10 of 25 subjects responded satisfactorily to treatment (Udaka et al., Arch. Neurol., 1984; 41:1095-6). There have been reports of symptomatic benefit with other drugs, including amantadine, imipramine, desipramine, nortriptyline, amitriptyline, sertraline, fluoxetine, levodopa, methylphenidate, and thyrotropin-releasing hormone (Dark et al., Austr. N. Zeal. J. Psychiatry, 1996; 30:472-9; Iannoccone et al., Clin. Neuropharm., 1996; 19:532-5).

The best previously known therapies for treating emotional lability involve the drugs amitriptyline, amantadine, and levodopa. Although reports such as Udaka et al., Arch. Neurol. 1984, 41: 1095-1096, and Schiffer et al., N. Engl. J. Med. 1985, 312: 1480-1482 indicate that these compounds may be effective in helping reduce pathological displays of emotion in some patients, they make it clear that none of these prior art drugs are effective in all patients, and even in patients who receive some benefit, the effect usually stops far short of an effective cure. A common practice for many clinical neurologists is to prescribe amitriptyline and amantadine, one at a time, in the hope that one of them might be able to provide any level of improvement in the patient's condition. However, all both fall short of offering an effective cure. In addition, levodopa is not satisfactory, since it has other effects and is a relatively powerful drug.

ALS is a neurodegenerative disease produced by progressive loss of upper and lower motor neurons. Up to 50 percent of patients with ALS exhibit emotional lability, and it is more prevalent in those with the bulbar form of ALS (Gallagher J P, Acta Neurol. Scand., 1989; 80:114-7). Based on the notion that excitotoxicity secondary to impaired recycling of glutamate may be a factor in the etiology of ALS, riluzole, a glutamate release inhibitor, has been used to treat ALS (Jerusalem et al., Neurology, 1996; 47:S218-20; Doble A., Neurology, 1996; 47:S233-41). Riluzole modestly extends life span but does not confer symptomatic benefit (Bensimon et al., N. Eng. J. Med., 1994; 330:585-91; Kwiecinski H, Neurol. Neurochir. Pol., 2001; 35:51-9).

Because of the possibility that an excitotoxic process involving glutamate is etiologically implicated in ALS, several investigators have attempted to modify or arrest the course of ALS by the administration of dextromethorphan (DM). DM is an noncompetitive antagonist of the N-methyl-D-aspartate-sensitive ionotropic glutamate receptor, and it acts by reducing the level of excitatory activity. However, DM is extensively metabolized to dextrorphan (DX) and a number of other metabolites. Cytochrome P450 2D6 (CYP2D6) is the key enzyme responsible for the formation of DX from DM. A subset of the population, 5 to 10% of Caucasians, has reduced activity of this enzyme (Hildebrand et al., Eur. J. Clin. Pharmacol., 1989; 36:315-318). Such individuals are referred to as "poor metabolizers" of DM in contrast to the majority of individuals who are referred to as "extensive metabolizers" of DM (Vetticaden et al., Pharm. Res., 1989; 6:13-9).

A number of in vitro studies have been undertaken to determine the types of drugs that inhibit CYP2D6 activity. Quinidine (Q) is one of the most potent of those that have been studied (Inaba et al., Br. J. Clin. Pharmacol., 1986; 22:199-200). These observations led to the hypothesis that concomitant dosing with Q could increase the concentration of DM in plasma.

A number of chronic disorders other than emotional lability also have symptoms which are known to be very difficult to treat, and often fail to respond to safe, non-addictive, and non-steroid medications. Disorders such as intractable coughing fail to respond to conventional medicines and are typically treated by such drugs as codeine, morphine, or the anti-inflammatory steroid prednisone. These drugs are unacceptable for long-term treatment due to dangerous side effects, long-term risks to the patient's health, or the danger of addiction. There has been no satisfactory treatment for the severe itching and rash associated with dermatitis. Drugs such as prednisone and even tricyclic antidepressants, as well as topical applications have been employed, but do not appear to offer substantial and consistent relief. Chronic pain due to conditions such as stroke, cancer, and trauma, as well as neuropathic pain resulting from conditions such as diabetes and shingles (herpes zoster), for example, is also a problem which resists treatment. Neuropathic pain includes, for example, diabetic neuropathy, postherpetic neuralgia, phantom limb pain, trigeminal neuralgia, and sciatica. Postherpetic neuralgia (PHN) is a complication of shingles and occurs in approximately ten percent of patients with herpes zoster. The incidence of PHN increases with age. Diabetic neuropathy is a common complication of diabetes which increases with the duration of the disease. The pain for these types of neuropathies has been described as a burning steady pain often punctuated with stabbing pains, pins and needles pain, and toothache-like pain. The skin can be sensitive with dysesthetic sensations to even light touch and clothing. The pain can be exacerbated by activity, temperature change, and emotional upset. The pain can be so severe as to preclude daily activities or result in sleep disturbance or anorexia. The mechanisms involved in producing pain of these types are not well understood, but may involve degeneration of myelinated nerve fibers. It is known that in diabetic neuropathy, both small and large nerve fibers deteriorate resulting in reduced thresholds for tolerance of thermal sensitivity, pain, and vibration. Dysfunction of both large and small fiber functions is more severe in the lower limbs when pain develops. Most of the physiological measurements of nerves that can be routinely done in patients experiencing neuropathic pain demonstrate a slowing of nerve conduction over time. To date, treatment for neuropathic pain has been less than universally successful. Chronic pain is estimated to affect millions of people.

Dextromethorphan is widely used as a cough syrup, and it has been shown to be sufficiently safe in humans to allow its use as an over-the-counter medicine. It is well tolerated in oral dosage form, either alone or with quinidine, at up to 120 milligrams (mg) per day, and a beneficial effect may be observed when receiving a substantially smaller dose (e.g., 30 mg/day) (U.S. Pat. No. 5,206,248 to Smith).

The chemistry of dextromethorphan and its analogs is described in various references such as Rodd, E. H., Ed., Chemistry of Carbon Compounds, Elsevier Publ., N.Y., 1960; Goodman and Gilman's Pharmacological Basis of Therapeutics; Choi, Brain Res., 1987, 403: 333-336; and U.S. Pat. No. 4,806,543. Its chemical structure is as follows:

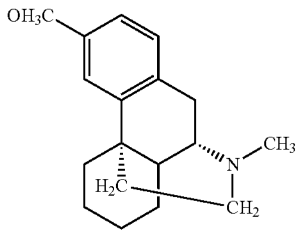

Dextromethorphan is the common name for (+)-3-methoxy-N-methylmorphinan. It is one of a class of molecules that are dextrorotatory analogs of morphine-like opioids. The term "opiate" refers to drugs that are derived from opium, such as morphine and codeine. The term "opioid" is broader. It includes opiates, as well as other drugs, natural or synthetic, which act as analgesics and sedatives in mammals.

Most of the addictive analgesic opiates, such as morphine, codeine, and heroin, are levorotatory stereoisomers (they rotate polarized light in the so-called left-handed direction). They have four molecular rings in a configuration known as a "morphinan" structure, which is depicted as follows:

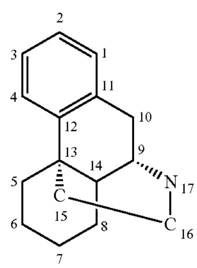

In this depiction, the carbon atoms are conventionally numbered as shown, and the wedge-shaped bonds coupled to carbon atoms 9 and 13 indicate that those bonds rise out of the plane of the three other rings in the morphinan structure. Many analogs of this basic structure (including morphine) are pentacyclic compounds that have an additional ring formed by a bridging atom (such as oxygen) between the number 4 and 5 carbon atoms.

Many dextrorotatory analogs of morphine are much less addictive than the levorotatory compounds. Some of these dextrorotatory analogs, including dextromethorphan and dextrorphan, are enantiomers of the morphinan structure. In these enantiomers, the ring that extends out from carbon atoms 9 and 13 is oriented in the opposite direction from that depicted in the above structure.

While not wishing to be limited to any particular mechanism of action, dextromethorphan is known to have at least three distinct receptor activities which affect central nervous system (CNS) neurons. First, it acts as an antagonist at N-methyl-D-aspartate (NMDA) receptors. NMDA receptors are one of three major types of excitatory amino acid (EAA) receptors in CNS neurons. Since activation of NMDA receptors causes neurons to release excitatory neurotransmitter molecules (primarily glutamate, an amino acid), the blocking activity of dextromethorphan at these receptors reduces the level of excitatory activity in neurons having these receptors. Dextromethorphan is believed to act at the phencyclidine (PCP) binding site, which is part of the NMDA receptor complex. Dextromethorphan is relatively weak in its NMDA antagonist activity, particularly compared to drugs such as MK-801 (dizocilpine) and phencyclidine. Accordingly, when administered at approved dosages, dextromethorphan is not believed to cause the toxic side effects (discussed in U.S. Pat. No. 5,034,400 to Olney) that are caused by powerful NMDA antagonists such as MK-801 or PCP.

Dextromethorphan also functions as an agonist at certain types of inhibitory receptors; unlike EAA receptors, activation of inhibitory receptors suppresses the release of excitatory neurotransmitters by affected cells. Initially, these inhibitory receptors were called sigma opiate receptors. However, questions have been raised as to whether they are actually opiate receptors, so they are now generally referred to as sigma ($\sigma$) receptors. Subsequent experiments showed that dextromethorphan also binds to another class of inhibitory receptors that are closely related to, but distinct from, sigma receptors. The evidence, which indicates that non-sigma inhibitory receptors exist and are bound by dextromethorphan, is that certain molecules which bind to sigma receptors are not able to completely block the binding of dextromethorphan to certain types of neurons that are known to have inhibitory receptors (Musacchio et al., Cell Mol. Neurobiol., 1988 June, 8(2):149-56; Musacchio et al., J. Pharmacol. Exp. Ther., 1988 November, 247(2):424-31; Craviso et al., Mol. Pharmacol., 1983 May, 23(3):629-40; Craviso et al., Mol. Pharmacol., 1983 May, 23(3):619-28; and Klein et al., Neurosci. Lett., 1989 Feb. 13, 97(1-2):175-80). These receptors are generally called "high-affinity dextromethorphan receptors" or simply "DM receptors" in the scientific literature. As used herein, the phrase "dextromethorphan-binding inhibitory receptors" includes both sigma and non-sigma receptors which undergo affinity-binding reactions with dextromethorphan and which, when activated by dextromethorphan, suppress the release of excitatory neurotransmitters by the affected cells (Largent et al., Mol. Pharmacol., 1987 December, 32(6):772-84).

Dextromethorphan also decreases the uptake of calcium ions ($Ca^{++}$) by neurons. Calcium uptake, which occurs during transmission of nerve impulses, involves at least two different types of channels, known as N-channels and L-channels. Dextromethorphan suppressed calcium uptake fairly strongly in certain types of cultured neurons (synaptosomes) which contain N-channels; it also suppressed calcium uptake, although less strongly, in other cultured neurons (PC12 cells) which contain L-channels (Carpenter et al., Brain Res., 1988 Jan. 26, 439(1-2):372-5).

An increasing body of evidence indicates dextromethorphan has therapeutic potential for treating several neuronal disorders (Zhang et al., Clin. Pharmacol. Ther. 1992; 51: 647-655; Palmer G C, Curr. Drug Targets, 2001; 2: 241-271; and Liu et al., J. Pharmacol. Exp. Ther. 2003; 21: 21; Kim et al., Life Sci., 2003; 72: 769-783). Pharmacological studies demonstrate that DM is a noncompetitive NMDA antagonist that has neuroprotective, anticonvulsant and antinociceptive activities in a number of experimental models (Desmeules et al., J. Pharmacol. Exp. Ther., 1999; 288: 607-612). In addition to acting as an NMDA antagonist, both DM and its primary metabolite, dextrorphan, bind to sigma-1 sites, inhibit calcium flux channels and interact with high voltage-gated sodium channels (Dickenson et al., Neuropharmacology, 1987; 26: 1235-1238; Carpenter et al., Brain Res., 1988; 439: 372-375; Netzer et al., Eur. J. Pharmacol., 1993; 238: 209-216). Recent reports indicate that an additional neuroprotective mechanism of DM may include interference with the inflammatory responses associated with some neurodegenerative disorders that include Parkinson's disease and Alzheimer's disease (Liu et al., J. Pharmacol. Exp. Ther., 2003; 21: 21). The potential efficacy of DM as a neuroprotectant was explored in limited clinical trials in patients with amyotrophic lateral sclerosis (Gredal et al., Acta Neurol. Scand. 1997; 96: 8-13; Blin et al., Clin. Neuropharmacol., 1996; 19: 189-192) Huntington's disease (Walker et al., Clin. Neuropharmacol., 1989; 12: 322-330) and Parkinson's Disease (Chase et al., J. Neurol., 2000; 247 Suppl 2: II36-42). DM was also examined in patients with various types of neuropathic pain (Mcquay et al., Pain, 1994; 59: 127-133; Vinik A I, Am. J. Med., 1999; 107: 17S-26S; Weinbroum et al., Can. J. Anaesth., 2000; 47: 585-596; Sang et al., Anesthesiology, 2002; 96: 1053-1061; Heiskanen et al., Pain, 2002; 96: 261-267; Ben Abraham et al., Clin. J. Pain, 2002; 18: 282-285; Sang C N, J. Pain Symptom Manage., 2000; 19: S21-25). Although the pharmacological profile of DM points to clinical efficacy, most clinical trials have been disappointing with equivocal efficacy for DM compared to placebo treatment.

Several investigators suggested that the limited benefit seen with DM in clinical trials is associated with rapid hepatic metabolism that limits systemic drug concentrations. In one trial in patients with Huntington's disease, plasma concentrations were undetectable in some patients after DM doses that were eight times the maximum antitussive dose (Walker et al., Clin. Neuropharmacol., 1989; 12: 322-330).

As discussed above, DM undergoes extensive hepatic O-demethylation to dextrorphan that is catalyzed by CYP2D6. This is the same enzyme that is responsible for polymorphic debrisoquine hydroxylation in humans (Schmid et al., Clin. Pharmacol. Ther., 1985; 38: 618-624). An alternate pathway is mediated primarily by CYP3A4 and N-demethylation to form 3-methoxymorphinan (Von Moltke et al., J. Pharm. Pharmacol., 1998; 50: 997-1004). Both DX and 3-methoxymorphinan can be further demethylated to 3-hydroxymorphinan that is then subject to glucuronidation. The metabolic pathway that converts DM to DX is dominant in the majority of the population and is the principle for using DM as a probe to phenotype individuals as CYP2D6 extensive and poor metabolizers (Kupfer et al., Lancet 1984; 2: 517-518; Guttendorf et al., Ther. Drug Monit., 1988; 10: 490-498). Approximately 7% of the Caucasian population shows the poor metabolizer phenotype, while the incidence of poor metabolizer phenotype in Chinese and Black African populations is lower (Droll et al., Pharmacogenetics, 1998; 8: 325-333). A study examining the ability of DM to increase pain threshold in extensive and poor metabolizers found antinociceptive effects of DM were significant in poor metabolizers but not in extensive metabolizers (Desmeules et al., J. Pharmacol. Exp. Ther., 1999; 288: 607-612). The results are consistent with direct effects of parent DM rather than the DX metabolite on neuromodulation.

One approach for increasing systemically available DM is to coadminister the CYP2D6 inhibitor, quinidine, to protect DM from metabolism (Zhang et al., Clin. Pharmacol. Ther. 1992; 51: 647-655). Quinidine administration can convert subjects with extensive metabolizer phenotype to poor metabolizer phenotype (Inaba et al., Br. J. Clin. Pharmacol., 1986; 22: 199-200). When this combination therapy was tried in amyotrophic lateral sclerosis patients it appeared to exert a palliative effect on symptoms of pseudobulbar affect (Smith et al., Neurol., 1995; 54: 604P). Combination treatment with DM and quinidine also appeared effective for patients with chronic pain that could not be adequately controlled with other medications. This observation is consistent with a report that showed DM was effective in increasing pain threshold in poor metabolizers and in extensive metabolizers given quinidine, but not in extensive metabolizers (Desmeules et al., J. Pharmacol. Exp. Ther., 1999; 288: 607-612). To date, most studies have used quinidine doses ranging from 50 to 200 mg to inhibit CYP2D6 mediated drug metabolism, but no studies have identified a minimal dose of quinidine for enzyme inhibition.

The highly complex interactions between different types of neurons having varying populations of different receptors, and the cross-affinity of different receptor types for dextromethorphan as well as other types of molecules which can interact with some or all of those same types of receptors, render it very difficult to attribute the overall effects of dextromethorphan to binding activity at any particular receptor type. Nevertheless, it is believed that dextromethorphan suppresses neuronal activity by means of at least three molecular functions: it reduces activity at (excitatory) NMDA receptors; it inhibits neuronal activity by binding to certain types of inhibitory receptors; and it suppresses calcium uptake through N-channels and L-channels.

Unlike some analogs of morphine, dextromethorphan has little or no agonist or antagonist activity at various other opiate receptors, including the mu (μ) and kappa (κ) classes of opiate receptors. This is highly desirable, since agonist or antagonist activity at those opiate receptors can cause undesired side effects such as respiratory depression (which interferes with breathing) and blockade of analgesia (which reduces the effectiveness of pain-killers).

Accordingly, emotional lability or pseudobulbar affect can be treated in at least some patients by means of administering a drug which functions as an antagonist at NMDA receptors and as an agonist at dextromethorphan-binding inhibitory receptors, and wherein the drug is also characterized by a lack of agonist or antagonist activity at mu or kappa opiate receptors, namely, dextromethorphan.

It has long been known that in most people (estimated to include about 90% of the general population in the United States), dextromethorphan is rapidly metabolized and eliminated by the body (Ramachander et al., J. Pharm. Sci., 1977 July, 66(7):1047-8; and Vetticaden et al., Pharm. Res., 1989 January, 6(1):13-9). This elimination is largely due to an enzyme known as the P450 2D6 (or IID6) enzyme, which is one member of a class of oxidative enzymes that exist in high concentrations in the liver, known as cytochrome P450 enzymes (Kronbach et al., Anal. Biochem., 1987 April, 162 (1):24-32; and Dayer et al., Clin. Pharmacol. Ther., 1989 January, 45(1):34-40). In addition to metabolizing dextromethorphan, the P450 2D6 isozyme also oxidizes sparteine and debrisoquine. It is known that the P450 2D6 enzyme can be inhibited by a number of drugs, particularly quinidine (Brinn et al., Br. J. Clin. Pharmacol., 1986 August, 22(2):194-7; Inaba et al., Br. J. Clin. Pharmacol., 1986 August, 22(2):199-200; Brosen et al., Pharmacol. Toxicol., 1987 April, 60(4):312-4; Otton et al., Drug Metab. Dispos., 1988 January-February, 16(1):15-7; Otton et al., J. Pharmacol. Exp. Ther., 1988 October, 247(1):242-7; Funck-Brentano et al., Br. J. Clin. Pharmacol., 1989 April, 27(4):435-44; Funck-Brentano et al., J. Pharmacol. Exp. Ther., 1989 April, 249(1):134-42; Nielsen et al., Br. J. Clin. Pharmacol., 1990 March, 29(3):299-304; Broly et al., Br. J. Clin. Pharmacol., 1989 July, 28(1):29-36).

Patients who lack the normal levels of P450 2D6 activity are classified in the medical literature as "poor metabolizers," and doctors are generally warned to be cautious about administering various drugs to such patients. "The diminished oxidative biotransformation of these compounds in the poor metabolizer (PM) population can lead to excessive drug accumulation, increased peak drug levels, or in some cases, decreased generation of active metabolites . . . Patients with the PM phenotype are at increased risk of potentially serious untoward effects . . . " (Guttendorf et al., Ther. Drug Monit., 1988, 10(4):490-8, page 490). Accordingly, doctors are cautious about administering quinidine to patients, and rather than using drugs such as quinidine to inhibit the rapid elimination of dextromethorphan, researchers working in this field have administered very large quantities (such as 750 mg/day) of dextromethorphan to their patients, even though this is known to introduce various problems (Walker et al., Clin Neuropharmacol., 1989 August, 12(4):322-30; and Albers et al., Stroke, 1991 August, 22(8):1075-7).

Dextromethorphan is a weak, noncompetitive NMDA receptor antagonist that binds with moderate-to-high affinity to the phencyclidine site of the receptor complex. However, DM has additional, unique pharmacological properties. Binding studies suggest it is a ligand at the high affinity sigma 1 site, where it initially was proposed to act as an antagonist (Tortella et al., TiPS, 1989; 10:501-7) but more recently as an agonist (Maurice et al., Brain Res. Brain Res. Rev., 2001; 37:116-32). Sigma ligands also modulate NMDA responses (Debonnel et al., Life Sci., 1996; 58:721-34). Due to its inhibitory actions on glutamate, a number of investigators have treated ALS patients with DM in the hope of modifying or arresting the disease (Askmark et al., J. Neurol. Neurosurg. Psychiatry, 1993; 56:197-200; Hollander et al., Ann. Neurol., 1994; 36:920-4; and Blin et al., Clin. Neuropharmacol., 1996; 19:189-92). These trials have failed to demonstrate any benefit, possibly due to the rapid and extensive metabolism of DM that occurs in approximately 90 percent of the Caucasian population (referred to as extensive metabolizers) (see Hildebrand et al., Eur. J. Clin. Pharmacol., 1989; 36:315-8).

DM metabolism is primarily mediated by CYP2D6 in extensive metabolizers. This can be circumvented by co-administration of quinidine, a selective CYP2D6 inhibitor, at Q doses 1 to 1.5 logs below those employed for the treatment of cardiac arrhythmias (Schadel et al., J. Clin. Psychopharmacol., 1995; 15:263-9). Blood levels of DM increase linearly with DM dose following co-administration with Q but are undetectable in most subjects given DM alone, even at high doses (Zhang et al., Clin. Pharmac. & Therap., 1992; 51:647-55). The observed plasma levels in these individuals thus mimic the plasma levels observed in individuals expressing the minority phenotype where polymorphisms in the gene result in reduced levels of P450 2D6 (poor metabolizers). Unexpectedly, during a study of DM and Q in ALS patients, patients reported that their emotional lability improved during treatment. Subsequently, in a placebo controlled crossover study (N=12) conducted to investigate this, the concomitant administration of DM and Q administered to ALS patients was found to suppress emotional lability ($P<0.001$ compared to placebo) (Smith et al., Neurology, 1995; 45:A330).

Rapid dextromethorphan elimination may be overcome by co-administration of quinidine along with dextromethorphan (U.S. Pat. No. 5,206,248 to Smith). The chemical structure of quinidine is as follows:

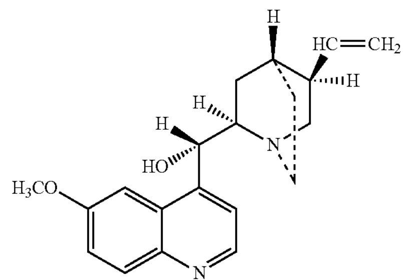

Quinidine co-administration has at least two distinct beneficial effects. First, it greatly increases the quantity of dextromethorphan circulating in the blood. In addition, it also yields more consistent and predictable dextromethorphan concentrations. Research involving dextromethorphan or co-administration of quinidine and dextromethorphan, and the effects of quinidine on blood plasma concentrations, are described in the patent literature (U.S. Pat. No. 5,166,207, U.S. Pat. No. 5,863,927, U.S. Pat. No. 5,366,980, U.S. Pat. No. 5,206,248, and U.S. Pat. No. 5,350,756 to Smith).

The discovery that dextromethorphan can reduce the internal feelings and external symptoms of emotional lability or pseudobulbar affect in some patients suffering from progressive neurological disease suggests that dextromethorphan is also likely to be useful for helping some patients suffering from emotional lability due to other causes, such as stroke or other ischemic (low blood flow) or hypoxic (low oxygen supply) events which led to neuronal death or damage in limited regions of the brain, or head injury or trauma as might occur during an automobile, motorcycle, or bicycling accident or due to a gunshot wound.

In addition, the results obtained to date also suggest that dextromethorphan is likely to be useful for treating some cases of emotional lability which are due to administration of other drugs. For example, various steroids, such as prednisone, are widely used to treat autoimmune diseases such as lupus. However, prednisone has adverse events on the emotional state of many patients, ranging from mild but noticeably increased levels of moodiness and depression, up to severely aggravated levels of emotional lability that can impair the business, family, or personal affairs of the patient.

In addition, dextromethorphan in combination with quinidine can reduce the external displays or the internal feelings that are caused by or which accompany various other problems such as "premenstrual syndrome" (PMS), Tourette's syndrome, and the outburst displays that occur in people suffering from certain types of mental illness. Although such problems may not be clinically regarded as emotional lability, they involve manifestations that appear to be sufficiently similar to emotional lability to suggest that dextromethorphan can offer an effective treatment for at least some patients suffering from such problems.

One of the significant characteristics of the treatments of preferred embodiments is that the treatments function to reduce emotional lability without tranquilizing or otherwise significantly interfering with consciousness or alertness in the patient. As used herein, "significant interference" refers to adverse events that would be significant either on a clinical level (they would provoke a specific concern in a doctor or psychologist) or on a personal or social level (such as by causing drowsiness sufficiently severe that it would impair someone's ability to drive an automobile). In contrast, the types of very minor side effects that can be caused by an over-the-counter drug such as a dextromethorphan-containing cough syrup when used at recommended dosages are not regarded as significant interference.

The magnitude of a prophylactic or therapeutic dose of dextromethorphan in combination with quinidine in the acute or chronic management of emotional lability or other chronic conditions can vary with the particular cause of the condition, the severity of the condition, and the route of administration. The dose and/or the dose frequency can also vary according to the age, body weight, and response of the individual patient.

In general, it is preferred to administer the dextromethorphan and quinidine in a combined dose, or in separate doses administered substantially simultaneously. The preferred weight ratio of dextromethorphan to quinidine is about 1:1.5 or less, preferably about 1:1.45, 1:1.4, 1:1.35, or 1:1.3 or less, more preferably about 1:1.25, 1:1.2, 1:1.15, 1:1.1, 1:1.05, 1:1, 1:0.95, 1:0.9, 1:0.85, 1:0.8, 1:0.75, 1:0.7, 1:0.65, 1:0.6, 1:0.55 or 1:0.5 or less. In certain embodiments, however, dosages wherein the weight ratio of dextromethorphan to quinidine is greater than about 1:1.5 may be preferred, for example, dosages of about 1:1.6, 1:1.7, 1:1.8, 1:1.9, 1:2 or greater. Likewise, in certain embodiments, dosages wherein the ratio of dextromethorphan to quinidine is less than about 1:0.5 may be preferred, for example, about 1:0.45, 1:0.4, 1:0.35, 1:0.3, 1:0.25, 1:0.2, 1:0.15, or 1:0.1 or less. When dextromethorphan and quinidine are administered at the preferred ratio of 1:1.25 or less, it is generally preferred that less than 50 mg quinidine is administered at any one time, more preferably about 45, 40, or 35 mg or less, and most preferably about 30, 25, or 20 mg or less. It may also be preferred to administer the combined dose (or separate doses simultaneously administered) at the preferred ratio of 1:1.25 or less twice daily, three times daily, four times daily, or more frequently so as to provide the patient with a preferred dosage level per day, for example: 60 mg quinidine and 60 mg dextromethorphan per day provided in two doses, each dose containing 30 mg quinidine and 30 mg dextromethorphan; 50 mg quinidine and 50 mg dextromethorphan per day provided in two doses, each dose containing 25 mg quinidine and 25 mg dextromethorphan; 40 mg quinidine and 40 mg dextromethorphan per day provided in two doses, each dose containing 20 mg quinidine and 20 mg dextromethorphan; 30 mg quinidine and 30 mg dextromethorphan per day provided in two doses, each dose containing 15 mg quinidine and 15 mg dextromethorphan; or 20 mg quinidine and 20 mg dextromethorphan per day provided in two doses, each dose containing 10 mg quinidine and 10 mg dextromethorphan. The total amount of dextromethorphan and quinidine in a combined dose may be adjusted, depending upon the number of doses to be administered per day, so as to provide a suitable daily total dosage to the patient, while maintaining the preferred ratio of 1:1.25 or less. These ratios are particularly preferred for the treatment of emotional lability and neuropathic pain.

In general, the total daily dose for dextromethorphan in combination with quinidine, for the conditions described herein, is about 10 mg or less up to about 200 mg or more dextromethorphan in combination with about 1 mg or less up to about 150 mg or more quinidine; preferably from about 15 or 20 mg to about 65, 70, 75, 80, 85, 90, 95, 100, 110, 120, 130, 140, 150, 160, 170, 180, or 190 mg dextromethorphan in combination with from about 2.5, 5, 7.5, 10, 15, or 20 mg to about 55, 60, 65, 70, 75, 80, 85, 90, 95, 100, 110, 120, 130, or 140 mg quinidine; more preferably from about 25, 30, 35, or 40 mg to about 55 or 60 mg dextromethorphan in combination with from about 25, 30, or 35 mg to about 40, 45, or 50 mg quinidine. In particularly preferred embodiments, the daily dose of dextromethorphan (DM) to quinidine (Q) is: 20 mg DM to 20 mg Q; 20 mg DM to 30 mg Q; 20 mg DM to 40 mg Q; 20 mg DM to 50 mg Q; 20 mg DM to 60 mg Q; 30 mg DM to 20 mg Q; 30 mg DM to 30 mg Q; 30 mg DM to 40 mg Q; 30 mg DM to 50 mg Q; 30 mg DM to 60 mg Q; 40 mg DM to 20 mg Q; 40 mg DM to 30 mg Q; 40 mg DM to 40 mg Q; 40 mg DM to 50 mg Q; 40 mg DM to 60 mg Q; 50 mg DM to 20 mg Q; 50 mg DM to 30 mg Q; 50 mg DM to 40 mg Q; 50 mg DM to 50 mg Q; 50 mg DM to 50 mg Q; 60 mg DM to 20 mg Q; 60 mg DM to 30 mg Q; 60 mg DM to 40 mg Q; 60 mg DM to 50 mg Q; or 60 mg DM to 60 mg Q. A single dose per day or divided doses (two, three, four or more doses per day) can be administered.

Preferably, a daily dose for emotional lability is about 20 mg to about 60 mg dextromethorphan in combination with about 20 mg to about 60 mg quinidine, in single or divided doses. Particularly preferred daily dose for emotional lability is about 20, 21, 22, 23, 24, 25, 26, 27, 28, 29, or 30 mg dextromethorphan in combination with about 20, 21, 22, 23, 24, 25, 26, 27, 28, 29, or 30 mg quinidine; about 30, 31, 32, 33, 34, 35, 36, 37, 38, 39, or 40 mg dextromethorphan in combination with about 20, 21, 22, 23, 24, 25, 26, 27, 28, 29, or 30 mg quinidine; about 40, 41, 42, 43, 44, 45, 46, 47, 48, 49, or 50 mg dextromethorphan in combination with about 20, 21, 22, 23, 24, 25, 26, 27, 28, 29, or 30 mg quinidine; or about 50, 51, 52, 53, 54, 55, 56, 57, 58, 59, or 60 mg dextromethorphan in combination with about 20, 21, 22, 23, 24, 25, 26, 27, 28, 29, or 30 mg quinidine; in single or divided doses.

In general, the total daily dose for dextromethorphan in combination with quinidine, for chronic pain, such as neuropathic pain, intractable coughing, dermatitis, tinnitus, and sexual dysfunction is preferably about 10 mg or less up to about 200 mg or more dextromethorphan in combination with about 1 mg or less up to about 150 mg or more quinidine. Particularly preferred total daily dosages for chronic pain, such as neuropathic pain, intractable coughing, dermatitis, tinnitus, and sexual dysfunction are about 20, 21, 22, 23, 24, 25, 26, 27, 28, 29, or 30 mg dextromethorphan in combination with about 20, 21, 22, 23, 24, 25, 26, 27, 28, 29, or 30 mg quinidine; about 30, 31, 32, 33, 34, 35, 36, 37, 38, 39, or 40 mg dextromethorphan in combination with about 20, 21, 22, 23, 24, 25, 26, 27, 28, 29, or 30 mg quinidine; about 40, 41, 42, 43, 44, 45, 46, 47, 48, 49, or 50 mg dextromethorphan in combination with about 20, 21, 22, 23, 24, 25, 26, 27, 28, 29, or 30 mg quinidine; or about 50, 51, 52, 53, 54, 55, 56, 57, 58, 59, or 60 mg dextromethorphan in combination with about 20, 21, 22, 23, 24, 25, 26, 27, 28, 29, or 30 mg quinidine; in single or divided doses. Similar daily doses for other indications as mentioned herein are generally preferred.

In managing treatment, the therapy is preferably initiated at a lower daily dose, preferably about 20 or 30 mg dextromethorphan in combination with about 2.5 mg quinidine per day, and increased up to about 60 mg dextromethorphan in combination with about 75 mg quinidine, or higher, depending on the patient's global response. It is further preferred that infants, children, patients over 65 years, and those with impaired renal or hepatic function, initially receive low doses, and that they be titrated based on individual response(s) and blood level(s). Generally, a daily dosage of 20 to 30 mg dextromethorphan and 20 to 30 mg quinidine is well-tolerated by most patients.

It can be preferred to administer dosages outside of these preferred ranges in some cases, as will be apparent to those skilled in the art. Further, it is noted that the ordinary skilled clinician or treating physician will know how and when to interrupt, adjust, or terminate therapy in consideration of individual patient response.

Any suitable route of administration can be employed for providing the patient with an effective dosage of dextromethorphan in combination with quinidine. For example, oral, rectal, transdermal, parenteral (subcutaneous, intramuscular, intravenous), intrathecal, topical, inhalable, and like forms of administration can be employed. Suitable dosage forms include tablets, troches, dispersions, suspensions, solutions, capsules, patches, and the like. Administration of medicaments prepared from the compounds described herein can be by any suitable method capable of introducing the compounds into the bloodstream. Formulations of preferred embodiments can contain a mixture of active compounds with pharmaceutically acceptable carriers or diluents as are known by those of skill in the art.

The present method of treatment of emotional lability can be enhanced by the use of dextromethorphan in combination with quinidine as an adjuvant to known therapeutic agents, such as fluoxetine hydrochloride, marketed as PROZAC® by Eli Lilly and Company, and the like. Preferred adjuvants include pharmaceutical compositions conventionally employed in the treatment of the disordered as discussed herein.

The pharmaceutical compositions of the present invention comprise dextromethorphan in combination with quinidine, or pharmaceutically acceptable salts of dextromethorphan and/or quinidine, as the active ingredient and can also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of dextromethorphan and/or quinidine can also be suitable for use in compositions and methods of preferred embodiments. In particularly preferred embodiments, the dextromethorphan is administered in the form of dextromethorphan hydrobromide, and the quinidine is administered in the form of quinidine sulfate. For example, a dose of 30 mg dextromethorphan hydrobromide (of molecular formula $C_{18}H_{25}NO.HBr.H_2O$) and 30 quinidine sulfate (of molecular formula $(C_{20}H_{24}N_2O_2)_2.H_2SO_4.2H_2O$) may be administered (corresponding to an effective dosage of approximately 22 mg dextromethorphan and 25 mg quinidine). Other preferred dosages include, for example, 45 mg dextromethorphan hydrobromide and 30 quinidine sulfate (corresponding to an effective dosage of approximately 33 mg dextromethorphan and approximately 25 mg quinidine); 60 mg dextromethorphan hydrobromide and 30 quinidine sulfate (corresponding to an effective dosage of approximately 44 mg dextromethorphan and approximately 25 mg quinidine); 45 mg dextromethorphan hydrobromide and 45 quinidine sulfate (corresponding to an effective dosage of approximately 33 mg dextromethorphan and 37.5 mg quinidine); 60 mg dextromethorphan hydrobromide and 60 quinidine sulfate (corresponding to an effective dosage of approximately 44 mg dextromethorphan and 50 mg quinidine).

The compositions can be prepared in any desired form, for example, tables, powders, capsules, suspensions, solutions, elixirs, and aerosols. Carriers such as starches, sugars, microcrystalline cellulose, diluents, granulating agents, lubricants, binders, disintegrating agents, and the like can be used in oral solid preparations. Oral solid preparations (such as powders, capsules, and tablets) are generally preferred over oral liquid preparations. However, in certain embodiments oral liquid preparations can be preferred over oral solid preparations. The most preferred oral solid preparations are tablets. If desired, tablets can be coated by standard aqueous or non-aqueous techniques.

In addition to the common dosage forms set out above, the compounds can also be administered by sustained release, delayed release, or controlled release compositions and/or delivery devices, for example, such as those described in U.S. Pat. Nos. 3,845,770; 3,916,899; 3,536,809; 3,598,123; and 4,008,719.

Pharmaceutical compositions suitable for oral administration can be provided as discrete units such as capsules, cachets, tablets, and aerosol sprays, each containing predetermined amounts of the active ingredients, as powder or granules, or as a solution or a suspension in an aqueous liquid, a non-aqueous liquid, an oil-in-water emulsion, or a water-in-oil liquid emulsion. Such compositions can be prepared by any of the conventional methods of pharmacy, but the majority of the methods typically include the step of bringing into association the active ingredients with a carrier which constitutes one or more ingredients. In general, the compositions are prepared by uniformly and intimately admixing the active ingredients with liquid carriers, finely divided solid carriers, or both, and then, optionally, shaping the product into the desired presentation.

For example, a tablet can be prepared by compression or molding, optionally, with one or more additional ingredients. Compressed tablets can be prepared by compressing in a suitable machine the active ingredient in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

Preferably, each tablet contains from about 30 mg to about 60 mg of dextromethorphan and from about 30 mg to about 45 mg quinidine, and each capsule contains from about 30 mg to about 60 mg of dextromethorphan and from about 30 mg to about 45 mg quinidine. Most preferably, tablets or capsules are provided in a range of dosages to permit divided dosages to be administered. For example, tablets, cachets or capsules can be provided that contain about 10 mg dextromethorphan and about 5, 10, or 15 mg quinidine; about 20 mg dextromethorphan and about 10, 20 or 30 mg quinidine; about 30 mg dextromethorphan and about 15, 30, or 45 mg quinidine;

and the like. A dosage appropriate to the patient, the condition to be treated, and the number of doses to be administered daily can thus be conveniently selected. While it is generally preferred to incorporate both dextromethorphan and quinidine in a single tablet or other dosage form, in certain embodiments it can be desirable to provide the dextromethorphan and quinidine in separate dosage forms.

It has been unexpectedly discovered that patients suffering from emotional lability and other conditions as described herein can treated with dextromethorphan in combination with an amount of quinidine substantially lower than the minimum amount heretofore believed to be necessary to provide a significant therapeutic effect. As used herein, a "minimum effective therapeutic amount" is that amount which provides a satisfactory degree of inhibition of the rapid elimination of dextromethorphan from the body, while producing no adverse effect or only adverse events of an acceptable degree and nature. More specifically, a preferred effective therapeutic amount is within the range of from about 20, 25 or 30 mg to about 60 mg of dextromethorphan and less than about 50 mg of quinidine per day, preferably about 20 or 30 mg to about 60 mg of dextromethorphan and about 30 mg to about 45 mg of quinidine per day, the amount being preferably administered in a divided dose based on the plasma half-life of dextromethorphan. For example, in a preferred embodiment dextromethorphan and quinidine are administered in specified mg increments to achieve a target concentration of dextromethorphan of a specified level in μg/mL plasma, with a maximum preferred specified dosage of dextromethorphan and quinidine based on body weight. The target dose is then preferably administered every 12 hours. Since the level of quinidine is minimized, the side effects observed at high dosages for quinidine are minimized or eliminated, a significant benefit over compositions containing dextromethorphan in combination with higher levels of quinidine.

The combination of dextromethorphan and quinidine of preferred embodiments can also be extremely effective in formulations for the treatment for other chronic disorders which do not respond well to other treatments. Dextromethorphan in combination with quinidine can be used to effectively treat severe or intractable coughing, which has not responded adequately to non-addictive, non-steroid medications, with minimal side-effects. Intractable coughing is a consequence of respiratory infections, asthma, emphysema, and other conditions affecting the pulmonary system.

Dextromethorphan in combination with quinidine as in the preferred embodiments can also be used in pharmaceutical compositions for treating dermatitis. As used herein, "dermatitis" or "eczema" is a skin condition characterized by visible skin lesions and/or an itching or burning sensation on the skin. Dextromethorphan in combination with quinidine as in the preferred embodiments can also be used in pharmaceutical compositions for the treatment of chronic pain from conditions such as stroke, trauma, cancer, and pain due to neuropathies such as herpes zoster infections and diabetes. Other conditions that can be treated using dextromethorphan in combination with quinidine according to the preferred embodiments can include sexual dysfunctions, such as priapism or premature ejaculation, as well as tinnitus.

Clinical Study #1

Clinical testing was conducted to determine the lowest dose of quinidine which inhibits the conversion of dextromethorphan to dextrorphan; and to chronicle the occurrence of side effects during administration of dextromethorphan/quinidine.

Testing protocol specifications and a detailed time and events schedule were prepared to assure consistent execution of the protocol throughout the study conduct.

A phenotyping study directed to dextromethorphan was conducted. The study was an open-label single dose study. Subjects were screened to ensure they met the inclusion and exclusion criteria. Subjects received a single oral dose of dextromethorphan hydrobromide 30 mg capsule taken with 240 mL of tap water. A total of fifty-eight subjects were screened and fifty subjects dosed. The study determined each subject's ability to metabolize dextromethorphan. Subjects who met the inclusion/exclusion criteria remained in house for dosing. Each subject was administered one 30 mg capsule (P.M.) of dextromethorphan. Urine was collected predose through 12 hours postdose and analyzed for dextromethorphan and dextrorphan. A blood sample (5 mL) was collected for analysis of plasma dextromethorphan, dextrorphan, and quinidine predose and at 2, 4 and 8 hours postdose. Following a wash-out period of at least two days, forty-eight subjects determined to be extensive metabolizers of dextromethorphan were asked to participate in the quinidine dosing study. Forty-six of these subjects were determined to be extensive metabolizers of dextromethorphan. One adverse effect was reported during the study (a headache, classified as mild, that resolved without intervention).

Thereafter, a quinidine dose determination study was conducted. The study was an open-label, randomized, multiple dose study. Subjects identified as extensive metabolizers received an evening dose on Day 1, at 12-hour intervals for the next six days, with a final morning dose on Day 8. All subjects were instructed to dose themselves at home on eight occasions with medication dispensed to them. Subjects maintained a diary during the study to record adverse effects.

Subjects randomized to Treatment A received fourteen oral doses of dextromethorphan hydrobromide 30 mg capsule taken with 240 mL of tap water. Subjects randomized to Treatment B received fourteen oral doses of dextromethorphan hydrobromide 30 mg/quinidine 2.5 mg capsule taken with 240 mL of tap water. Subjects randomized to Treatment C received fourteen oral doses of dextromethorphan hydrobromide 30 mg/quinidine 10 mg capsule taken with 240 mL of tap water. Subjects randomized to Treatment D received fourteen oral doses of dextromethorphan Hydrobromide 30 mg/quinidine 25 mg capsule taken with 240 mL of tap water. Subjects randomized to Treatment E received fourteen oral doses of dextromethorphan hydrobromide 30 mg/quinidine 50 mg capsule taken with 240 mL of tap water. Subjects randomized to Treatment F received fourteen oral doses of dextromethorphan hydrobromide 30 mg/quinidine 75 mg capsule taken with 240 mL of tap water.

All subjects enrolled in the study except for one satisfied the inclusion/exclusion criteria as listed in the protocol. Medical histories, clinical laboratory evaluations, and performed physical examinations were reviewed prior to subjects being enrolled in the study. The subjects were instructed not to consume any grapefruit products while participating in the study. Over-the-counter medications were prohibited three days prior to dosing and during the study, and prescription medications (with the exception of oral contraceptives) were prohibited fourteen days prior to dosing and during the study.

A total of forty-six subjects, twenty-two males and twenty-four females, were enrolled in the study and forty-five subjects, twenty-two males and twenty-three females, completed the study. The subjects were screened within twenty-one days prior to study enrollment. The screening procedure included medical history, physical examination (height, weight, frame size, vital signs, and ECG), and clinical laboratory tests (hematology, serum chemistry, urinalysis, HIV antibody screen, serum pregnancy, and a screen for THECA).

Subjects were dosed in the clinic on the following schedule: Day 1 (P.M.), Day 2 (A.M.), Day 3 (P.M.), Day 4 (A.M.) and Day 7 (P.M.). The subjects reported to the clinic on Day 8 for the A.M. dosing and remained in house for 8 hours postdose. Subjects self medicated at home on Day 2 (P.M.), Day 3 (A.M.), Day 4 (P.M.), Day 5 (A.M. and P.M.), Day 6 (A.M. and P.M.), and Day 7 (A.M.). Subjects were dosed twice daily except they received only a PM dose on Day 1 and an AM dose on Day 8.

A clinical laboratory evaluation (hematology, chemistries, urinalysis), vital signs, ECG, and a brief physical examination were performed at the completion of the study. Subjects were instructed to inform the study physician and/or safety nurses of any adverse events that occurred during the study.

Blood samples (5 mL) were collected on Day 8 prior to dosing and at 2, 4 and 8 hours postdose for analysis of dextromethorphan, dextrorphan, and quinidine. A total of eight blood samples (40 mL) were drawn during the study (including the dextromethorphan screen) for drug analysis. Plasma samples were separated by centrifugation and then frozen at −20° C. and kept frozen until assayed. Urine was collected predose through twelve hours post doses 1, 5, and 13. Urine samples were pooled for the entire collection interval. At the end of the interval, the total volume was recorded and two aliquots were frozen at −20° C. until assayed for dextromethorphan and dextrorphan.

A total of forty-six subjects were dosed and forty-five subjects completed the study. One subject was discontinued/withdrawn from the study as not tolerating adverse events experienced. The mean age of the subjects was 51 years (range of 20 through 86), the mean height of the subjects was 67.6 inches (range of 61.5 through 74.5), and the mean weight of the subjects was 162.9 pounds (range 101.0 through 229.0).

A total of eight subjects were enrolled in Treatment Groups B, D, and E. Seven subjects were enrolled in Treatment Groups A and C.

A total of 150 adverse events were experienced by thirty-four subjects (74%). Other than one serious adverse effect, all adverse events were classified as mild (96%) or moderate (4%). The most frequently reported adverse events included headache, loose stool, lightheadedness, dizziness, and nausea. The relationship to study drug was classified as possibly, probably, or almost certainly for 120 of the 150 adverse events (80%). There were no clear differences between dose groups in the type or frequency of adverse events observed. No clinically significant trends regarding vital signs, physical examinations or clinical laboratory tests were observed.

Clinical Study #2

The objectives of this study were to determine pharmacokinetic parameters of dextromethorphan upon single-dose and multiple-doses of a capsule formulation containing 30 mg dextromethorphan hydrobromide and 25 mg quinidine sulfate capsules, to determine the differences in these pharmacokinetic parameters for extensive metabolizers and poor metabolizers, and to chronicle the occurrence of side effects during administration of the formulation. This study had an open-label, single, and multiple dose design.

Ten subjects were enrolled in the study. A total of nine subjects completed the study. Ten subjects were included in safety analyses, and nine were included in pharmacokinetic analyses. All subjects enrolled in this study were judged by the investigator to be normal, healthy volunteers.

The test formulation was 30 mg dextromethorphan hydrobromide and 25 mg quinidine sulfate capsules. All subjects received one 30 mg dextromethorphan hydrobromide and 25 mg quinidine sulfate capsule taken orally with 240 mL of water every 12 hours for a total of 15 doses.

The noncompartmental pharmacokinetic parameters Cmax, Tmax, and AUC (0-12) were calculated from the plasma concentration-time data for dextromethorphan, dextrorphan, and quinidine on Days 1, 4, and 8. In addition, the parameters Kel and T ½el were calculated for dextrorphan (Day 8), and quinidine (Days 1, 4, and 8).

The amount of dextromethorphan and dextrorphan excreted in the urine was calculated from the 12-hour urine collections on Day 1 (postdose 1), Day 8 (postdose 15), and Days 9-14. The molar metabolic ratio (dextromethorphan: dextrorphan) was calculated for each urine-collection day.

Subjects were evaluated by physical examination, vital signs, electrocardiogram (ECG), clinical laboratory (hematology, serum chemistry, and urinalysis), and adverse event assessment.

Descriptive statistics for each parameter, including mean, median, standard deviation, coefficient of variation, N, minimum, and maximum were calculated for all of the subjects by Day. In addition, descriptive statistics were presented by the subgroups: extensive metabolizer (EM) and poor metabolizer (PM).

A normal theory, general linear model (GLM) was applied to the log-transformed parameters Cmax and AUC (0-12), and untransformed Tmax (dextromethorphan and dextrorphan), and to untransformed parameters Cmax, AUC (0-12), and Tmax (quinidine). The ANOVA model included the factors group (EM or PM), subject within group, day, and the interaction term day by group. The group effect was tested using the subject within group mean square, and all other main effects were tested using the residual error (error mean square). In addition, tests of the hypotheses Day 1=Day 4, Day 1=Day 8, and Day 4=Day 8 were performed.

Safety and tolerability were assessed via data listings and calculation of summary statistics as follows: hematology, serum chemistry, and urinalysis test results from predose and postdose were listed in by-subject data listings. Descriptive statistics were reported by time point of collection, and changes from predose to postdose were summarized and statistically tested using the paired t-test ($H_o$: change=0). Shift tables describing out-of-range shifts from predose to postdose were created. Out-of-normal range and clinically significant laboratory values were listed by subject.

Descriptive statistics (mean, standard deviation, minimum, maximum, and sample size) were reported by time point (screen and Day 8 postdose) for vital sign measurements: systolic and diastolic blood pressure, pulse rate, respiration and temperature. Summary statistics were presented by metabolizer type. Differences between screening and postdose measurements were presented and statistically tested using a paired t-test ($H_o$: difference=0). Individual vital signs results were listed in by-subject data listings. Changes in physical examination results that occurred from predose to postdose were also identified.

Twelve-lead ECGs were recorded prior to dosing. Descriptive statistics (mean, standard deviation, minimum, maximum, and sample size) were reported by time point (predose and Day 8 postdose) for ECG measurements: QRS, PR, QTc, and heart rate. Summary statistics were presented by metabolizer type. Differences between predose and Day 8 postdose measurements were presented and statistically testing using a paired t-test ($H_o$: difference=0). ECG results were listed in by-subject data listings.

Adverse events were classified using the 5th Edition of the COSTART dictionary. Summary tables include number of subjects reporting the adverse event and as percent of number of subjects dosed by metabolizer type. Summary tables were also presented by adverse event frequency, severity, and relationship to study medication. Adverse events were listed by subject, including verbatim term, severity, frequency, and relationship to treatment in data listings.

Mean pharmacokinetic parameters for dextromethorphan, dextrorphan, and quinidine are summarized in Table 1 for extensive metabolizers of dextromethorphan (EMs), poor metabolizers of dextromethorphan (PMs), and all subjects.

TABLE 1

| | Pharmaco- | | Metabolizer Type | | | | | | | | |
|---|---|---|---|---|---|---|---|---|---|---|---|
| | kinetics | | EM | | | PM | | | All Subjects | | |
| Compound | Parameter | Day | Mean | N | S.D. | Mean | N | S.D. | Mean | N | S.D. |
| Dextrome-thorphan | Cmax (ng/mL) | 1 | 15.89 | 7 | 8.22 | 22.30 | 2 | 0.14 | 17.31 | 9 | 7.66 |
| | | 4 | 76.69 | 7 | 15.28 | 105.70 | 2 | 9.48 | 83.13 | 9 | 18.71 |
| | | 8 | 95.50 | 7 | 19.92 | 136.20 | 2 | 3.25 | 104.54 | 9 | 24.92 |
| | Tmax (hr) | 1 | 6.85 | 7 | 2.78 | 8.00 | 2 | 0.00 | 7.11 | 9 | 2.46 |
| | | 4 | 5.42 | 7 | 1.90 | 6.00 | 2 | 2.82 | 5.55 | 9 | 1.94 |
| | | 8 | 5.99 | 7 | 2.58 | 4.99 | 2 | 1.41 | 5.77 | 9 | 2.33 |
| | AUC (0-12) (ng*hr./ml) | 1 | 133.27 | 7 | 59.86 | 198.33 | 2 | 6.97 | 147.73 | 9 | 59.30 |
| | | 4 | 811.68 | 7 | 151.7 | 1146.4 | 2 | 84.43 | 886.07 | 9 | 199.8 |
| | | 8 | 1049.0 | 7 | 243.3 | 1533.5 | 2 | 80.97 | 1156.7 | 9 | 301.4 |
| | T ½el (hr) | 8 | 13.13 | 6 | 3.41 | 41.96 | 2 | 4.47 | 20.33 | 8 | 13.76 |
| Dextrorphan | Cmax (ng/ml) | 1 | 124.86 | 7 | 53.26 | 10.80 | 2 | 3.39 | 99.51 | 9 | 68.25 |
| | | 4 | 79.33 | 7 | 18.63 | 37.05 | 2 | 0.21 | 69.93 | 9 | 24.65 |
| | | 8 | 123.51 | 7 | 17.07 | 51.45 | 2 | 4.17 | 107.50 | 9 | 35.08 |
| | Tmax (hr) | 1 | 4.00 | 7 | 0.00 | 3.00 | 2 | 1.42 | 3.78 | 9 | 0.67 |
| | | 4 | 2.21 | 7 | 1.40 | 2.00 | 2 | 0.00 | 2.17 | 9 | 1.22 |
| | | 8 | 41.18 | 7 | 11.57 | 2.99 | 2 | 1.41 | 32.70 | 9 | 19.61 |
| | AUC (0-12) (ng*hr/mL) | 1 | 933.83 | 7 | 324.8 | 90.95 | 2 | 19.08 | 748.52 | 9 | 466.2 |
| | | 4 | 849.22 | 7 | 181.9 | 365.27 | 2 | 30.37 | 741.68 | 9 | 265.4 |
| | | 8 | 1000.5 | 7 | 147.2 | 530.40 | 2 | 82.39 | 896.04 | 9 | 245.1 |
| Quinidine | Cmax (µg/ml) | 1 | 0.09 | 7 | 0.02 | 0.08 | 2 | 0.01 | 0.09 | 9 | 0.02 |
| | | 4 | 0.15 | 7 | 0.03 | 0.14 | 2 | 0.01 | 0.15 | 9 | 0.03 |
| | | 8 | 0.16 | 7 | 0.04 | 0.16 | 2 | 0.02 | 0.16 | 9 | 0.03 |
| | Tmax (hr) | 1 | 1.71 | 7 | 0.27 | 1.50 | 2 | 0.00 | 1.67 | 9 | 0.25 |
| | | 4 | 1.65 | 7 | 0.37 | 1.52 | 2 | 0.00 | 1.62 | 9 | 0.33 |
| | | 8 | 1.99 | 7 | 0.01 | 1.49 | 2 | 0.00 | 1.88 | 9 | 0.22 |
| | AUC (0-12) (µg*hr/mL) | 1 | 0.48 | 7 | 0.18 | 0.51 | 2 | 0.13 | 0.49 | 9 | 0.17 |
| | | 4 | 1.20 | 7 | 0.21 | 0.97 | 2 | 0.05 | 1.15 | 9 | 0.21 |
| | | 8 | 1.31 | 7 | 0.19 | 1.07 | 2 | 0.02 | 1.26 | 9 | 0.19 |
| | T ½el (hr) | 1 | 8.11 | 7 | 2.95 | 8.25 | 2 | 2.65 | 8.14 | 9 | 2.72 |
| | | 4 | 6.86 | 7 | 1.11 | 6.51 | 2 | 0.70 | 6.78 | 9 | 1.01 |
| | | 8 | 7.66 | 7 | 1.09 | 6.66 | 2 | 0.41 | 7.44 | 9 | 1.05 |

Mean urinary metabolic ratios (dextromethorphan:dextrorphan) are summarized in Table 2 for extensive metabolizers of dextromethorphan (EMs), poor metabolizers of dextromethorphan (PMs), and all subjects.

TABLE 2

| | Metabolizer Type | | | | | | | | |
|---|---|---|---|---|---|---|---|---|---|
| | EM | | | PM | | | All Subjects | | |
| Day | Mean | N | S.D. | Mean | N | S.D. | Mean | N | S.D. |
| 1 | 0.268 | 7 | 0.227 | 1.790 | 2 | 0.493 | 0.608 | 9 | 0.721 |
| 8 | 0.804 | 7 | 0.366 | 1.859 | 2 | 0.507 | 1.039 | 9 | 0.591 |
| 9 | 0.445 | 6 | 0.170 | 1.398 | 2 | 0.597 | 0.683 | 8 | 0.516 |
| 10 | 0.198 | 7 | 0.152 | 2.538 | 2 | 1.593 | 0.718 | 9 | 1.183 |
| 11 | 0.145 | 7 | 0.125 | 2.200 | 2 | 1.136 | 0.601 | 9 | 0.997 |
| 12 | 0.091 | 7 | 0.086 | 3.333 | 2 | 0.090 | 0.812 | 9 | 1.432 |
| 13 | 0.037 | 7 | 0.064 | 2.250 | 2 | 0.554 | 0.529 | 9 | 0.997 |
| 14 | 0.027 | 5 | 0.061 | 2.061 | 2 | 0.115 | 0.608 | 7 | 0.995 |

No serious adverse events occurred during this study. Drug related adverse events included asthenia, diarrhea, anorexia, nausea, vomiting, anxiety, depersonalization, insomnia, and somnolence. The majority of the adverse events were mild in severity and all were resolved without treatment. Prolonged QT intervals and decreased ventricular rates were observed for the extensive metabolizer group following dosing. No clinically significant trends regarding vital signs, physical examinations, or routine clinical laboratory tests were observed.

Over the course of this study, low dose quinidine inhibited the metabolism of dextromethorphan, resulting in increased systemic availability. This effect was most pronounced in extensive metabolizers. The mean urinary metabolic ratio (dextromethorphan:dextrorphan) increased at least 29-fold in extensive metabolizers by Day 8. The plasma dextrorphan AUC (0-12) increased approximately 8-fold between Day 1 and Day 8, whereas the mean plasma dextrorphan AUC (0-12) remained the same between Day 1 and Day 8.

The effect of quinidine on dextromethorphan metabolism in poor metabolizers was unclear. The urinary metabolic ratios did not appear to change with quinidine treatment. The excretion of both dextromethorphan and dextrorphan increased. However, dextrorphan excretion increased proportionally to dextromethorphan. This suggests that quinidine did not inhibit dextromethorphan metabolism to dextrorphan in poor metabolizers. However, there was 6.1-fold increase in dextromethorphan AUC (0-12) from Day 1 to Day 8, compared to a 4.8-fold increase in dextrorphan AUC (0-12), which is consistent with a small decrease in metabolic clearance.

Quinidine pharmacokinetics were similar between extensive metabolizers and poor metabolizers. Mean quinidine elimination half-life values (6.78 to 8.14 hours) were similar to previously reported values.

Dextromethorphan hydrobromide and quinidine sulfate capsules administered as a single-dose or multiple-doses product appeared to be well tolerated in this healthy population.

Clinical Study #3

The objectives of this study were to determine the lowest dose of quinidine sulfate that effectively inhibits the conversion of 45 mg of dextromethorphan to dextrorphan and the lowest dose of quinidine that effectively inhibits the conversion of 60 mg of dextromethorphan to dextrorphan, and to chronicle the occurrence of side effects during administration of dextromethorphan in combination with quinidine.

This dose interaction study was a Phase 1, open-label, parallel group, multiple-dose, single-center, safety, and pharmacokinetic study. A total of sixty-four subjects were planned, and sixty-five subjects were enrolled in the study. A total of forty-seven subjects completed the study and were included in pharmacokinetic analyses. All subjects were included in safety analyses. Males and females between 18 and 60 years of age, identified as extensive metabolizers of dextromethorphan, were enrolled. All subjects were judged to be healthy volunteers. Enrolled subjects met inclusion and exclusion criteria.

The test formulation was dextromethorphan hydrobromide and quinidine sulfate capsules, administered orally with water. Subjects receiving Treatment A received an oral dose of one dextromethorphan hydrobromide of 60 mg/0 mg quinidine sulfate capsule taken twice daily with 240 mL of water on Days 1 through 8. Subjects receiving Treatment B received an oral dose of one dextromethorphan hydrobromide of 60 mg/30 mg quinidine sulfate capsule taken twice daily with 240 mL of water on Days 1 through 8. Subjects receiving Treatment C received an oral dose of one dextromethorphan hydrobromide of 60 mg/45 mg quinidine sulfate capsule taken twice daily with 240 mL of water on Days 1 through 8. Subjects receiving Treatment D received an oral dose of one dextromethorphan hydrobromide of 60 mg/60 mg quinidine sulfate capsule taken twice daily with 240 mL of water on Days 1 through 8. Subjects receiving Treatment E received an oral dose of one dextromethorphan hydrobromide of 45 mg/0 mg quinidine sulfate capsule taken twice daily with 240 mL of water on Days 1 through 8. Subjects receiving Treatment F received an oral dose of one dextromethorphan hydrobromide of 45 mg/30 mg quinidine sulfate capsule taken twice daily with 240 mL of water on Days 1 through 8. Subjects receiving Treatment G received an oral dose of one dextromethorphan hydrobromide of 45 mg/45 mg quinidine sulfate capsule taken twice daily with 240 mL of water on Days 1 through 8. Subjects receiving Treatment H received an oral dose of one dextromethorphan hydrobromide of 45 mg/60 mg quinidine sulfate capsule taken twice daily with 240 mL of water on Days 1 through 8. For Treatments B, C, D, F, G, and H, subjects received a single dose of dextromethorphan hydrobromide (either 60 mg for Treatments B, C, and D or 45 mg for Treatments F, G, and H) without quinidine for the first dose and then 14 does of the designated capsule, i.e., all subjects received one dose of either Treatment A or E as a baseline.

The first dose of Treatments A and E was considered as reference. Dextromethorphan hydrobromide 30 mg capsules were used for phenotyping. Subjects received a single oral dose of one dextromethorphan hydrobromide 30 mg capsule taken with 240 mL of water.

The plasma pharmacokinetic parameters, Cmax, Tmax, AUC (0-5), and AUC (0-12) were calculated using noncompartmental analysis. Pharmacokinetic parameters were summarized and descriptive statistics for all groups were calculated. Changes in these parameters from baseline were calculated and summarized. Urine metabolic ratios (dextromethorphan/dextrorphan) were calculated. Descriptive statistics for all groups were calculated, and changes in metabolic ratio from baseline were calculated and summarized.

Adverse events assessments, monitoring of hematology, blood chemistry, and urine values, measurements of vital signs and electrocardiogram (ECG) as well as the performance of physical examinations were evaluated for safety.

The effect of quinidine on the pharmacokinetics of dextromethorphan was assessed by measuring serial plasma dextromethorphan and dextrorphan concentrations on Days 1 and 8, quinidine concentrations on Day 8, and the amount of dextromethorphan and dextrorphan excreted in the urine for 12-hour urine collections on Day, 1, Day 3, and Day 7, following a multiple dose administration of dextromethorphan and quinidine. The noncompartmental pharmacokinetic parameters Cmax, Tmax, AUC (0-5), and AUC (0-12) were calculated from the plasma concentration-time data for dextromethorphan and dextrorphan on Days 1 and 8, quinidine on Day 8. The amount of dextromethorphan and dextrorphan excreted in the urine was calculated from the 12-hour urine collections on Day 1, Day 3, and Day 7. The molar metabolic ratio (dextromethorphan: dextrorphan) was calculated for each urine-collection day. To assess the effect of quinidine on dextromethorphan, analysis of variance was performed using SAS PROC Mixed on the parameter AUC of dextromethorphan from the 4 dextromethorphan and quinidine treatments, respectively, for 60 mg and 45 mg dextromethorphan doses. Least square means of doses, the differences (pairwise comparisons) between doses, plus the P-values for the significance of the differences were presented. To assess the effect of dextromethorphan on quinidine, analysis of variance was performed using SAS PROC Mixed on the parameter AUC of quinidine. Least square means of doses, the differences (pairwise comparisons) between doses, plus the P-values for the significance of the differences were presented.

Safety and tolerability were assessed through calculation of summary statistics and were displayed in data listings of individual subjects. Adverse events were coded using the MedDRA Adverse Event Dictionary (Version 3.0, 2000). The frequency, type, severity, and relationship to study drug of treatment-emergent adverse events were displayed and compared across treatments.

For laboratory tests, the study screening and poststudy measurements, along with the change between these time points, were summarized by descriptive statistics (median, mean, standard deviation, minimum, maximum, and sample size) for serum chemistry and hematology tests. Shift tables from screening to poststudy for serum chemistry, hematology, and urinalysis laboratory tests were constructed. Out-of-range clinical laboratory results and their associated recheck values were listed.

Descriptive statistics (median, mean, standard deviation, minimum, maximum, and sample size) were calculated for vital signs and 12-lead electrocardiogram (ECG) measurements for baseline and postdose, along with the change between these time points. The ECG shift table from baseline to postdose was also presented.

The arithmetic means of pharmacokinetic parameters of plasma dextromethorphan, dextrorphan, and quinidine following Treatments A, B, C, D, E, F, G, and H, and results of statistical comparisons between treatment groups are presented in the following tables. Table 3 provides a summary of the plasma DM pharmacokinetic parameters following a 60 mg dose of dextromethorphan.

TABLE 3

| Pharmacokinetic | | Treatment A | | Treatment B | | Treatment C | | Treatment D | |
|---|---|---|---|---|---|---|---|---|---|
| Parameters | Day* | Mean | S.D. | Mean | S.D. | Mean | S.D. | Mean | S.D. |
| Cmax (ng/mL) | 1 | 3.7 | 3.70 | 2.1 | 2.82 | 3.5 | 3.19 | 4.8 | 4.74 |
| | 8 | 7.7 | 7.01 | 191.8 | 45.48 | 204.8 | 22.93 | 231.9 | 96.36 |
| | C | 4.0 | 4.75 | 189.7 | 43.90 | 201.3 | 22.19 | 227.1 | 97.52 |
| Tmax (hr) | 1 | 2.6 | 0.96 | 2.5 | 0.57 | 2.4 | 0.56 | 3.5 | 1.05 |
| | 8 | 2.1 | 0.38 | 3.5 | 1.73 | 3.7 | 1.17 | 5.2 | 1.94 |
| | C | −0.5 | 1.12 | 1.0 | 1.42 | 1.3 | 1.51 | 1.7 | 1.97 |
| AUC(0-t) | 1 | 23.0 | 23.64 | 12.1 | 16.04 | 20.7 | 17.39 | 32.0 | 34.66 |
| (ng*hr/mL) | 8 | 52.3 | 46.72 | 1963.0 | 608.50 | 2121.0 | 278.50 | 2252.0 | 689.30 |
| | C | 29.3 | 34.57 | 1951.0 | 600.30 | 2100.0 | 275.90 | 2220.0 | 697.70 |
| AUC (0-12) | 1 | 23.2 | 23.50 | 12.3 | 15.93 | 20.7 | 17.39 | 32.2 | 34.45 |
| (ng*hr/mL) | 8 | 52.3 | 46.72 | 1963.0 | 608.50 | 2121.0 | 278.50 | 2252.0 | 689.30 |
| | C | 29.2 | 34.79 | 1951.0 | 600.10 | 2100.0 | 275.90 | 2220.0 | 697.80 |
| 1n (Cmax) | 1 | 0.9 | 1.07 | 0.1 | 1.21 | 0.9 | 1.05 | 1.2 | 0.88 |
| | 8 | 1.6 | 1.03 | 5.2 | 0.24 | 5.3 | 0.11 | 5.4 | 0.40 |
| | C | 2.3 | 1.03 | 219.5 | 132.00 | 108.8 | 92.40 | 85.0 | 54.87 |
| In (AUC(0-12) | 1 | 2.7 | 1.07 | 2.0 | 1.08 | 2.8 | 0.95 | 3.1 | 0.98 |
| | 8 | 3.6 | 1.02 | 7.5 | 0.33 | 7.7 | 0.13 | 7.7 | 0.32 |
| | C | 2.6 | 1.22 | 324.9 | 185.30 | 170.9 | 130.30 | 141.0 | 114.80 |

*= Code C corresponds to the change from the baseline, calculated as follows: for the untransformed parameters, it is the difference between Day 8 and Baseline values, for the In-transformed parameters, it is the ratio of Day 8 over Baseline values.

Table 4 provides a summary of statistical comparisons of plasma dextromethorphan AUC (0-12) relating to the effect of quinidine doses on a 60 mg dose of dextromethorphan.

TABLE 4

| Treatment Comparison | Geometric | Means | Ratio of GEOMEANS | P |
|---|---|---|---|---|
| A vs. D | 35.11 | 2159.23 | 0.02 | 0.0001 |
| B vs. D | 1888.72 | 2159.23 | 0.87 | 0.7601 |
| C vs. D | 2108.96 | 2159.23 | 0.98 | 0.9608 |

Table 5 provides a summary of statistical comparisons of plasma dextromethorphan AUC (0-t) relating to the effect of quinidine doses on a 60 mg dose of dextromethorphan.

TABLE 5

| Treatment Comparison | Geometric | Means | Ratio of GEOMEANS | P |
|---|---|---|---|---|
| A vs. D | 35.11 | 2159.23 | 0.02 | 0.0001 |
| B vs. D | 1888.72 | 2159.23 | 0.87 | 0.7601 |
| C vs. D | 2108.96 | 2159.23 | 0.98 | 0.9608 |

Table 6 provides a summary of plasma dextromethorphan pharmacokinetic parameters following a 45 mg dose of dextromethorphan.

TABLE 6

| Pharmacokinetic | | Treatment E | | Treatment F | | Treatment G | | Treatment H | |
|---|---|---|---|---|---|---|---|---|---|
| Parameters | Day* | Mean | S.D. | Mean | S.D. | Mean | S.D. | Mean | S.D. |
| Cmax (ng/mL) | 1 | 2.3 | 1.60 | 9.6 | 13.91 | 3.6 | 5.04 | 1.7 | 1.08 |
| | 8 | 4.2 | 3.01 | 141.5 | 74.68 | 138.9 | 25.97 | 136.1 | 50.59 |
| | C | 1.9 | 2.03 | 131.9 | 62.92 | 135.3 | 23.87 | 134.4 | 50.80 |
| Tmax (hr) | 1 | 3.5 | 0.93 | 2.9 | 0.37 | 3.4 | 1.40 | 3.0 | 1.0 |
| | 8 | 3.4 | 0.50 | 4.3 | 1.70 | 3.3 | 1.80 | 3.6 | 2.07 |
| | C | −0.1 | 1.16 | 1.4 | 1.51 | −0.1 | 1.21 | 0.6 | 2.20 |
| AUC(0-t) | 1 | 14.9 | 11.39 | 77.5 | 120.80 | 25.4 | 36.89 | 10.2 | 7.08 |
| (ng*hr/mL) | 8 | 31.3 | 23.85 | 1438.0 | 842.60 | 1403.0 | 283.10 | 1464.0 | 588.60 |
| | C | 16.3 | 17.0 | 1360.0 | 736.20 | 1378.0 | 259.50 | 1453.0 | 589.30 |
| AUC (0-12) | 1 | 15.0 | 11.36 | 77.5 | 120.80 | 25.5 | 36.79 | 10.3 | 6.98 |
| (ng*hr/mL) | 8 | 31.5 | 23.64 | 1488.0 | 842.60 | 1403.0 | 283.10 | 1464.0 | 588.50 |
| | C | 16.5 | 16.82 | 1360.0 | 736.20 | 1378.0 | 259.60 | 1453.0 | 589.50 |
| 1n (Cmax) | 1 | 0.5 | 0.95 | 1.2 | 1.56 | 0.5 | 1.33 | 0.4 | 0.55 |
| | 8 | 1.1 | 1.09 | 4.8 | 0.52 | 4.9 | 0.19 | 4.8 | 0.45 |
| | C | 1.9 | 0.93 | 62.6 | 54.58 | 138.3 | 107.10 | 100.3 | 59.37 |
| In (AUC(0-t) | 1 | 2.2 | 1.45 | 3.2 | 1.64 | 2.3 | 1.45 | 2.1 | 0.65 |
| | 8 | 3.0 | 1.23 | 7.1 | 0.54 | 7.2 | 0.19 | 7.2 | 0.50 |
| | C | 2.6 | 1.60 | 89.6 | 78.74 | 241.2 | 206.30 | 188.5 | 112.20 |
| In (AUC(0-12) | 1 | 2.3 | 1.34 | 3.2 | 1.64 | 2.4 | 1.39 | 2.2 | 0.62 |
| | 8 | 3.0 | 1.17 | 7.1 | 0.54 | 7.2 | 0.19 | 7.2 | 0.50 |
| | C | 2.5 | 1.38 | 89.6 | 78.74 | 218.9 | 177.50 | 185.4 | 113.80 |

*= Code C corresponds to the change from the baseline, calculated as follows: for the untransformed parameters, it is the difference between Day 8 and Baseline values, for the In-transformed parameters, it is the ratio of Day 8 over Baseline values.

Table 7 provides a summary of statistical comparisons of plasma dextromethorphan AUC (0-12) relating to the effect of quinidine doses on a 60 mg dose of dextromethorphan.

TABLE 7

| Treatment Comparison | Geometric | Means | Ratio of GEOMEANS | P |
|---|---|---|---|---|
| E vs. H | 20.89 | 1342.73 | 0.02 | 0.0001 |
| F vs. H | 1266.94 | 1342.73 | 0.94 | 0.8945 |
| G vs. H | 1380.84 | 1342.73 | 1.03 | 0.9490 |

Table 8 provides a summary of statistical comparisons of plasma dextromethorphan AUC (0-t) relating to the effect of quinidine doses on a 60 mg dose of dextromethorphan.

TABLE 8

| Treatment Comparison | Geometric | Means | Ratio of GEOMEANS | P |
|---|---|---|---|---|
| E vs. H | 20.18 | 1342.73 | 0.02 | 0.0001 |
| F vs. H | 1266.94 | 1342.73 | 0.94 | 0.8980 |
| G vs. H | 1380.84 | 1342.73 | 1.03 | 0.9490 |

Table 9 provides a summary of plasma dextromethorphan pharmacokinetic parameters following a 60 mg dose of dextromethorphan.

TABLE 9

| Pharmacokinetic | | Treatment A | | Treatment B | | Treatment C | | Treatment D | |
|---|---|---|---|---|---|---|---|---|---|
| Parameters | Day* | Mean | S.D. | Mean | S.D. | Mean | S.D. | Mean | S.D. |
| Cmax (ng/mL) | 1 | 663.6 | 111.69 | 858.1 | 75.95 | 885.4 | 33.23 | 655.5 | 145.57 |
| | 8 | 709.6 | 88.82 | 176.7 | 41.40 | 90.1 | 24.55 | 110.8 | 27.68 |
| | C | 46.0 | 142.71 | −681.4 | 75.24 | −795.3 | 57.72 | −544.8 | 126.32 |
| Tmax (hr) | 1 | 2.2 | 0.37 | 2.0 | 0.01 | 2.0 | 0.03 | 2.0 | 0.01 |
| | 8 | 2.1 | 0.38 | 1.6 | 1.60 | 5.3 | 5.77 | 4.3 | 4.13 |
| | C | −0.0 | 0.58 | −0.4 | 1.59 | 3.3 | 5.78 | 2.3 | 4.13 |
| AUC(0-t) | 1 | 3240.0 | 494.10 | 3953.0 | 516.80 | 3669.0 | 468.10 | 3237.0 | 515.10 |
| (ng*hr/mL) | 8 | 3608.0 | 386.80 | 1830.0 | 443.10 | 958.0 | 248.80 | 1157.0 | 281.30 |
| | C | 367.9 | 581.60 | −2123.0 | 322.70 | −2711.0 | 467.40 | −2080.0 | 369.40 |
| AUC (0-12) | 1 | 3240.0 | 494.10 | 3953.0 | 516.80 | 3669.0 | 468.10 | 3237.0 | 515.10 |
| (ng*hr/mL) | 8 | 3608.0 | 386.80 | 1830.0 | 443.10 | 958.0 | 248.80 | 1157.0 | 281.30 |
| | C | 367.9 | 581.60 | −2123.0 | 322.70 | −2711.0 | 467.40 | −2080.0 | 369.40 |
| 1n (Cmax) | 1 | 6.5 | 0.16 | 6.8 | 0.09 | 6.8 | 0.04 | 6.5 | 0.23 |
| | 8 | 6.6 | 0.12 | 5.2 | 0.24 | 4.5 | 0.27 | 4.7 | 0.27 |
| | C | 1.1 | 0.22 | 0.2 | 0.05 | 0.1 | 0.03 | 0.2 | 0.04 |
| In (AUC(0-t) | 1 | 8.1 | 0.15 | 8.3 | 0.13 | 8.2 | 0.13 | 8.1 | 0.16 |
| | 8 | 8.2 | 0.11 | 7.5 | 0.26 | 6.8 | 0.25 | 7.0 | 0.27 |
| | C | 1.1 | 0.19 | 0.5 | 0.08 | 0.3 | 0.07 | 0.4 | 0.06 |
| In (AUC(0-12) | 1 | 8.1 | 0.15 | 8.3 | 0.13 | 8.2 | 0.13 | 8.1 | 0.16 |
| | 8 | 8.2 | 0.11 | 7.5 | 0.26 | 6.8 | 0.25 | 7.0 | 0.27 |
| | C | 1.1 | 0.19 | 0.5 | 0.08 | 0.3 | 0.07 | 0.4 | 0.06 |

*= Code C corresponds to the Change from the baseline, calculated as follows: for the untransformed parameters, it is the difference between Day 8 and Baseline values, for the In-transformed parameters, it is the ratio of Day 8 over Baseline values.

Table 10 provides a summary of statistical comparisons of plasma dextromethorphan AUC (0-12) as relates to the effect of quinidine doses on 60 mg of Dextromethorphan.

TABLE 10

| Treatment Comparison | Geometric | Means | Ratio of GEOMEANS | P |
|---|---|---|---|---|
| A vs. D | 3589.57 | 1125.35 | 3.19 | 0.0001 |
| B vs. D | 1786.16 | 1125.35 | 1.59 | 0.0046 |
| C vs. D | 937.28 | 1125.35 | 0.83 | 0.2521 |

Table 11 provides a summary of statistical comparisons of plasma dextromethorphan AUC (0-t) as relates to the effect of quinidine doses on 60 mg of Dextromethorphan.

TABLE 11

| Treatment Comparison | Geometric | Means | Ratio of GEOMEANS | P |
|---|---|---|---|---|
| A vs. D | 3589.57 | 1125.35 | 3.19 | 0.0001 |
| B vs. D | 1786.16 | 1125.35 | 1.59 | 0.0046 |
| C vs. D | 937.28 | 1125.35 | 0.83 | 0.2521 |

Table 12 provides a summary of plasma dextromethorphan pharmacokinetic parameters following a 45 mg dose of dextromethorphan.

TABLE 12

| Pharmacokinetic | | Treatment E | | Treatment F | | Treatment G | | Treatment H | |
|---|---|---|---|---|---|---|---|---|---|
| Parameters | Day* | Mean | S.D. | Mean | S.D. | Mean | S.D. | Mean | S.D. |
| Cmax (ng/mL) | 1 | 587.4 | 172.23 | 446.6 | 216.16 | 554.0 | 209.23 | 607.3 | 125.85 |
| | 8 | 599.2 | 199.89 | 89.1 | 25.97 | 86.8 | 23.11 | 77.7 | 15.81 |
| | C | 11.9 | 94.36 | −357.5 | 215.39 | −467.2 | 188.06 | −529.6 | 126.09 |
| Tmax (hr) | 1 | 2.0 | 0.00 | 2.0 | 0.01 | 2.2 | .038 | 2.0 | 0.01 |
| | 8 | 2.0 | 0.01 | 2.3 | 1.38 | 1.0 | 1.12 | 1.3 | 1.20 |
| | C | 0.0 | 0.01 | 0.3 | 1.38 | −1.2 | 1.25 | 0.7 | 1.20 |
| AUC(0-t) | 1 | 2618.0 | 603.10 | 2260.0 | 751.50 | 2462.0 | 737.10 | 2860.0 | 580.40 |
| (ng*hr/mL) | 8 | 2898.0 | 900.50 | 920.7 | 275.90 | 874.1 | 283.80 | 782.6 | 129.9 |
| | C | 280.7 | 430.70 | −1340.0 | 751.40 | −1588.0 | 537.30 | −2078.0 | 535.00 |
| AUC (0-12) | 1 | 2618.0 | 603.10 | 2260.0 | 751.50 | 2481.0 | 732.00 | 2860.0 | 580.40 |
| (ng*hr/mL) | 8 | 2898.0 | 900.50 | 920.7 | 275.90 | 874.1 | 238.80 | 782.6 | 129.90 |
| | C | 280.7 | 430.70 | −1340.0 | 751.40 | −1607.0 | 536.50 | −2078.0 | 535.00 |
| 1n (Cmax) | 1 | 6.3 | 0.30 | 6.0 | 0.62 | 6.3 | 0.37 | 6.4 | 0.20 |
| | 8 | 6.3 | 0.35 | 4.5 | 0.29 | 4.4 | 0.27 | 4.3 | 0.20 |
| | C | 1.0 | 0.19 | 0.3 | 0.24 | 0.2 | 0.03 | 0.1 | 0.04 |
| In (AUC(0-t) | 1 | 7.8 | 0.22 | 7.7 | 0.39 | 7.8 | 0.27 | 7.9 | 0.21 |
| | 8 | 7.9 | 0.31 | 6.8 | 0.31 | 6.7 | 0.28 | 6.7 | 0.17 |
| | C | 1.1 | 0.17 | 0.5 | 0.24 | 0.4 | 0.05 | 0.3 | 0.06 |
| In (AUC(0-12) | 1 | 7.8 | 0.22 | 7.7 | 0.39 | 7.8 | 0.27 | 7.9 | 0.21 |
| | 8 | 7.9 | 0.31 | 6.8 | 0.31 | 6.7 | 0.28 | 6.7 | 0.17 |
| | C | 1.1 | 0.17 | 0.5 | 0.24 | 0.4 | 0.05 | 0.3 | 0.06 |

*= Code C corresponds to the Change from the baseline, calculated as follows: for the untransformed parameters, it is the difference between Day 8 and Baseline values, for the In-transformed parameters, it is the ratio of Day 8 over Baseline values.

Table 13 provides a summary of statistical comparisons of plasma dextromethorphan AUC (0-12) as relates to the effect of quinidine doses on a 45 mg dose of dextromethorphan.

TABLE 13

| Treatment Comparison | Geometric | Means | Ratio of GEOMEANS | P |
|---|---|---|---|---|
| E vs. H | 2777.40 | 773.75 | 3.59 | 0.0001 |
| F vs. H | 884.33 | 773.75 | 1.14 | 0.4276 |
| G vs. H | 846.26 | 773.75 | 1.09 | 0.5933 |

Table 14 provides a summary of statistical comparisons of plasma dextromethorphan AUC (0-t) as relates to the effect of quinidine doses on a 45 mg dose of dextromethorphan.

TABLE 14

| Treatment Comparison | Geometric | Means | Ratio of GEOMEANS | P |
|---|---|---|---|---|
| E vs. H | 277.40 | 773.75 | 3.59 | 0.0001 |
| F vs. H | 884.33 | 773.75 | 1.14 | 0.4276 |
| G vs. H | 846.26 | 773.75 | 1.09 | 0.5933 |

Table 15 provides a summary of plasma dextromethorphan pharmacokinetic parameters following a 60 mg dose of dextromethorphan.

TABLE 15

| Pharmacokinetic | | Treatment A | | Treatment B | | Treatment C | | Treatment D | |
|---|---|---|---|---|---|---|---|---|---|
| Parameters | Day* | Mean | S.D. | Mean | S.D. | Mean | S.D. | Mean | S.D. |
| Cmax (mcg/mL) | 8 | 0.0 | 0.00 | 0.1 | 0.05 | 0.3 | 0.02 | 0.3 | 0.15 |
| Tmax (mcr) | 8 | . | . | 2.3 | 1.26 | 1.3 | 0.58 | 1.8 | 0.40 |
| AUC(0-Tt) (mcg-hr/mL) | 8 | 0.0 | 0.00 | 0.9 | 0.40 | 1.9 | 0.10 | 2.4 | 1.29 |
| AUC(0-12) (mcg*hr/mL) | 8 | 0.0 | 0.00 | 1.0 | 0.34 | 1.9 | 0.10 | 2.5 | 1.22 |
| 1n(Cmax) | 8 | . | . | −2.0 | 0.33 | −1.3 | 0.07 | −1.1 | 0.43 |
| 1n[AUC(0-t)] | 8 | . | . | −0.2 | 0.40 | 0.6 | 0.05 | 0.8 | 0.58 |
| 1n[AUC(0-12)] | 8 | . | . | −0.1 | 0.33 | 0.6 | 0.05 | 0.8 | 0.51 |

*= For Quinidine, only Day 8 data were analyzed

Table 16 provides a summary of plasma dextromethorphan pharmacokinetic parameters following a 45 mg dose of dextromethorphan.

TABLE 16

| Pharmacokinetic | | Treatment E | | Treatment F | | Treatment G | | Treatment H | |
|---|---|---|---|---|---|---|---|---|---|
| Parameters | Day* | Mean | S.D. | Mean | S.D. | Mean | S.D. | Mean | S.D. |
| Cmax (mcg/mL) | 8 | 0.0 | 0.00 | 0.2 | 0.11 | 0.3 | 0.13 | 0.3 | 0.06 |
| Tmax (mcr) | 8 | — | — | 1.6 | 0.79 | 1.2 | 0.57 | 1.8 | 1.3 |
| AUC (0-Tt) (mcg-hr/mL) | 8 | 0.0 | 0.00 | 1.0 | 0.77 | 2.0 | 0.91 | 2.3 | 0.71 |
| AUC (0-12) (mcg * hr/mL) | 8 | 0.0 | 0.00 | 1.1 | 0.74 | 2.0 | 0.88 | 2.3 | 0.64 |
| 1n (Cmax) | 8 | — | — | −1.8 | 0.58 | −1.3 | 0.44 | −1.1 | 0.19 |
| 1n [AUC (0-t)] | 8 | — | — | −0.2 | 0.66 | 0.6 | 0.48 | 0.8 | 0.33 |
| 1n [AUC (0-12)] | 8 | — | — | −0.1 | 0.61 | 0.6 | 0.44 | 0.8 | 0.28 |

*= For Quinidine, only Day 8 data were analyzed

Table 17 provides a summary of statistical comparisons of plasma quinidine AUC (0-12) as relates to different dextromethorphan/quinidine dose combinations.

TABLE 17

| Treatment Comparison | Geometric | Means | Ratio of GEOMEANS | P |
|---|---|---|---|---|
| F vs. B | 0.94 | 0.94 | 1.00 | 0.9925 |
| G vs. C | 1.88 | 1.89 | 1.00 | 0.9930 |
| H vs. D | 2.24 | 2.23 | 1.01 | 0.9765 |

Table 18 provides a summary of statistical comparisons of plasma quinidine AUC (0-t) as relates to different dextromethorphan/quinidine dose combinations.

TABLE 18

| Treatment Comparison | Geometric | Means | Ratio of GEOMEANS | P |
|---|---|---|---|---|
| F vs. B | 0.84 | 0.84 | 1.00 | 0.9987 |
| G vs. C | 1.84 | 1.89 | 0.97 | 0.9421 |
| H vs. D | 2.18 | 2.12 | 1.03 | 0.9294 |

A summary of the metabolic ratios for urinary pharmacokinetic parameters following a 60 mg dose of dextromethorphan are provided in Table 19.

A summary of statistical comparisons of urinary metabolic ratio for Ae (156-168 Hr) as relates to the effect of quinidine doses on a 60 mg dose of dextromethorphan are provided Table 20.

TABLE 20

| Treatment Comparison | Geometric | Means | Ratio of GEOMEANS | P |
|---|---|---|---|---|
| A vs. D | 0.01 | 1.12 | 0.01 | 0.0001 |
| B vs. D | 0.54 | 1.12 | 0.49 | 0.1947 |
| C vs. D | 1.17 | 1.12 | 1.05 | 0.9347 |

A summary of statistical comparisons of urinary metabolic ratio for CumAe (156-168 Hr) as relates to the effect of quinidine doses on a 60 mg dose of dextromethorphan are provided Table 21.

TABLE 21

| Treatment Comparison | Geometric | Means | Ratio of GEOMEANS | P |
|---|---|---|---|---|
| A vs. D | 0.01 | 0.41 | 0.02 | 0.0001 |
| B vs. D | 0.18 | 0.41 | 0.45 | 0.0822 |
| C vs. D | 0.32 | 0.41 | 0.80 | 0.6485 |

TABLE 19

| | | Treatment A | | Treatment B | | Treatment C | | Treatment D | |
|---|---|---|---|---|---|---|---|---|---|
| Period | Pharmacokinetic Parameters | Arithmetic Mean | S.D. | Arithmetic Mean | S.D. | Arithmetic Mean | S.D. | Arithmetic Mean | S.D. |
| 0-12 hr | Ae | 0.0013 | 0.0023 | 0.0010 | 0.0015 | 0.0027 | 0.0048 | 0.0041 | 0.0070 |
| | CumAe | 0.0013 | 0.0023 | 0.0010 | 0.0015 | 0.0027 | 0.0048 | 0.0041 | 0.0070 |
| 12-24 hr | Ae | 0.0058 | 0.0055 | 0.0865 | 0.0496 | 0.2748 | 0.2228 | 0.2934 | 0.2046 |
| | CumAe | 0.0031 | 0.0039 | 0.0253 | 0.0116 | 0.0641 | 0.0504 | 0.0632 | 0.0362 |
| 60-72 hr | Ae | 0.0133 | 0.0122 | 0.8139 | 0.3464 | 1.3598 | 0.7454 | 2.0366 | 0.9219 |
| | CumAe | 0.0058 | 0.0061 | 0.1248 | 0.0545 | 0.2374 | 0.1904 | 0.2966 | 0.1670 |
| 156-168 hr | Ae | 0.0179 | 0.0163 | 0.6513 | 0.4119 | 1.1785 | 0.1517 | 1.3023 | 0.7430 |
| | CumAe | 0.0085 | 0.0092 | 0.2005 | 0.1129 | 0.3493 | 0.1676 | 0.4374 | 0.1767 |

0-12 hr collecting period corresponds to Baseline, when only Dextromethorphan (no Quinidine) was administered at the specific dose.

Ae = Amount excreted (mcg)

CumAe = Cumulative Amount Excreted (mcg)

A summary of the metabolic ratios for urinary pharmacokinetic parameters following a 45 mg dose of dextromethorphan are provided in Table 22.

TABLE 22

| Period | Pharmacokinetic Parameters | Treatment A Arithmetic Mean | Treatment A S.D. | Treatment B Arithmetic Mean | Treatment B S.D. | Treatment C Arithmetic Mean | Treatment C S.D. | Treatment D Arithmetic Mean | Treatment D S.D. |
|---|---|---|---|---|---|---|---|---|---|
| 0-12 hr | Ae | 0.0022 | 0.0043 | 0.0454 | 0.0768 | 0.0130 | 0.0271 | 0.0017 | 0.0025 |
| | CumAe | 0.0022 | 0.0043 | 0.0454 | 0.0768 | 0.0130 | 0.0271 | 0.0017 | 0.0025 |
| 12-24 hr | Ae | 0.0044 | 0.0043 | 0.2338 | 0.1996 | 0.2647 | 0.1224 | 0.3252 | 0.1955 |
| | CumAe | 0.0032 | 0.0043 | 0.1078 | 0.1130 | 0.0798 | 0.0393 | 0.0774 | 0.0554 |
| 60-72 hr | Ae | 0.0089 | 0.0096 | 1.2159 | 0.4110 | 1.2594 | 0.5056 | 0.8073 | 0.4256 |
| | CumAe | 0.0052 | 0.0061 | 0.3673 | 0.1438 | 0.2837 | 0.1087 | 0.1889 | 0.0621 |
| 156-168 hr | Ae | 0.0087 | 0.0097 | 0.9387 | 0.2688 | 1.6276 | 0.7287 | 0.8770 | 0.4967 |
| | CumAe | 0.0059 | 0.0054 | 0.4826 | 0.1201 | 0.4912 | 0.2480 | 0.3468 | 0.1477 |

0-12 hr collecting period corresponds to Baseline, when only Dextromethorphan (no Quinidine) was administered at the specific dose.
Ae = Amount excreted (mcg)
CumAe = Cumulative Amount Excreted (mcg)

A summary of statistical comparisons of urinary metabolic ratio for Ae (156-168 Hr) as relates to the effect of quinidine doses on a 45 mg dose of dextromethorphan are provided Table 23.

TABLE 23

| Treatment Comparison | Geometric | Means | Ratio of GEOMEANS | P |
|---|---|---|---|---|
| E vs. H | 0.01 | 0.75 | 0.01 | 0.0001 |
| F vs. H | 0.90 | 0.75 | 1.20 | 0.5713 |
| G vs. H | 1.46 | 0.75 | 1.95 | 0.0469 |

A summary of statistical comparisons of urinary metabolic ratio for CumAe (156-168 Hr) as relates to the effect of quinidine doses on a 45 mg dose of dextromethorphan are provided Table 24.

TABLE 24

| Treatment Comparison | Geometric | Means | Ratio of GEOMEANS | P |
|---|---|---|---|---|
| E vs. H | 0.01 | 0.32 | 0.02 | 0.0001 |
| F vs. H | 0.47 | 0.32 | 1.48 | 0.2201 |
| G vs. H | 0.43 | 0.32 | 1.36 | 0.3345 |

The data suggest that co-administration of dextromethorphan and quinidine sulfate is safe and moderately well tolerated up to the highest dose level (60 mg dextromethorphan/60 mg quinidine).

There were a total of 279 treatment-emergent adverse events experienced by forty-eight of the sixty-five subjects dosed (74%) during the trial. There were 206 adverse events reported by twenty-seven of the thirty-two subjects dosed (84%) following the 60 mg dextromethorphan treatments and seventy-three adverse events reported by twenty-one of the thirty-three subjects dosed (64%) following the 45 mg dextromethorphan treatments. Twelve subjects following the 60 mg dextromethorphan treatments and five subjects following the 45 mg dextromethorphan treatments were discontinued from the trial due to adverse events.

Dizziness, nausea, and headache were the most common adverse events following both dextromethorphan groups, and fewer adverse events were reported following the 45 mg dextromethorphan treatments. All of the adverse events were mild or moderate in severity and no serious adverse events occurred. No clinically significant differences were observed between the treatment groups regarding clinical laboratory results, vital signs, physical examination, or ECG results.

Over the course of this study, quinidine inhibited the metabolism of dextromethorphan dosed at 45 and 60 mg resulting in increased systemic availability of dextromethorphan. The 60 mg quinidine dose resulted in the largest dextromethorphan AUC at both the 45 and 60 mg dextromethorphan doses, compared to the 30 and 45 mg quinidine doses. The statistical comparisons, however, showed there were not only statistically significant differences in the quinidine inhibition of dextromethorphan metabolism among the different quinidine doses. Based on dextromethorphan AUC statistical comparisons, the lowest effective dose of quinidine that inhibits the metabolism of 45 and 60 mg dextromethorphan is 30 mg. Thus, a 30 mg quinidine dose is recommended for dextromethorphan inhibition.

The occurrence of side effects during the co-administration of dextromethorphan and quinidine sulfate indicated the treatments were moderately well tolerated up to the highest dose level (60 mg dextromethorphan/60 mg quinidine).

Clinical Study #4

The objectives of this study were to compare and evaluate the efficacy, safety, and tolerance of a combination of 30DM/30Q taken twice daily relative to 30 mg DM and 30 mg Q taken individually in a population of ALS subjects with pseudobulbar affect.

This was a multicenter, randomized, double-blind, controlled, parallel-group study. All study drugs were self-administered orally every twelve hours for twenty-eight days. The study included a screening visit and three other clinic visits on Days 1, 15, and 29. Day 29 was the last day the subject was on study and could occur anywhere between the morning of Day 26 and the morning of Day 32.

Subjects with clinically diagnosed pseudobulbar affect were screened for general health within four weeks before entry into the study. All eligible subjects had attained a score of 13 or above on the Center for Neurologic Study-Lability Scale (CNS-LS) at the clinic visit on Day 1.

Subjects were randomized to one of three treatment groups to receive 30DM/30Q, or 30 mg DM, or 30 mg Q. They received a diary in which they recorded the date and time each dose was taken, the number of laughing/crying episodes experienced, and any adverse events that had occurred since the last visit. Diary cards were collected on Day 15 and at the time of study completion.

Subjects completed the CNS-LS questionnaire and visual analog scales assessing quality of life (QOL) and quality of relationships (QOR) every two weeks (Days 1, 15, and 29) during the treatment period. A clinical psychologist, or other approved clinician, administered the Hamilton Rating Scale for Depression (HRSD) at the Screening Visit and on Day 29.

Safety was evaluated on Day 15 and Day 29 by examining adverse events, results of physical examinations, vital signs, clinical laboratory values, and resting electrocardiograms (ECGs). In addition to blood samples taken to provide clinical laboratory data, blood was also taken for pharmacokinetic analysis and CYP2D6 genotyping. Each subject completed a diary in which the number of episodes experienced, medications taken, and any adverse events were recorded daily.

DM and Q were chosen as control groups because they are the components of the drug investigated in this study (30DM/30Q).

Subjects included in the study were 18 to 80 years of age, inclusive. The subjects had a confirmed diagnosis of ALS or probable ALS according to the World Federation of Neurology (WFN) criteria, and a clinical history of pseudobulbar affect. Every effort was made by the to continue a subject in the study; however, if the subject decided to withdraw, all efforts were made to complete all assessments listed on Day 29 in Table 25. An explanation of why the subject withdrew from the study was obtained. Subjects who withdrew from the study could not re-enter it, and no subject who had been randomized was replaced.

The study drugs were randomized in blocks of four. Each block contained two assignments to the 30DM/30Q, one to DM and one to Q in random order. Specifically, each block was constructed by selecting one of the four possibilities to be received first. From the three remaining treatments, one was selected to be received next, and so forth. Subject numbers were allocated to study sites in one block of four assignments at a time.

There were three treatments administered in the study: 30DM/30Q, or 30 mg DM, or 30 mg Q. Study medications were provided as hard, gelatin capsules. The contents of the capsules is listed in Table 25. All medication used in the study was prepared according to current Good Manufacturing Practice (cGMP).

TABLE 25

| Ingredient | Amount (mg) | | |
|---|---|---|---|
| | DM/Q | DM | Q |
| Dextromethorphan hydrobromide monohydrate USP | 31.50 | 31.50 | 0.00 |
| Quinidine sulfate dihydrate USP | 31.40 | 0.00 | 31.40 |
| Croscarmellose sodium NF | 7.80 | 7.80 | 7.80 |
| Microcrystalline cellulose NF | 94.00 | 109.70 | 109.75 |
| Colloidal silicone dioxide NF | 0.65 | 0.65 | 0.65 |
| Lactose monohydrate NF | 94.00 | 109.70 | 109.75 |
| Magnesium stearate NF | 0.65 | 0.65 | 0.65 |

Subjects took one capsule twice a day (every 12 hours) for twenty-eight days. The first dose was taken in the evening of Day 1, and the final dose was taken in the morning on Day 29. The investigators were supplied with capsules of 30DM/30Q, DM, and Q in identical blister-packs, and all capsules were identical in appearance and weight.

Subjects could not take any disallowed medications during the study or for one week before the start of dosing on Day 1. These medications included amantadine, amitriptyline, any anti-depressant medication including St. John's Wort, any monoamine oxidase inhibitor, aspirin (for pain or fever acetaminophen was recommended), captopril, cimetidine, desipramine, dextromethorphan (over-the-counter cough medicines), digoxin, diltiazem, erythromycin, fluoxetine, imipramine, itraconazole, ketoconazole, nortriptyline, paroxetine, quinidine, quinine, and verapamil. At each visit, subjects were queried as to whether or not they had taken any medications, and if they had, the medication was recorded on the Case Report Form.

Subjects were instructed to bring unused study medication to the visit on Day 15 visit and to return all unused study medication to the clinic at the end of study participation. Percent of doses taken was calculated as the total number of doses taken divided by the total number of doses planned, and the result was multiplied by 100. Subjects were considered to be compliant if they had taken 80% of their prescribed doses.

The primary efficacy variable was the CNS-LS score. All efficacy variables involving a change were determined by the baseline score being subtracted from the mean of the non-missing scores on Days 15 and 29. The secondary efficacy variables were laughing/crying episodes, QOL scores, and QOR scores. All efficacy variables involving a change were determined by subtracting the baseline score from the mean of the scores on Days 15 and 29.

The CNS-LS questionnaire used to assess primary efficacy is a seven-item self-report measure that provides a score for total pseudobulbar affect; it required approximately five minutes for the subject to complete. The range of possible scores was 7 to 35. The cut-off score of 13 was selected because it has been reported in the literature to provide the highest incremental validity, accurately predicting the neurologists' diagnoses for 82% of participants with a sensitivity of 0.84 and a specificity of 0.81. This questionnaire is the only instrument for the measurement of pseudobulbar affect validated for use with ALS subjects.

Secondary efficacy was assessed by using two, 10-cm visual analog scales (VAS). One scale asked subjects to rate how much uncontrollable laughter, tearfulness, or anger had affected the overall quality of their life during the past week, and one scale asked subjects to rate how much uncontrollable laughter, tearfulness, or anger had affected the quality of their relationships with others during the past week. Each scale required less than one minute to complete. The subjects recorded episodes of pathological laughing and crying in a diary daily.

Safety was assessed by the following measurements: adverse events; clinical laboratory values; vital signs; physical examinations; and resting ECGs. An adverse event was defined any untoward medical occurrence or unintended change from the subject's baseline (pre-treatment) condition, including intercurrent illness, that occurs during the course of a clinical trial after treatment has started, whether considered related to treatment or not. An adverse event was any unfavorable and unintended sign (including an abnormal laboratory finding, for example), symptom, or disease temporally associated with the use of a medicinal product, whether or not considered related to the medicinal product. Changes associated with normal growth and development not varying in frequency or magnitude from that ordinarily anticipated clinically are not adverse events (for example, onset of menstruation occurring at a physiologically appropriate time). Clinical adverse events were described by diagnosis and not by symptoms when possible (for example, cold or seasonal allergies, instead of "runny nose").

The severity of adverse events was graded on a 3-point scale and reported in detail as indicated on the Case Report Form: mild—easily tolerated, causing minimal discomfort, and not interfering with normal everyday activities; moderate—sufficiently discomforting to interfere with normal everyday activities; and severe—incapacitating and/or preventing normal everyday activities. The relationship of study medication to each adverse event was determined by the investigator by using the following definitions: not related— the event was clearly related to other factors, such as the subject's clinical state, therapeutic interventions, or concomitant medications administered to the subject; unlikely—the event was most likely produced by other factors, such as the subject's clinical state, therapeutic interventions, or concomitant medications administered to the subject, and did not follow a known response pattern to the study drug; possible—the event followed a reasonable temporal sequence from the time of drug administration, and/or followed a known response pattern to the study drug, but could have been produced by other factors, such as the subject's clinical state, therapeutic interventions, or concomitant medications administered to the subject; probable—the event followed a reasonable temporal sequence from the time of drug administration, followed a known response pattern to the trial drug, and could not be reasonably explained by other factors, such as the subject's clinical state, therapeutic interventions, or concomitant medications administered to the subject; highly probable—the event followed a reasonable temporal sequence from the time of drug administration, and followed a known response pattern to the trial drug, and could not be reasonably explained by other factors, such as the subject's clinical state, therapeutic interventions, or concomitant medications administered to the subject, and either occurs immediately following study drug administration or improves on stopping the drug or reappears on repeat exposure.

A serious adverse event was any adverse event occurring at any dose that resulted in any of the following outcomes: death; life-threatening experience (one that places the subject at immediate risk of death from the adverse event as it occurred, for example, it does not include an adverse event that, had it occurred in a more severe form, might have caused death); persistent or significant disability/incapacity (disability is a substantial disruption of a person's ability to conduct normal life functions); in-patient hospitalization or prolongation of hospitalization; and congenital anomaly/birth defect.

Subjects were instructed to promptly report any adverse event. The serious adverse event was assessed for the following details: seriousness of event, start date, stop date, intensity, frequency, relationship to test drug, action taken regarding test drug, treatment required, and outcome to date. These details were recorded on the Case Report Form. Such preliminary reports were followed by detailed descriptions that included copies of hospital case reports, autopsy reports, and other documents when requested and applicable.

Blood and urine were collected at the screening visit and Day 29 for clinical chemistry, hematology, urinalysis, and pregnancy testing. In the event of an abnormal laboratory test value, the test was repeated within one week, and the subject was followed up until the value returned to the normal range and/or until an adequate explanation of the abnormality was found.

Values were obtained for systolic and diastolic blood pressure, heart rate, and respiration rate on the screening visit and all other study visits. All values outside the pre-defined ranges were flagged in the subject data listings. Electrocardiography (twelve lead) was used to obtain ventricular rate (VR), QT, Q-$T_c$ intervals, pulse rate (PR), and QRS duration. A blood sample (10 mL whole blood) was taken from each subject at the Screening Visit for CYP2D6 genotyping to determine which subjects were poor metabolizers of DM and which were extensive metabolizers. Blood samples were taken on Day 29 for the determination of concentrations of DM, DX, and Q in plasma. The relationship between the concentration of drug in plasma and changes in CNS-LS scores was determined, and the effect of the CYP2D6 genotype on this relationship was evaluated.

Sample sizes of forty-eight subjects in the 30DM/30Q group and twenty-four subjects in each of the DM and Q groups were sufficient to detect a difference in CNS-LS score of 5.5 between the DM/Q group and each of the other groups. These calculations were based on standard deviations of 7, 5, and 3 in the DM/Q, DM, and Q groups, respectively. The power is approximately 85% based on a 2-sided, 5% test, assuming baseline/Day 15 and baseline/Day 29 correlations are both 0.3, and the Day 15/Day 29 correlation is 0.7. The assumptions on which sample sizes were based were drawn from a small, fourteen subject crossover study, in which DM/Q subjects had a mean change from baseline of −6.6 points with standard deviation of 7.5; and placebo-treated subjects had a mean change of +0.83 with a standard deviation of 3.2.

A total of 140 subjects were randomized to treatment; seventy were in the 30DM/30Q group, thirty-three were in the DM group, and thirty-seven were in the Q group. The sample size calculations required that there be only forty-eight subjects in the 30DM/30Q group and twenty-four subjects in each of the other treatment groups. Therefore, under the assumptions made in the sample size calculations, the number of subjects in each group was adequate to detect the defined difference in treatment effect. The percent of subjects with compliance ≧80% was 73.5 in the 30DM/30Q group, 87.9 in the DM group, and 86.5 in the Q group.

Three data sets were analyzed in this study; the safety data set consisting of data for 140 subjects, the intent-to-treat data set consisting of data for 129 subjects, and the efficacy-evaluable data set consisting of data for 101 subjects. The definitions of these three populations are as follows: safety population—all randomized subjects; intent-to-treat population—all randomized subjects who are not "poor metabolizers" of cytochrome P450 2D6; and efficacy evaluable population—all subjects in the ITT population who were protocol adherent. Subjects were considered adherent if they completed the visit on Day 29, completed all study procedures, and took 80% of their scheduled doses.

The demographic characteristics of the ITT population are provided in Table 26; the history of ALS is in Table 27, and the scores at baseline for depression, pseudobulbar affect, QOL, and QOR are in Table 28.

TABLE 26

| Category | 30DM/30Q (N = 65) | DM (N = 30) | Q (N = 34) | P-values[a] 30DM/30Q vs DM | P-values[a] 30DM/30Q vs Q |
|---|---|---|---|---|---|
| Age (years) | | | | | |
| n | 65 | 30 | 34 | | |
| Mean | 54.82 | 53.77 | 55.32 | 0.7788 | 0.9976 |
| Std Dev | 12.79 | 11.25 | 9.47 | | |
| Median | 55 | 54 | 58 | | |
| Min/Max | 38/82 | 33/75 | 35/72 | | |

TABLE 26-continued

| Category | 30DM/30Q (N = 65) | DM (N = 30) | Q (N = 34) | P-values[a] 30DM/30Q vs DM | P-values[a] 30DM/30Q vs Q |
|---|---|---|---|---|---|
| Gender, n (%) | | | | | |
| Female | 23 (35.4) | 14 (46.7) | 12 (35.3) | 0.1549 | 0.8105 |
| Male | 42 (64.6) | 16 (53.3) | 22 (64.7) | | |
| Race, n (%) | | | | | |
| Asian | 0 (0) | 1 (3.3) | 0 (0) | 0.2100 | 0.5522 |
| Black | 2 (3.1) | 0 (0) | 0 (0) | | |
| Caucasian | 58 (89.2) | 25 (83.3) | 31 (91.2) | | |
| Hispanic | 5 (7.7) | 3 (10.0) | 3 (8.8) | | |
| Other | 0 (0.00) | 1 (3.3) | 0 (0.00) | | |

[a]P-values to compare means for continuous variables are computed by using ANOVA with an adjustment for treatment and center to obtain overall F-tests. P-values for categorical values were computed by using Cochran-Mantel-Haenszel chi-square with an adjustment for center.

TABLE 27

| Category | 30DM/30Q (N = 65) | DM (N = 30) | Q (N = 34) | P-values[a] 30DM/30Q vs DM | P-values[a] 30DM/30Q vs Q |
|---|---|---|---|---|---|
| ALS Type, n (%) | | | | | |
| Bulbar | 29 (44.6) | 14 (46.7) | 21 (61.8) | 0.8341 | 0.0793 |
| Limb | 36 (55.4) | 16 (53.3) | 13 (38.2) | | |
| Weekly Episode of Laughing/Crying | | | | | |
| n | 65 | 30 | 34 | | |
| Mean | 22.18 | 38.93 | 19.35 | 0.0897 | 0.7043 |
| Std Dev | 31.62 | 66.28 | 19.04 | | |
| Median | 11 | 17 | 13 | | |
| Min/Max | 2/210 | 1/350 | 2/70 | | |

[a]P-values to compare means for continuous variables are computed by using ANOVA with an adjustment for treatment and center to obtain overall F-tests. P-values for categorical values were computed by using Cochran-Mantel-Haenszel chi-square with an adjustment for center.

TABLE 28

| Baseline Characteristics[a] | 30DM/30Q (N = 65) | DM (N = 30) | Q (N = 34) | P-values[b] 30DM/30Q vs DM | P-values[b] 30DM/30Q vs Q |
|---|---|---|---|---|---|
| HRSD | | | | | |
| N | 65 | 30 | 34 | | |
| Mean | 5.37 | 4.27 | 5.79 | 0.1404 | 0.7066 |
| Std Dev | 4.33 | 3.05 | 4.20 | | |
| Median | 4.0 | 3.5 | 5.0 | | |
| Min/Max | 0/16 | 0/14 | 0/15 | | |
| CNS-LS | | | | | |
| n | 65 | 30 | 34 | | |
| Mean | 20.06 | 21.40 | 22.26 | 0.3202 | 0.0705 |
| Std Dev | 5.46 | 6.17 | 5.22 | | |
| Median | 19.0 | 20.0 | 21.0 | | |
| Min/Max | 11/33 | 13/35 | 13/33 | | |
| VAS-QOL | | | | | |
| n | 65 | 30 | 34 | | |
| Mean | 35.05 | 47.57 | 46.56 | 0.0209 | 0.0261 |
| Std Dev | 26.70 | 27.24 | 26.93 | | |
| Median | 33.0 | 48.5 | 42.0 | | |
| Min/Max | 0/96 | 5/95 | 2/100 | | |
| VAS-QOR | | | | | |
| n | 65 | 30 | 34 | | |
| Mean | 31.77 | 41.07 | 42.18 | 0.1435 | 0.0646 |
| Std Dev | 28.50 | 28.16 | 29.93 | | |
| Median | 28.0 | 41.5 | 34.5 | | |
| Min/Max | 0/99 | 0/95 | 0/100 | | |

[a]HRSD = Hamilton Rating Scale for Depression; CNS-LS = Center for Neurologic Study Lability Scale; VAS = Visual Analog Scale; QOL = Quality of Life; QOR = Quality of Relationships. Baseline measurements for HRSD were done at screening. Baseline measurements for CNS-LS, VAS-QOL, and VAS-QOR were done on Day 1.

[b]P-values to compare means were computed by using ANOVA with an adjustment for treatment and center to obtain overall F-tests.

There were no statistically significant differences between the 30DM/30Q group and the DM and Q groups for any demographic variable. The only statistically significant difference in the baseline characteristics was in the QOL scores. Subjects in the 30DM/30Q group rated their QOL better at baseline than did the subjects in either of the other two treatment groups. Similar demographic results were obtained in the efficacy-evaluable population, and the trend in the baseline characteristics was in the same direction as that in the ITT population. The population of interest in the primary and secondary analyses of efficacy was the ITT population. Therefore, all results shown in the text are those obtained from this population.

The primary efficacy analysis was the change from baseline in CNS-LS scores, adjusted for center and baseline CNS-LS score. The descriptive statistics for the ITT Population are in Table 29.

TABLE 29

| Change in Score[a] | 30DM/30Q (N = 65) | DM (N = 30) | Q (N = 34) |
|---|---|---|---|
| n | 61 | 30 | 34 |
| Mean | −7.39 | −5.12 | −4.91 |
| Std Dev | 5.37 | 5.56 | 5.56 |
| Median | −6.50 | −4.50 | −4.25 |
| Min/Max | −24.00/0.0 | −25.00/2.0 | −21.00/2.0 |

[a]Change in CNS-LS scores was defined as the mean of scores on Day 15 and Day 29 minus the baseline (Day 1) score.

The distributions of CNS-LS scores at baseline, Day 15, and Day 29 for each of the three treatment groups are provided in FIG. 1. These distributions have not been adjusted for baseline scores or for study site. As shown in FIG. 1, the distributions of CNS-LS scores are symmetrical and contain only one outlier. These distributions support the use of ANCOVA for the analysis of the CNS-LS scores. As prospectively specified in the protocol, the differences in mean improvement in CNS-LS scores, adjusted for center and baseline CNS-LS scores, were analyzed by using linear regression according to the ANCOVA method of Frison and Pocock. The results of this analysis are in Table 30. The results of additional analyses without any adjustments or with an adjustment for baseline CNS-LS score alone are also in this table.

TABLE 30

| Statistics | 30DM/30Q vs DM | 30DM/30Q vs Q |
|---|---|---|
| Unadjusted difference in mean score | −2.27 | −2.47 |
| Std Err | 1.22 | 1.17 |
| p-value | 0.0652 | 0.0366 |
| Difference in mean score adjusted for baseline CNS-LS score | −2.97 | −3.65 |
| Std Err | 1.03 | 1.00 |
| p-value | 0.0046 | 0.0004 |
| *Difference in mean score adjusted for baseline CNS-LS score and center*[b] | −3.29 | −3.71 |
| *Std Err* | 1.00 | 0.97 |
| *p-value* | 0.0013 | 0.0002 |

[a]Change in CNS-LS scores was defined as the mean of the scores on Day 15 and Day 29 minus the baseline (Day 1) score.
[b]Analysis in italics was pre-specified in the Statistical Analysis Plan.

The mean score in the group treated with 30DM/30Q was statistically significantly different from the mean scores of the group treated with DM and from the mean scores of the group treated with Q. Therefore, subjects treated with 30DM/30Q showed a significant improvement in pseudobulbar affect.

Figure 2:
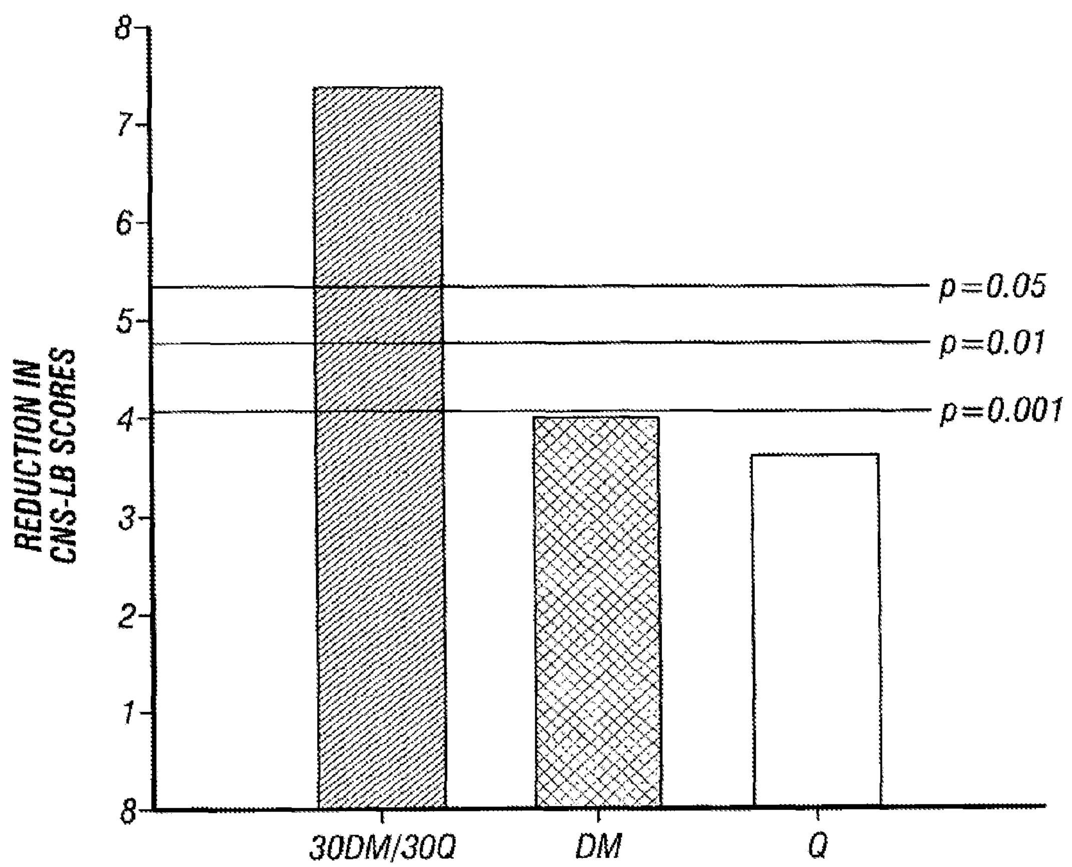
FIG. 2 provides a plot depicting adjusted mean reductions in CNS-LS scores for the three treatment groups from the primary efficacy analysis of the ITT population of Clinical Study #4. Reductions in CNS-LS scores below the horizontal lines are statistically significantly different from 30DM/30Q at the significance levels indicated.

The results for the analysis pre-specified in the protocol are shown graphically in FIG. 2. Adjusted mean reductions in CNS-LS scores for the three treatment groups from the primary efficacy analysis of the ITT population. Reductions in CNS-LS scores below the horizontal lines are statistically significantly different from 30DM/30Q at the significance levels indicated.

The primary efficacy analysis was also done for the efficacy-evaluable and the safety populations. These results are in Table 31. The results in these populations also showed that 30DM/30Q significantly improved pseudobulbar affect.

TABLE 31

| | | | P-values vs 30DM/30Q | |
|---|---|---|---|---|
| Statistics[b] | DM | Q | DM | Q |
| ITT Population (n = 125) | | | | |
| Difference vs 30DM/30Q | −3.29 | −3.71 | 0.0013 | 0.0002 |
| Std Error | 1.00 | 0.97 | | |
| Efficacy Evaluable Population (n = 101) | | | | |
| Difference vs 30DM/30Q | −3.78 | −5.00 | 0.0009 | <0.0001 |
| Std Error | 1.10 | 1.10 | | |
| Safety Population (n = 136) | | | | |
| Difference vs 30DM/30Q | −3.09 | −4.23 | 0.0016 | <0.0001 |
| Std Error | 0.96 | 0.93 | | |

[a]The ITT and EFF populations excluded poor metabolizers.
[b]Differences are mean differences in the CNS-LS reduction, controlling for baseline CNS-LS and study site, using the analysis pre-specified in the Statistical Analysis Plan.

The results in these populations also showed that 30DM/30Q significantly improved pseudobulbar affect.

The primary efficacy data were also analyzed by using linear regression according to the ANCOVA method of Frison and Pocock with an adjustment for center, baseline CNS-LS scores, and treatment-by-center interaction. Because of small sample sizes at some centers, this interaction could not be estimated.

An analysis of secondary efficacy data was conducted. Weekly episode counts were analyzed by using the Poisson regression model as specified in the statistical analysis plan, and the results are in Table 32.

TABLE 32

| | Episode[a] | | |
|---|---|---|---|
| Statistic | 30DM/30Q (N = 65) | DM (N = 30) | Q (N = 34) |
| Laughing | | | |
| n | 62 | 30 | 34 |
| Wtd. Mean[b] | 4.70 | 35.29 | 6.79 |
| Wtd. Std Dev | 49.66 | 709.97 | 53.93 |
| Median | 0.66 | 2.50 | 2.23 |
| Min/Max | 0.00/116.67 | 0.00/726.55 | 0.00/45.00 |
| Crying | | | |
| n | 62 | 30 | 34 |
| Wtd. Mean[b] | 2.04 | 4.30 | 5.64 |
| Wtd. Std Dev | 33.99 | 32.86 | 28.14 |
| Median | 0.44 | 0.70 | 4.00 |
| Min/Max | 0.00/66.00 | 0.00/21.00 | 0.00/19.83 |
| Laughing/Crying | | | |
| n | 62 | 30 | 34 |
| Wtd. Mean[b] | 6.74 | 39.58 | 12.45 |
| Wtd. Std Dev | 69.23 | 707.62 | 69.91 |
| Median | 2.00 | 8.97 | 6.19 |
| Min/Max | 0.00/116.67 | 0.00/726.55 | 0.00/49.00 |

[a]The number of episodes were collected continuously by each subject in a diary. The diaries were reviewed at the visits on Days 15 and 29.
[b]The mean across all subjects was the weighted mean of each subject's mean (total number of episodes divided by the total number of days). The weight is the number of days in the study for each subject.

This analysis of episode rates, pre-specified in the protocol, showed that total episodes were 6.4 times greater (calculated by using the episode rates from the Poisson regression model with an adjustment for center) in the DM group than in the 30DM/30Q group and were 1.9 times greater in the Q group than in the 30DM/30Q group. A single outlier in the DM group was a subject who reported 10 times more episodes than any other subject in the study—an average of over 100 episodes per day. When this outlier was omitted, the ratios were 2.3 and 1.8 for the DM and Q groups, respectively. In each case, the calculated p-values were <0.0001. Separate assessments for crying and laughing were also highly statistically significant. This subject's extreme episodes counts were primarily laughing episodes; as a result, the estimated effects on crying were changed little by omitting this subject.

For the assessments for episode counts described above, there is evidence of substantial overdispersion in the data, signifying that the data did not meet the assumptions of the model. A number of additional analyses were carried out to assess the sensitivity of the conclusions to model specification; these analyses are discussed below.

When the data were analyzed by using the quadratic-variance (mean dispersion) negative binomial model (one model for overdispersion), the results indicated that 30DM/30Q crying rates were twice as large as those for DM (p=0.06) and 4.5 times as large as those for Q (p<0.001). The corresponding factors for laughing were 2.6 (p=0.10) and 0.9 (p=0.84) and for total are 2.6 (p=0.013) and 1.5 (p=0.29). However, there is a continued lack of fit of the data in this model also.

The data were also analyzed by using the proportional-variance (constant dispersion) negative binomial model (another model that takes overdispersion into account). The results, indicated by an analysis of residuals, showed a better fit to this overdispersed data. The estimated ratios from this model for crying were 2.0 (p=0.007) and 3.3 (p<0.001) relative to DM and Q, respectively. For laughing, the ratios were 1.4 and 1.5, with p-values of 0.21 and 0.13 for DM and Q, respectively. (With the outlier subject omitted, the laughing ratios were 1.5 (p=0.14) and 1.6 (p=0.05). Total counts had ratios of 1.7 and 1.8, with p-values 0.02 and 0.006 relative to DM and Q, respectively.

When center was omitted from the model as a sensitivity analysis, the magnitude of response was similar to the analyses with center. The p-values increased somewhat, as expected. The normal probability plots of residuals from these models, however, indicate that adjustment for center substantially improved the normality of the residuals.

Additional studies to determine the sensitivity of the results to model assumptions were also carried out. These analyses explored nonparametric approaches, as well as an assessment designed to examine "steady-state" differences between groups.

The assessment of statistical significance of the relative effects of 30DM/30Q, DM, and Q is dependent on the model assumptions used. However, statistical estimates of the relative effects in all models consistently favored 30DM/30Q over DM and Q, even when statistical significance was not reached. In the model for which the assumptions best describe the observed data, these differences were statistically significant.

To help quantify and understand how changes in the primary efficacy variable, CNS-LS score, affect episode count, the effect of a 1-point difference in CNS-LS score on the episode rate during the previous two weeks was estimated. For each 1-point increase in CNS-LS score, the average episode rate increased 12%. Thus, a 3.5-point decrease in CNS-LS score would correspond to a 50% decrease in episode rate. This was true for both laughing and crying episodes. Summary statistics of QOL and QOR scores are in provided in Table 33.

TABLE 33

| Change in Score[a] | 30DM/30Q (N = 65) | DM (N = 30) | Q (N = 34) |
|---|---|---|---|
| | All Days | | |
| QOL | | | |
| n | 51 | 27 | 32 |
| Mean | −23.34 | −17.41 | −18.97 |
| Std Dev | 24.38 | 27.61 | 28.30 |
| Median | −19.0 | −11.0 | −14.3 |
| Min/Max | −84.0/29 | −90.5/27 | −98.0/19 |
| QOR | | | |
| n | 51 | 27 | 32 |
| Mean | −22.36 | −9.98 | −14.14 |
| Std Dev | 27.32 | 22.09 | 27.54 |
| Median | −12.00 | −4.50 | −10.50 |
| Min/Max | −90.0/24.0 | −71.0/23.5 | −74.5/42.0 |
| | Day 15 | | |
| QOL | | | |
| n | 52 | 28 | 33 |
| Mean | −20.54 | −17.14 | −15.94 |
| Std Dev | 23.05 | 29.06 | 28.51 |
| Median | −18 | −13 | −6 |
| Min/Max | −84/28 | −90/55 | −96/22 |
| QOR | | | |
| n | 52 | 28 | 33 |
| Mean | −20.77 | −11.75 | −12.15 |
| Std Dev | 26.11 | 24.88 | 29.05 |
| Median | −10 | −7 | −2 |
| Min/Max | −89/25 | −71/34 | −84/41 |
| | Day 29 | | |
| QOL | | | |
| n | 60 | 29 | 33 |
| Mean | −24.13 | −19.31 | −21.15 |
| Std Dev | 25.77 | 29.29 | 30.97 |
| Median | −17 | −7 | −14 |
| Min/Max | −90/30 | −91/27 | −100/23 |
| QOR | | | |
| n | 59 | 29 | 33 |
| Mean | −22.42 | −10.38 | −15.67 |
| Std Dev | 27.92 | 23.62 | 27.85 |
| Median | −13.0 | −3.0 | −13.0 |
| Min/Max | −91/34 | −71/26 | −77/43 |

[a]The change in VAS scores for all days was defined as the mean of the scores on Days 15 and 29 minus the score on Day 1; the change in score for Day 15 was defined as the score on Day 15 minus the score on Day 1; and the score on Day 29 was defined as the score on Day 29 minus the score on Day 1.

The differences in the mean changes in QOL and QOR scores between 30DM/30Q and DM and Q, adjusted for baseline and study site, are in Table 34. The group treated with 30DM/30Q showed a statistically significant improvement in these scores when compared with the group treated with DM and compared with the group treated with Q. These results were similar for all time periods.

TABLE 34

| Variable Statistics[a] | 30DM/30Q vs DM | 30DM/30Q vs Q |
|---|---|---|
| | All Days | |
| QOL | | |
| Difference | −15.00 | −14.67 |
| Std Err | 4.58 | 4.44 |
| p-value[b] | 0.0015 | 0.0013 |
| QOR | | |
| Difference | −18.35 | −16.08 |
| Std Err | 4.27 | 4.16 |
| p-value | <0.0001 | 0.0002 |

TABLE 34-continued

| Variable Statistics[a] | 30DM/30Q vs DM | 30DM/30Q vs Q |
|---|---|---|
| | Day 15 | |
| QOL | | |
| Difference | −11.11 | −12.60 |
| Std Err | 4.03 | 4.63 |
| p-value | 0.0235 | 0.0077 |
| QOR | | |
| Difference | −15.04 | −15.25 |
| Std Err | 4.49 | 4.32 |
| p-value | 0.0012 | 0.0006 |
| | Day 29 | |
| QOL | | |
| Difference | −16.33 | −13.57 |
| Std Err | 4.78 | 4.62 |
| p-value | 0.0009 | 0.0041 |
| QOR | | |
| Difference | −19.14 | −14.77 |
| Std Err | 4.33 | 4.24 |
| p-value | <0.0001 | 0.0007 |

[a]Change in VAS "all-day" scores was defined as the mean of the scores on Day 15 and Day 29 minus the baseline (Day 1) score. Change in the scores on Day 15 and Day 29 was defined as the score on that day minus the baseline score. Differences in changed scores were adjusted for baseline levels and center effects.
[b]P-values were computed by using linear regression according to the ANOVA method of Frison and Pocock with an adjustment for center and baseline QOL and QOR scores.

To account for multiple comparisons, all the secondary efficacy variables were combined and analyzed simultaneously by using the O'Brien Rank Sum Method, as specified in the protocol. The results showed that subjects treated with 30DM/30Q had a statistically significant reduction in episodes of laughing and crying and an improvement in QOL and QOR relative to the subjects treated with DM (p=0.0041) or Q (p=0.0001) after adjustment for multiple comparisons. 30DM/30Q was statistically significantly better that either DM or Q in improving pseudobulbar affect, number of episodes of laughing and crying, QOL, and QOR in subjects with ALS.

The extent of exposure to study medication, in terms of number of doses taken, is reported in Table 35. The mean days of exposure were very similar across all treatment groups.

TABLE 35

| Exposure Statistics[a] | 30DM/30Q (N = 70) | DM (N = 33) | Q (N = 37) |
|---|---|---|---|
| n | 68 | 33 | 36 |
| Mean | 24.4 | 27.6 | 28.0 |
| Std Dev | 9.66 | 6.25 | 4.40 |
| Median | 29.0 | 29.0 | 29.0 |
| Min/Max | 3/32 | 7/33 | 5/32 |

[a]Exposure was calculated by using the date of the last dose of study drug minus the date of the first dose of study drug + 1.

Nausea was the most common adverse event experienced, and it afflicted more subjects [twenty-three (32.9%)] in the 30DM/30Q group than in either the DM [2 (6.1%)] or the Q [3 (8.1%)] groups. However, in the 30DM/30Q group, nausea was judged to be mild or moderate in twenty of the twenty-three subjects, but it was judged to be at least possibly related to treatment with 30DM/30Q in nineteen of the twenty-three subjects. All instances of nausea in the DM and Q groups were mild or moderate, and all but one was judged to be at least possibly related to treatment. Dizziness was also reported by more subjects [fourteen (20%)] in the 30DM/30Q group than in either the DM [five (15.2%)] or the Q [one (2.7%)] groups. All instances of this adverse event in all treatment groups were mild or moderate, and almost all were judged to be at least possibly related to treatment. Somnolence was the third event that was reported by more subjects [nine (12.9%)] in the 30DM/30Q group than in either the DM [one (3.0%)] or the Q [zero (0%)] groups. All instances of this adverse event in all treatment groups were mild or moderate, and almost all were judged to be at least possibly related to treatment. Three subjects experienced loose stools as an adverse event, and all of them were in the DM group. All instances of the event were mild, and all were judged to be related to treatment.

A total of twenty-two subjects withdrew from the study because of adverse events; seventeen (24.3%) were in the 30DM/30Q group, two (6.1%) in the DM group, and three (8.1%) in the Q group. The seventeen subjects in the 30DM/30Q group experienced fifty adverse events, and most of these [seventeen (34%)] were related to the nervous system. All of these fifty events except four were mild or moderate, and all but one were judged to be at least possibly related to treatment. One subject had a severe headache, one subject had severe nausea and severe vomiting, and one subject had severe respiratory failure. The subject died as a result of the respiratory failure. This was judged not related to study medication. The other two subjects recovered without sequelae.

In the DM group, there were seven adverse events experienced by two subjects. All of these events except one were mild or moderate, and all were judged to be related to treatment. One subject, who had six of the seven adverse events, experienced severe diarrhea; received appropriate drug treatment for this condition; and recovered without sequelae.

Three subjects in the Q group experienced five adverse events. One subject had a severe kidney infection that was judged to be not related to treatment, and one subject had severe muscle cramping that was judged to be related to treatment. Both of these subjects recovered without sequelae. All other adverse events were mild or moderate, and most were judged to be not related to treatment.

Overall, there were four serious adverse events experienced by subjects in this study. Three subjects in the 30DM/30Q group reported serious adverse events, but only one of these discontinued taking the drug. All three of these serious adverse events were judged to be not related to the study drug. The only other serious adverse event was experienced by a subject in the Q group. This subject continued on the study drug, and the event was also judged to be not related to the study drug. There was one death during the study; one subject in the 30DM/30Q group died because of respiratory failure unrelated to study treatment.

There was no statistically significant change in hematology, clinical chemistry, or urinalysis values from Baseline to Day 29 in any treatment group, nor any statistically significant change among the treatment groups in any laboratory value except a significant increase in CPK in the DM group relative to the 30DM/30Q group. There were no clinically relevant changes from Baseline to Day 29 in systolic blood pressure, diastolic blood pressure, heart rate, or respiration. There were no clinically relevant changes from Baseline to Day 29 in the results of physical examinations. There was a statistically significant difference in the change from Baseline to Day 29 in VR and in the QT interval between the 30DM/30Q and Q groups. However, these changes were so small that they were not clinically relevant. There was no statistically significant difference among the treatment groups in $QT_c$, PR, and QRS duration.

Since the nature, frequency, and intensity of the adverse events were within acceptable limits in this subject population, and there were no clinically relevant findings for any other safety variable, 30DM/30Q is safe in this subject population.

The CYP2D6 genotypes in each treatment group of the safety population were determined and are provided in Table 36. As defined in the Statistical Analysis Plan, the ITT population did not include poor metabolizers. Extensive metabolizer was the most prevalent genotype in all treatment groups in the ITT population.

TABLE 36

| Genotype | 30DM/30Q (N = 70) n (%) | DM (N = 33) n (%) | Q (N = 37) n (%) |
|---|---|---|---|
| Poor metabolizer | 5 (7.2) | 3 (9.1) | 3 (8.1) |
| Extensive metabolizer | 61 (88.4) | 30 (90.9) | 32 (86.5) |
| Ultrarapid metabolizer | 3 (4.3) | 0 (0.0) | 2 (5.4) |

Q in this combination product inhibits the rapid first-pass metabolism of DM. Therefore, it was expected that the concentrations of DM in plasma would be higher and the concentration of its metabolite, DX, would be lower in subjects who had received 30DM/30Q. The concentrations of DM and DX in the group receiving 30DM/30Q and the group receiving DM are provided in Table 37.

TABLE 37

| | 30DM/30Q N = 70 | | DM N = 33 | | P-values[b] | |
|---|---|---|---|---|---|---|
| Statistics | DM | DX | DM | DX | DM | DX |
| n | 35 | 35 | 23 | 23 | | |
| Mean | 96.37 | 89.46 | 5.18 | 295.92 | <0.0001 | <0.0001 |
| Std Dev | 46.71 | 52.25 | 4.97 | 143.21 | | |
| Median | 96.26 | 78.24 | 4.55 | 262.35 | | |
| Min/Max | 1.07/212.40 | 8.17/235.27 | 0.35/15.81 | 101.07/526.65 | | |

[a]Only those subjects whose time of blood collection was within 8 hours of the time of their last dose of study medication were included in this table.
[b]P-value from ANOVA with adjustment for treatment.

The mean DM concentration was 18.6-fold higher in the 30DM/30Q group than in the DM group, and the mean DX concentration was 3.3-fold lower in the 30DM/30Q group than in the DM group. These differences were both statistically significant. The data for the levels in plasma of all subjects show the same results as in those subjects whose blood was collected within eight hours of the last dose of study medication.

The results of the study demonstrate that 30DM/30Q was statistically significantly more effective than its components in the treatment of pseudobulbar affect as indicated by the primary and all secondary endpoints. Expected adverse events were reported, and no unexpected safety issues emerged. More subjects in the 30DM/30Q group had adverse events than in either of the other groups, and seventeen subjects in the 30DM/30Q group discontinued the study because of adverse events; however, all adverse events except four in the subjects who discontinued were mild or moderate. Only two of the seventeen subjects had severe adverse events (headache, nausea, vomiting), and these events, although debilitating, resolved without sequelae. There were three subjects treated with 30DM/30Q with serious events, and all of the events were unrelated to this treatment. Furthermore, as the results of the assessments of QOL and QOR were markedly and statistically significantly better in the subjects treated with 30DM/30Q, the benefits of the drug outweighed any discomfort caused by the adverse events. Therefore, 30DM/30Q was very effective in treating pseudobulbar affect in ALS subjects, and the drug was safe and well tolerated.

Clinical Study #5

The primary objective of this study was to evaluate the safety and tolerability of capsules containing dextromethorphan hydrobromide and quinidine sulfate (DM/Q) during an open-label, dose-escalation study to the subject's maximum tolerated dose (MTD), not to exceed 120 mg DM/120 mg Q per day. The secondary objective was to obtain a preliminary assessment of the efficacy of DM/Q in the treatment of pain associated with diabetic neuropathy.

This was an open-label, dose-escalation study in subjects experiencing pain associated with diabetic neuropathy. After screening for inclusion/exclusion criteria, subjects underwent a washout period during which all analgesics were discontinued. This was followed by twenty-nine days of treatment with capsules containing 30 mg DM/30 mg Q, beginning with one capsule per day and escalating approximately weekly to a maximum permitted dose of four capsules per day. Subjects who could not tolerate a dose level could return to the previous level; could substitute a capsule containing 15 mg DM/30 mg Q; or, if they were unable to tolerate the lowest dose level, could be discontinued from the study.

Subjects were screened for general health, including electrocardiography, within four weeks before Day 1 of dosing. The first dose of DM/Q was administered at the clinic, and a resting electrocardiogram was obtained one hour after this dose and interpreted on site. If the corrected QT interval ($QT_c$) determined in this preliminary interpretation was not ≧450 msec for males or ≧470 msec for females, and the $QT_c$ did not change from the screening electrocardiogram by more than 30 msec, the subject was issued study medication to take as directed by the physician. The subject was instructed on the use of a daily diary to record study medication taken and scores from rating scales for sleep, present and average pain intensity, and activity.

Subjects visited the clinic every two weeks during the four-week duration of the study and were contacted by telephone during weeks without clinic visits. At each subsequent study visit or weekly phone call, the subjects were given the Pain Intensity Rating Scale and the Pain Relief Rating Scale and were queried regarding any adverse events that might have occurred since their previous visit. Subjects were administered the Peripheral Neuropathy Quality of Life (QOL) Instrument on Days 1 and 29 (or the final visit). Blood samples were taken at the visits on Day 15 and Day 29 to determine concentrations in plasma of DM, DX, and Q.

Subjects selected were 18 to 80 years of age, inclusive, and had a confirmed diagnosis of diabetes mellitus. Subject had acceptable glycemic control, with total glycosylated hemoglobin (HbA1c) <12%, had been on established diabetic therapy for at least 3 months, had a clinical diagnosis of distal symmetrical diabetic neuropathy, and had daily pain associated with diabetic neuropathy for the previous 3 months. Subjects scored moderate or greater (≧2) on the Pain Intensity Rating Scale before receiving DM/Q on Day 1.

Every effort was made to continue each subject in the study. However, if a subject decided to withdraw, all efforts were made to complete all assessments and an explanation of why the subject withdrew from the study was provided.

Subjects received capsules containing 30 mg DM/30 mg Q or 15 mg DM/30 mg Q in increasing dosages, to a maximum of 120 mg DM/120 mg Q. Study medications were provided as hard gelatin capsules; Capsule A was opaque orange, and Capsule B was opaque white. The contents of the capsules are listed in Table 38.

TABLE 38

| Ingredient | Amount (mg) Capsule A 30 mg DM/30 mg Q | Capsule B[a] 15 mg DM/30 mg Q |
|---|---|---|
| Dextromethorphan hydrobromide monohydrate USP (DM) | 31.50[b] | 15.75[c] |
| Quinidine sulfate dihydrate USP (Q) | 31.40[d] | 31.40[d] |
| Croscarmellose sodium NF | 7.80 | 7.80 |
| Microcrystalline cellulose NF | 94.00 | 101.87 |
| Colloidal silicone dioxide NF | 0.050 | 0.065 |
| Lactose monohydrate NF | 94.00 | 101.88 |
| Magnesium stearate NF | 0.05 | 0.05 |

[a]For optional use if Capsule A was not tolerated.
[b]Equivalent to 30.0 mg dextromethorphan hydrobromide.
[c]Equivalent to 15.0 mg dextromethorphan hydrobromide.
[d]Equivalent to 30.0 mg quinidine sulfate.

Subjects received capsules containing DM/Q in escalating doses, as indicated in Table 39. Subjects who could not tolerate a dose level were permitted to return to the previous level, substitute a capsule containing 15 mg DM/30 mg Q, or be discontinued from the study if they were unable to tolerate the lowest dose level.

TABLE 39

| Study Day | AM Dose Number of Capsules | AM Dose DM (mg) | AM Dose Q (mg) | PM Dose Number of Capsules | PM Dose DM (mg) | PM Dose Q (mg) | Total Daily Dose Number of Capsules | Total Daily Dose DM (mg) | Total Daily Dose Q (mg) |
|---|---|---|---|---|---|---|---|---|---|
| 1 (in clinic) | 0 | 0 | 0 | 1 | 30 | 30 | 1 | 30 | 30 |
| 2 to 3 | 0 | 0 | 0 | 1 | 30 | 30 | 1 | 30 | 30 |
| 4 to 13 | 1 | 30 | 30 | 1 | 30 | 30 | 2 | 60 | 60 |
| 14 to 20 | 1 | 30 | 30 | 2 | 60 | 60 | 3 | 90 | 90 |
| 21 to 29 | 2 | 60 | 60 | 2 | 60 | 60 | 4 | 120 | 120 |

Subjects could not take any disallowed medications during the study or for one week (or two weeks, where applicable) before the start of dosing on Day 1. These medications included: amantadine; amitriptyline; any antidepressant medication, including St. John's Wort; any monoamine oxidase inhibitor; analgesics (only acetaminophen could be used); captopril; cimetidine; carbonic anhydrase inhibitors; desipramine; dextromethorphan (OTC cough medicines); digoxin; diltiazem; erythromycin; fluoxetine; haloperidol; imipramine; itraconazole; ketoconazole; nortriptyline; paroxetine; quinidine or other antiarrhythmic drugs; sodium bicarbonate; thiazide diuretics; and verapamil. If a subject was unable to complete the washout period without analgesia, he/she was permitted to begin the dose-escalation phase of the study, provided that sufficient washout of other disallowed, non-pain medications had occurred. Daily, low-dose aspirin was not considered an analgesic and was permitted for cardiac prophylaxis.

Acetaminophen was the only analgesic permitted as a rescue pain medication and was to be taken at the dosage specified on the package label. Subjects were instructed to consult the study clinic before taking any medication, including over-the-counter (OTC) medications, and they were counseled that acetaminophen-containing products that also contained other analgesics (e.g., codeine) or dextromethorphan should be avoided.

Subjects were instructed to bring unused study medication to the clinic on Day 15 and to return all unused study medication to the clinic at the final visit. Diary cards were collected from subjects at these visits. The percent of doses taken was calculated as the total number of doses taken divided by the total number of doses prescribed, multiplied by 100.

Safety was assessed by the following measurements: adverse events; clinical laboratory values; vital signs; physical examinations; electrocardiograms; and measurements of nerve conduction velocity.

Subjects underwent nerve conduction studies at Screening and on Day 29 (or the final visit). Nerve conduction velocity was measured with surface stimulation and recording. Bilateral sural nerve sensory studies and a unilateral peroneal nerve motor study were performed or supervised by a clinical electromyographer certified by the American Board of Electrodiagnostic Medicine. Techniques were standardized to minimize variability among electromyographers. Limb temperature was maintained above a standard temperature in all studies. Results were interpreted at a central reading laboratory.

Efficacy was assessed through the following instruments: Pain Intensity Rating Scale; Diary Present Pain Intensity Scale; Pain Relief Rating Scale; Diary Activity Rating Scale; Peripheral Neuropathy QOL Instrument; Diary Average Pain Rating Scale; and Diary Sleep Rating Scale.

Score on the Pain Intensity Rating Scale was determined on Day 8, Day 15, Day 22, and Day 29 (or the final visit). Subjects indicated the amount of pain experienced in the lower extremities within the previous twenty-four hours by using a 5-point Likert scale (0=None, 1=Mild, 2=Moderate, 3=Severe, 4=Extreme). Subjects were required to complete the Pain Intensity Rating Scale at the clinic on Day 1, before entry into the study and on Day 15 and Day 29 (or the final visit). The scale was also administered verbally in telephone calls to the subject during weeks when no clinic visit was scheduled (Day 8 and Day 22).

The Pain Relief Rating Scale was completed on Day 8, Day 15, Day 22, and Day 29 (or the final visit). Subjects indicated the amount of pain relief experienced in the lower extremities relative to the end of the washout/screening phase by using a 6-point Likert scale (−1=Worse, 0=None, 1=Slight, 2=Moderate, 3=A lot, 4=Complete). Subjects were required to complete the scale at the clinic on Day 15 and Day 29 (or the final visit). The Pain Relief Rating Scale was also administered verbally in telephone calls to the subject during weeks when no clinic visit was scheduled (Day 8 and Day 22).

The QOL score was obtained at the clinic on Day 1 and Day 29 (or the final visit). QOL was assessed by using the Peripheral Neuropathy QOL Instrument-97 as in Vickrey et al., Neurorehabi. Neural. Repair, 2000; 14:93-104. This is a self-administered, health-related, QOL measure for peripheral neuropathy. It incorporates the Health Status Survey SF-36 scale in its entirety and includes additional questions determined to be particularly relevant to subjects with peripheral neuropathy.

The instrument comprises 21 subscales containing items about general health issues, specific peripheral neuropathy issues, health symptoms or problems, assessment of overall health, and feelings in general and about health. All of the items use 3-, 4-, 5-, or 6-point categorical rating scales, except for number of disability days, overall health rating (0 to 100), and a yes/no question about sexual activity.

To analyze the QOL results, a scoring algorithm was used to convert the categorical item ratings to appropriate percent ratings. The most favorable rating was 100%, the least favorable was 0%, and the intermediate percents were spaced at equal intervals, depending on the number of points in the scale (e.g., 0, 25, 50, 75, 100 for a 5-point ascending scale; 100, 50, 0 for a 3-point descending scale). The converted ratings for each item in a subscale were averaged to provide the subscale scores. All subscale scores were constructed so that a higher value reflected a more favorable result. The composite QOL score was obtained by averaging all subscale scores, except for number of disability days.

The subject diary included a sleep rating scale and a present pain intensity scale to be completed in the morning, and an activity rating scale and an average pain rating scale to be completed in the evening. In the Sleep Rating Scale, subjects were instructed to circle the number on a scale of 0 to 10 that best described the extent that pain had interfered with their sleep in the past 24 hours (0=Does not interfere and 10=Completely interferes). In the Present Pain Intensity Scale, subjects were instructed to circle the statement that best described their present pain intensity: 0—No Pain; 1—Mild; 2—Discomforting; 3—Distressing; 4—Horrible; and 5—Excruciating. In the Activity Rating Scale, subjects were instructed to circle the number on a scale of 0 to 10 (the same as the Sleep Rating Scale) that best described the extent that pain had interfered with their general activity in the past 24 hours (0=Does not interfere and 10=Completely interferes). In the Average Pain in Past 12 Hours Rating Scale, subjects were instructed to circle the number on a scale of 0 to 10 (the same as the Sleep Rating Scale) that best described their average pain intensity during the past 12 hours (0=None and 10=Worst pain ever). The rating scales used as efficacy measures are well-established instruments in pain research, and the Peripheral Neuropathy QOL instrument, in particular, contains material that is specific for subjects with peripheral neuropathy.

Efficacy evaluations consisted of inferential analyses and summary statistics, calculated on all subjects and on subjects categorized by MTD, for the following variables (except where noted): change from baseline in the Pain Intensity Rating Scale score on Days 8, 15, 22, and 29 (or the final visit); the Pain Relief Rating Scale score on Days 8, 15, 22, and 29 (or the final visit); change from baseline in the composite score on the Peripheral Neuropathy Quality of Life Instrument on Day 29 (or the final visit); Sleep Interference score calculated from values recorded in the diary for the Sleep Rating Scale (the score for Day 15 was the average of the Sleep Rating Scale scores from the subject diary for Days 13, 14, and 15; the score for Day 29 was the average of the Day 27, 28, and 29 scores; and the Final Visit score was the average of scores from the final 3 consecutive days of study treatment); Daily Present Pain Intensity, Activity, Pain, and Sleep Rating scales, recorded in subject diaries; the percent of subjects experiencing improved scores for each of the efficacy variables.

Figure 3:
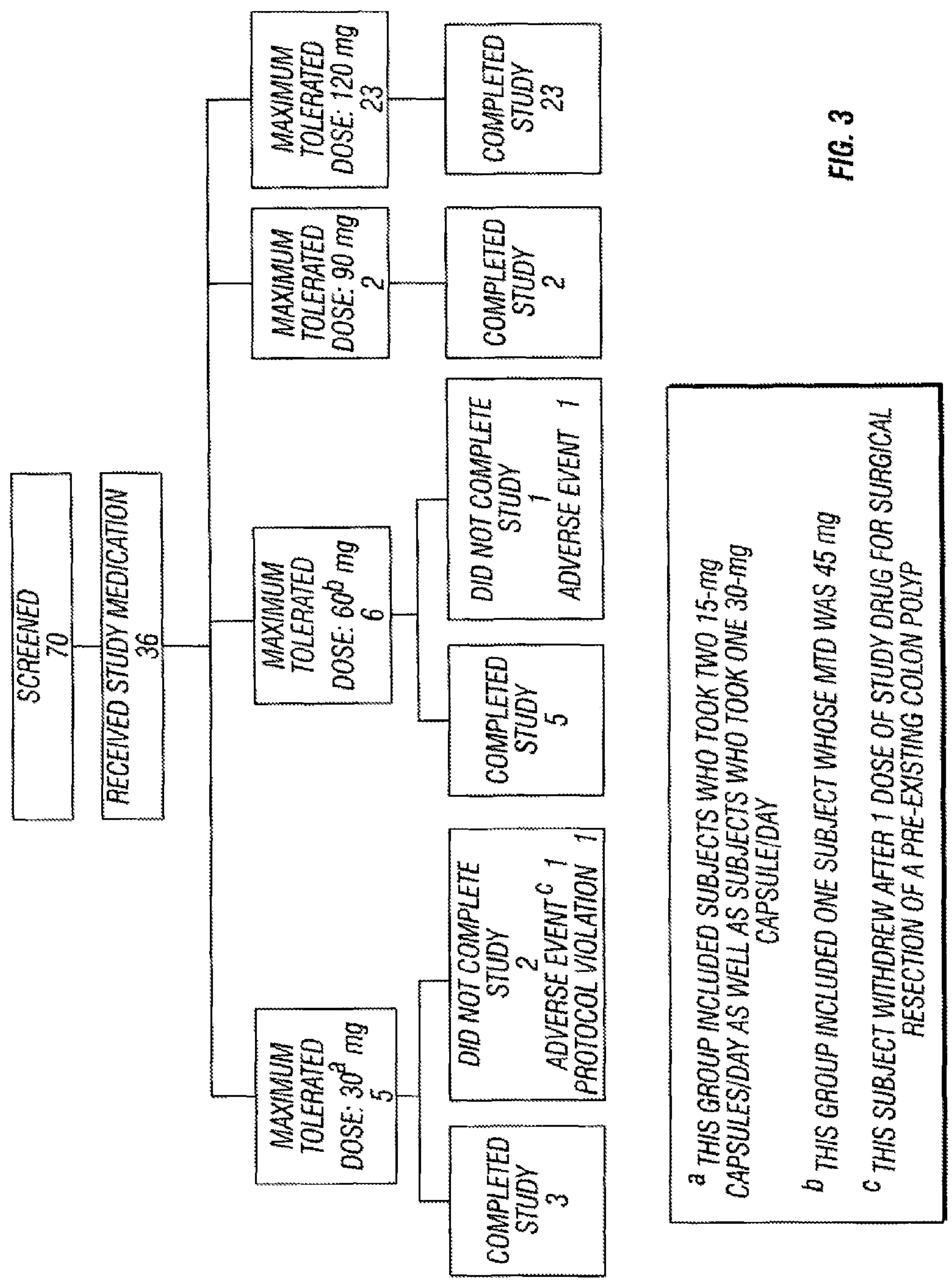
FIG. 3 provides the disposition of subjects by MTD group participating in Clinical Study #5.

The disposition of subjects is provided in FIG. 3. Subjects are classified by MTD group in this figure and in subsequent summary tables and figures. Except for a subject with an MTD of 45 mg, who was classified with the 60-mg group (see below), subjects in the 30-, 60-, and 90-mg groups received the MTDs indicated. Subjects in the 120-mg group tolerated this dose, which was the highest dose permitted in the study but is technically not an MTD. For brevity these groupings are all referred to as "MTDs."

Of the thirty-six subjects who were enrolled and received study medication, thirty-three completed the study. One subject completed the study with an MTD of 45 mg DM. Because there was only one subject with this MTD, this subject is included with the 60-mg MTD group in the data tables and in FIG. 3. The number of subjects in each MTD group and overall in each study site is reported in Table 40.

TABLE 40

| | MTD (mg) | | | | | |
|---|---|---|---|---|---|---|
| Site | 30 | 45 | 60 | 90 | 120 | Total |
| 01 | 1 | 0 | 0 | 0 | 4 | 5 |
| 02 | 1 | 0 | 0 | 0 | 3 | 4 |
| 03 | 0 | 0 | 3 | 0 | 0 | 3 |
| 04 | 2 | 1 | 2 | 2 | 5 | 12 |
| 05 | 1 | 0 | 0 | 0 | 11 | 12 |
| Total | 5 | 1 | 5 | 2 | 23 | 36 |

Only one population was used in the data analyses. Analyses and summaries were performed by using all 36 subjects who took study medication. The demographic characteristics of the study population are reported in Table 41.

TABLE 41

| | Maximum Tolerated Dose (mg)[a] | | | | |
|---|---|---|---|---|---|
| Characteristic | 30[b] (N = 5) | 60[c] (N = 6) | 90 (N = 2) | 120 (N = 23) | Total (N = 36) |
| Age (years) | | | | | |
| n | 5 | 6 | 2 | 23 | 36 |
| Mean | 62.2 | 57.7 | 57.0 | 57.1 | 57.9 |
| SD[d] | 10.99 | 8.14 | 9.90 | 11.99 | 10.94 |
| Median | 65.0 | 59.0 | 57.0 | 56.0 | 57.0 |
| Min/Max | 49/77 | 45/67 | 50/64 | 22/78 | 22/78 |
| Gender, n (%) | | | | | |
| Male | 4 (80.0) | 3 (50.0) | 1 (50.0) | 11 (47.8) | 19 (52.8) |
| Female | 1 (20.0) | 3 (50.0) | 1 (50.0) | 12 (52.2) | 17 (47.2) |
| Race, n (%) | | | | | |
| Caucasian | 3 (60.0) | 5 (83.3) | 2 (100.0) | 15 (65.2) | 25 (69.4) |
| Black | 1 (20.0) | 0 (0.0) | 0 (0.0) | 2 (8.7) | 3 (8.3) |

TABLE 41-continued

| Characteristic | Maximum Tolerated Dose (mg)[a] 30[b] (N = 5) | 60[c] (N = 6) | 90 (N = 2) | 120 (N = 23) | Total (N = 36) |
|---|---|---|---|---|---|
| Asian | 0 (0.0) | 0 (0.0) | 0 (0.0) | 0 (0.0) | 0 (0.0) |
| Other[e] | 1 (20.0) | 1 (16.7) | 0 (0.0) | 6 (26.1) | 8 (22.2) |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.
[d]SD = Standard deviation.
[e]All of the subjects in the category "Other" were described as Hispanic.

The history of the subjects' diabetic neuropathy is summarized in Table 42.

TABLE 42

| Characteristic | Maximum Tolerated Dose (mg)[a] 30[b] (N = 5) | 60[c] (N = 6) | 90 (N = 2) | 120 (N = 23) | Total (N = 36) |
|---|---|---|---|---|---|
| Duration of Diabetic Neuropathy (years) | | | | | |
| n | 5 | 6 | 2 | 23 | 36 |
| Mean | 3.9 | 3.8 | 3.2 | 5.3 | 4.7 |
| SD | 4.30 | 5.01 | 0.21 | 6.35 | 5.63 |

TABLE 42-continued

| Characteristic | Maximum Tolerated Dose (mg)[a] 30[b] (N = 5) | 60[c] (N = 6) | 90 (N = 2) | 120 (N = 23) | Total (N = 36) |
|---|---|---|---|---|---|
| Median | 2.5 | 0.9 | 3.2 | 2.4 | 2.5 |
| Min/Max | 0.6/11.4 | 0.2/10.4 | 3.0/3.3 | 0.5/24.3 | 0.2/24.3 |
| Duration of Daily Pain (months) | | | | | |
| n | 5 | 6 | 2 | 23 | 36 |
| Mean | 30.2 | 30.0 | 9.0 | 38.0 | 34.0 |
| SD | 30.99 | 17.47 | 4.24 | 46.32 | 39.42 |
| Median | 24.0 | 27.0 | 9.0 | 18.0 | 24.0 |
| Min/Max | 7/84 | 7/60 | 6/12 | 4/180 | 4/180 |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.

Subjects enrolled in the study had received their diagnosis of diabetic neuropathy a minimum of 0.2 years and a maximum of 24.3 years previously (median of 2.5 years). Subjects had experienced daily pain from their diabetic neuropathy for a minimum of four months and a maximum of 180 months/15.0 years (median of 24.0 months/2.0 years).

Concomitant medications were reported for up to 30 days before the study and throughout the treatment period. Concomitant medications reported by at least 10% of subjects overall are listed in Table 43 by WHO term.

TABLE 43

| Drug Category WHO Preferred Term | Maximum Tolerated Dose (mg)[a] 30[b] (N = 5) n (%) | 60[c] (N = 6) n (%) | 90 (N = 2) n (%) | 120 (N = 23) n (%) | Total (N = 36) n (%) |
|---|---|---|---|---|---|
| Analgesics | | | | | |
| Paracetamol (acetaminophen) | 0 (0.0) | 1 (16.7) | 1 (50.0) | 2 (8.7) | 4 (11.4) |
| ACE inhibitors | | | | | |
| Lisinopril | 0 (0.0) | 1 (16.7) | 0 (0.0) | 4 (17.4) | 5 (14.3) |
| Diuretics | | | | | |
| Furosemide | 0 (0.0) | 1 (16.7) | 0 (0.0) | 4 (17.4) | 5 (14.3) |
| Hydrochlorothiazide | 2 (40.0) | 1 (16.7) | 0 (0.0) | 2 (8.7) | 5 (14.3) |
| Anticoagulants | | | | | |
| Acetylsalicylic acid[d] | 1 (20.0) | 2 (33.3) | 1 (50.0) | 6 (26.1) | 10 (28.6) |
| Lipid-lowering agents | | | | | |
| Atorvastatin | 1 (20.0) | 0 (0.0) | 0 (0.0) | 5 (21.7) | 6 (17.1) |
| Antidiabetic agents | | | | | |
| Glibenclamide | 1 (20.0) | 1 (16.7) | 1 (50.0) | 5 (21.7) | 8 (22.9) |
| Glipizide | 0 (0.0) | 2 (33.3) | 0 (0.0) | 2 (8.7) | 4 (11.4) |
| Insulin | 2 (40.0) | 0 (0.0) | 0 (0.0) | 3 (13.0) | 5 (14.3) |
| Insulin human injection, isophane | 0 (0.0) | 2 (33.3) | 0 (0.0) | 2 (8.7) | 4 (11.4) |
| Metformin | 1 (20.0) | 1 (16.7) | 1 (50.0) | 6 (26.1) | 9 (25.7) |
| Metformin hydrochloride | 0 (0.0) | 1 (16.7) | 0 (0.0) | 6 (26.1) | 7 (20.0) |
| Oral antidiabetics | 4 (80.0) | 1 (16.7) | 1 (50.0) | 11 (47.8) | 17 (48.6) |
| Nutritional supplements | | | | | |
| Ascorbic acid | 1 (20.0) | 0 (0.0) | 1 (50.0) | 2 (8.7) | 4 (11.4) |
| Calcium | 1 (20.0) | 1 (16.7) | 1 (50.0) | 3 (13.0) | 6 (17.1) |
| Multivitamins | 0 (0.0) | 0 (0.0) | 1 (50.0) | 3 (13.0) | 4 (11.4) |
| Tocopherol | 1 (20.0) | 0 (0.0) | 0 (0.0) | 4 (17.4) | 5 (14.3) |

TABLE 43-continued

| Drug Category<br>WHO Preferred Term | Maximum Tolerated Dose (mg)[a] 30[b] (N = 5) n (%) | 60[c] (N = 6) n (%) | 90 (N = 2) n (%) | 120 (N = 23) n (%) | Total (N = 36) n (%) |
|---|---|---|---|---|---|
| Other | | | | | |
| Levothyroxine sodium | 0 (0.0) | 0 (0.0) | 1 (50.0) | 3 (13.0) | 4 (11.4) |
| Sildenafil citrate | 1 (20.0) | 3 (50.0) | 0 (0.0) | 0 (0.0) | 4 (11.4) |
| All other therapeutic products | 1 (20.0) | 1 (16.7) | 0 (0.0) | 2 (8.7) | 4 (11.4) |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.
[d]All subjects who took acetylsalicylic acid concurrently with their study treatment did so for the indication of cardiac prophylaxis and not analgesia.

Use of rescue medication (acetaminophen) was limited. Only four subjects took rescue medication: one took acetaminophen on twenty-eight out of twenty-nine study days, one on sixteen study days, and two on only one study day. Overall, there was little use of rescue medication for pain during this study; subjects took rescue medication on an average of 1.3 days each (4.5% of study days).

The extent of exposure to study medication is in Table 44.

TABLE 44

| Exposure Statistic | Maximum Tolerated Dose (mg)[a] 30[b] (N = 5) | 60[c] (N = 6) | 90 (N = 2) | 120 (N = 23) | Total (N = 36) |
|---|---|---|---|---|---|
| Amount of DM Taken (mg) | | | | | |
| n | 4 | 6 | 2 | 23 | 35 |
| Mean | 960.0 | 1442.5 | 2160 | 2321.7 | 2006.1 |
| SD | 667.68 | 682.42 | 42.43 | 121.94 | 609.17 |
| Median | 1095 | 1530 | 2160 | 2310 | 2310 |
| Min/Max | 30/1620 | 270/2370 | 2130/2190 | 2010/2640 | 30/2640 |
| Amount of Q Taken (mg) | | | | | |
| n | 4 | 6 | 2 | 23 | 35 |
| Mean | 1200.0 | 1525.0 | 2160.0 | 2321.7 | 2047.7 |
| SD | 781.15 | 682.90 | 42.43 | 121.94 | 562.49 |
| Median | 1575 | 1620 | 2160 | 2310 | 2310 |
| Min/Max | 30/1620 | 270/2370 | 2130/2190 | 2010/2640 | 30/2640 |
| Days on Study Medication[d] | | | | | |
| n | 4 | 6 | 2 | 23 | 35 |
| Mean | 22.0 | 25.3 | 29.0 | 29.0 | 27.6 |
| SD | 14.00 | 9.48 | 0.00 | 1.22 | 6.13 |
| Median | 29 | 29 | 29 | 29 | 29 |
| Min/Max | 1/29 | 6/30 | 29/29 | 25/32 | 1/32 |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.
[d]Number of days on study medication was calculated by using the date of the last dose of study drug minus the date of the first dose of study drug, plus 1.

The number of subjects with adverse events is reported in Table 45.

TABLE 45

| Category | Maximum Tolerated Dose (mg)[a] 30[b] (N = 5) n (%) | 60[c] (N = 6) n (%) | 90 (N = 2) n (%) | 120 (N = 23) n (%) | Total (N = 36) n (%) |
|---|---|---|---|---|---|
| Adverse Events | 4 (80.0) | 6 (100.0) | 2 (100.0) | 19 (82.6) | 31 (86.1) |
| Serious Adverse Events | 1 (20.0) | 2 (33.3) | 0 (0.0) | 0 (0.0) | 3 (8.3) |
| Discontinued Because of Adverse Events | 1 (20.0) | 1 (16.7) | 0 (0.0) | 0 (0.0) | 2 (5.6) |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.

The majority of subjects had at least one adverse event during the study. Nearly all of the adverse events were mild or moderate in intensity. Four subjects had a total of seven serious adverse events. Two subjects had four severe adverse events. One subject had severe insomnia and recovered with a reduced dose of study drug; and one subject had severe fatigue and severe rigors, and recovered without change in study drug. Adverse events experienced by at least 5% of subjects overall are reported in Table 46.

TABLE 46

| Adverse Event Preferred Term | Maximum Tolerated Dose (mg)[a] 30[b] (N = 5) n | (%) | 60[c] (N = 6) n | (%) | 90 (N = 2) n | (%) | 120 (N = 23) n | (%) | Total (N = 36) n | (%) |
|---|---|---|---|---|---|---|---|---|---|---|
| Alanine aminotransferase increased | 0 | (0.0) | 0 | (0.0) | 0 | (0.0) | 2 | (8.7) | 2 | (5.6) |
| Appetite decreased NOS[d] | 1 | (20.0) | 0 | (0.0) | 0 | (0.0) | 1 | (4.3) | 2 | (5.6) |
| Back pain | 0 | (0.0) | 0 | (0.0) | 0 | (0.0) | 2 | (8.7) | 2 | (5.6) |
| Constipation | 0 | (0.0) | 0 | (0.0) | 0 | (0.0) | 3 | (13.0) | 3 | (8.3) |
| Diarrhea NOS | 2 | (40.0) | 0 | (0.0) | 1 | (50.0) | 3 | (13.0) | 6 | (16.7) |
| Dizziness (exc. vertigo) | 1 | (20.0) | 2 | (33.3) | 1 | (50.0) | 5 | (21.7) | 9 | (25.0) |
| Dry mouth | 2 | (40.0) | 1 | (16.7) | 0 | (0.0) | 1 | (4.3) | 4 | (11.1) |
| Fatigue | 0 | (0.0) | 3 | (50.0) | 1 | (50.0) | 2 | (8.7) | 6 | (16.7) |
| Flatulence | 2 | (40.0) | 0 | (0.0) | 0 | (0.0) | 0 | (0.0) | 2 | (5.6) |
| Gamma-glutamyltransferase increased | 0 | (0.0) | 0 | (0.0) | 0 | (0.0) | 2 | (8.7) | 2 | (5.6) |
| Headache NOS | 1 | (20.0) | 3 | (50.0) | 1 | (50.0) | 4 | (17.4) | 9 | (25.0) |
| Insomnia NEC[e] | 1 | (20.0) | 0 | (0.0) | 1 | (50.0) | 1 | (4.3) | 3 | (8.3) |
| Libido decreased | 1 | (20.0) | 0 | (0.0) | 0 | (0.0) | 1 | (4.3) | 2 | (5.6) |
| Nausea | 2 | (40.0) | 2 | (33.3) | 1 | (50.0) | 5 | (21.7) | 10 | (27.8) |
| Somnolence | 2 | (40.0) | 0 | (0.0) | 1 | (50.0) | 3 | (13.0) | 6 | (16.7) |
| Syncope | 0 | (0.0) | 0 | (0.0) | 0 | (0.0) | 2 | (8.7) | 2 | (5.6) |
| Tinnitus | 0 | (0.0) | 0 | (0.0) | 1 | (50.0) | 1 | (4.3) | 2 | (5.6) |
| Upper respiratory tract infection NOS | 0 | (0.0) | 1 | (16.7) | 0 | (0.0) | 2 | (8.7) | 3 | (8.3) |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.
[d]NOS = Not otherwise specified.
[e]NEC = Not elsewhere classified.

Nausea was the most common adverse event experienced, occurring in 10 (27.8%) subjects overall. Nausea was judged to be mild in seven subjects (19.4%) and moderate in three subjects. Nausea was judged to be at least possibly related to treatment in all cases. There was no apparent relationship between the maximum tolerated dose and the occurrence, severity, or relationship of nausea to study drug. Dizziness was reported by nine subjects (25.0%) overall. Dizziness was mild in six subjects (16.7%) and moderate in three subjects (8.3%). For the majority of these subjects (seven versus two), dizziness was judged to be at least possibly related to treatment. Nine subjects (25.0%) reported headache. All instances of this adverse event were mild or moderate, and the majority (six out of nine) were judged to be possibly related to treatment. Two subjects withdrew from the study because of adverse events. One subject, with an MTD of 30 mg, withdrew after one dose of study medication because of a pre-existing colon polyp that required resection. The other subject, with an MTD of 60 mg, withdrew on Day 6 because of recurring, intermittent chest pain.

One subject had an exacerbation of Chronic Obstructive Pulmonary Disease (COPD) at the time of his final visit on Day 29, was counseled to contact his primary care physician, and was hospitalized that day. On Day 33 the subject died suddenly while still in the hospital; his primary care physician indicated myocardial infarction and arrhythmia as the presumed causes of death. The investigator indicated that this subject's COPD exacerbation was not related to study drug and that his myocardial infarction and arrhythmia were unlikely to be related to study drug.

One subject, whose MTD was 60 mg, had a history of hypertension (four years) and atypical chest pain (two years). She developed recurring, intermittent chest pain on Day 6 and was admitted to the hospital on Day 7. She discontinued study medication. All tests for cardiac causes were negative. The subject recovered on Day 8, was discharged on Day 9, and returned to work on Day 10. The underlying cause of this subject's chest pain was unclear and her chest pain was possibly related to study drug.

All of the clinical laboratory adverse events were mild or moderate in intensity. Two subjects had elevated creatine kinase values, two subjects had elevated liver enzyme values accompanied by other abnormalities, and one subject had blood in the stool. Two subjects recovered from all of their clinical laboratory adverse events, one subject did not recover, and the outcome of the adverse events was unknown for 2 subjects because they did not return to the study clinic for follow-up testing. The majority of these adverse events were judged to have a "possible" relationship to study drug. None of the clinical laboratory adverse events were serious adverse events, and none required a dosage reduction or discontinuation of study drug.

There were no clinically relevant changes from Baseline to Day 29 in systolic blood pressure, diastolic blood pressure, heart rate, or respiration at any MTD. There were no clinically relevant changes in the results of physical examinations during study treatment. There was no clinically relevant difference among the MTD groups in mean QT, $QT_c$, PR, or QRS duration, or change in any electrocardiogram values during the study.

There were no meaningful differences in motor conduction velocities in the distal peroneal nerve segment, between the fibular head and ankle, for each of the 4 MTD groups at Screening. The mean baseline motor conduction velocity was 39.2 m/sec (range of 26.6 to 49.0 m/sec). There were also no differences between the change in motor nerve conduction from Screening to the final visit for each of the MTDs. The mean change in motor conduction velocity in the fibular head-to-ankle segment for the total study population was 0.8 m/sec (range of −4.0 to +7.7 m/sec). There was a marked slowing of conduction velocity in the proximal peroneal nerve segment, between the fibular head and popliteal fossa, for the 120-mg MTD group (−6.7 m/sec) and for the total study population (−5.5 m/sec). However, this can be explained by the unusually high nerve conduction velocity measured in this segment at Screening (mean of 47.6 m/sec and range of 21.7 to 66.7 m/sec in the 120-mg MTD group). Twelve of the twenty-three subjects in this group had baseline motor conduction velocities greater than 50 m/sec; these unusually high values for this population could reflect the short distance over which this segment of the nerve was stimulated, which could have resulted in measurement errors.

Any significant slowing of nerve conduction velocity would manifest more severely in distal segments of nerve, as is seen electrophysiologically in diabetic neuropathy, because the frequency of this condition increases with length of the nerve pathway. For these reasons, the proximal conduction velocities measured in this study were interpreted as an assessment of the presence of focal peroneal neuropathy at the fibular head, and not as a measure of safety or tolerance of the study medication. In conclusion, there was no electrophysiologic evidence to suggest that the analgesic property of DM/Q is due to a toxic effect on peripheral nerves.

The combination of DM/Q, at daily doses from 30 mg DM/30 mg Q to 120 mg DM/120 mg Q, was safe and well tolerated in this subject population. The nature, frequency, and intensity of adverse events were within acceptable limits. Although five subjects had at least one laboratory adverse event, all were mild or moderate in intensity and none required a change in study drug dosing. There were no findings of clinical concern for vital signs, physical examinations, or electrocardiographic results. No clinically significant changes in nerve conduction velocity were detected. Study treatment was well tolerated; and the majority of subjects had an MTD of the highest permissible dose (120 mg DM/120 mg Q).

The frequencies of subjects with each pain intensity score at each time point are reported in Table 47.

TABLE 47

| | Pain Intensity Rating Scale Score | | | | | |
|---|---|---|---|---|---|---|
| Study Visit | 0 (None) | 1 (Mild) | 2 (Moderate) | 3 (Severe) | 4 (Extreme) | Total |
| Day 1 | 0 (0.0) | 0 (0.0) | 20 (55.6) | 15 (41.7) | 1 (2.8) | 36 (100.0) |
| Day 8 | 3 (9.1) | 14 (42.4) | 14 (42.4) | 2 (6.1) | 0 (0.0) | 33 (100.0) |
| Day 15 | 5 (15.2) | 18 (54.6) | 10 (30.3) | 0 (0.0) | 0 (0.0) | 33 (100.0) |
| Day 22 | 10 (30.3) | 15 (45.5) | 6 (18.2) | 2 (6.1) | 0 (0.0) | 33 (100.0) |
| Final Visit | 14 (40.0) | 14 (40.0) | 5 (14.3) | 2 (5.7) | 0 (0.0) | 35 (100.0) |

On Day 1 (baseline), all subjects had a pain intensity of 2 (moderate) or greater, as specified in the protocol inclusion criteria. By the final visit, only a minority of subjects (20.0%) had moderate or greater pain, and 40% reported no pain.

The changes from baseline in the Pain Intensity Rating Scale scores are reported in Table 48.

TABLE 48

| | | Maximum Tolerated Dose (mg)[a] | | | | | P-value | |
|---|---|---|---|---|---|---|---|---|
| Visit | Statistic | 30[b] (N = 5) | 60[c] (N = 6) | 90 (N = 2) | 120 (N = 23) | Total (N = 36) | Baseline and MTD[d] | Baseline[e] |
| Day 8 | n | 3 | 5 | 2 | 23 | 33 | 0.9525 | <0.0001 |
| | Mean | −1.0 | −1.0 | −0.5 | −1.1 | −1.0 | | |
| | SD | 1.00 | 1.00 | 0.71 | 0.90 | 0.88 | | |
| | Median | −1.0 | −1.0 | −0.5 | −1.0 | −1.0 | | |
| | Min/Max | −2/0 | −2/0 | −1/0 | −3/0 | −3/0 | | |
| Day 15 | n | 3 | 5 | 2 | 23 | 33 | 0.4858 | <0.0001 |
| | Mean | −0.3 | −1.8 | −0.5 | −1.4 | −1.3 | | |
| | SD | 0.58 | 0.45 | 0.71 | 0.84 | 0.85 | | |
| | Median | 0.0 | −2.0 | −0.5 | −1.0 | −1.0 | | |
| | Min/Max | −1/0 | −2/−1 | −1/0 | −3/0 | −3/0 | | |
| Day 22 | n | 3 | 5 | 2 | 23 | 33 | 0.2053 | <0.0001 |
| | Mean | −0.3 | −1.6 | −1.5 | −1.6 | −1.5 | | |
| | SD | 0.58 | 0.55 | 0.71 | 1.08 | 1.00 | | |
| | Median | 0.0 | −2.0 | −1.5 | −2.0 | −2.0 | | |
| | Min/Max | −1/0 | −2/−1 | −2/−1 | −3/1 | −3/1 | | |
| Day 29 | n | 3 | 5 | 2 | 22 | 32 | 0.1628 | <0.0001 |
| | Mean | −0.7 | −1.6 | −2.5 | −1.8 | −1.7 | | |
| | SD | 0.58 | 0.55 | 0.71 | 0.96 | 0.92 | | |
| | Median | −1.0 | −2.0 | −2.5 | −2.0 | −2.0 | | |
| | Min/Max | −1/0 | −2/−1 | −3/−2 | −3/0 | −3/0 | | |
| Final Visit | n | 4 | 6 | 2 | 23 | 35 | 0.0348 | <0.0001 |
| | Mean | −0.5 | −1.5 | −2.5 | −1.8 | −1.6 | | |
| | SD | 0.58 | 0.55 | 0.71 | 0.95 | 0.94 | | |
| | Median | −0.5 | −1.5 | −2.5 | −2.0 | −2.0 | | |
| | Min/Max | −1/0 | −2/−1 | −3/−2 | −3/0 | −3/0 | | |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.
[d]P-value for MTD from a regression model that models the efficacy variable as a function of both baseline score and MTD.
[e]P-value for mean change in score from a regression model that models the efficacy variable as a function of baseline score.

Mean scores on the Pain Intensity Rating Scale decreased between baseline and each subsequent visit for subjects overall. This decrease was highly significant (all p-values <0.0001). For the change from baseline to the final visit, the score decreases were significantly related to MTD (p=0.0348), but there was no significant effect of MTD on scores for any of the other visits (all p-values ≧0.1628).

Frequencies of subjects with each pain relief score at each study visit are reported in Table 49.

TABLE 49

| | Pain Relief | | | | | | |
|---|---|---|---|---|---|---|---|
| Study Visit | −1 (Worse) | 0 (None) | 1 (Slight) | 2 (Moderate) | 3 (A Lot) | 4 (Complete) | Total |
| Day 8 | 0 (0.0) | 3 (9.1) | 6 (18.2) | 13 (39.4) | 8 (24.2) | 3 (9.1) | 33 (100.0) |
| Day 15 | 0 (0.0) | 1 (3.0) | 5 (15.2) | 6 (18.2) | 18 (54.6) | 3 (9.1) | 33 (100.0) |
| Day 22 | 0 (0.0) | 1 (3.0) | 5 (15.2) | 4 (12.1) | 17 (51.5) | 6 (18.2) | 33 (100.0) |
| Final Visit | 0 (0.0) | 1 (2.9) | 6 (17.7) | 5 (14.7) | 13 (38.2) | 9 (26.5) | 34 (100.0) |

In general, pain relief scores increased during the study. At Day 8, only 33.3% of subjects reported "a lot" or "complete" pain relief; by the final visit, the majority (64.7%) did so. No subject reported "worse" pain compared to baseline at any visit, and only 1 subject reported "None" at any visit after Day 8.

Summary statistics for Pain Relief Scale scores are reported in Table 50.

TABLE 50

| | | Maximum Tolerated Dose (mg)[a] | | | | | P-value | |
|---|---|---|---|---|---|---|---|---|
| Visit | Statistic | 30[b] (N = 5) | 60[c] (N = 6) | 90 (N = 2) | 120 (N = 23) | Total (N = 36) | MTD[d] | Difference from 0[e] |
| Day 8 | n | 3 | 5 | 2 | 23 | 33 | 0.4880 | <0.0001 |
| | Mean | 2.7 | 2.0 | 2.0 | 2.0 | 2.1 | | |
| | SD | 0.58 | 1.58 | 0.00 | 1.09 | 1.09 | | |
| | Median | 3.0 | 2.0 | 2.0 | 2.0 | 2.0 | | |
| | Min/Max | 2/3 | 0/4 | 2/2 | 0/4 | 0/4 | | |
| Day 15 | n | 3 | 5 | 2 | 23 | 33 | 0.7953 | <0.0001 |
| | Mean | 2.0 | 2.8 | 2.5 | 2.5 | 2.5 | | |
| | SD | 1.00 | 1.10 | 0.71 | 0.99 | 0.97 | | |
| | Median | 2.0 | 3.0 | 2.5 | 3.0 | 3.0 | | |
| | Min/Max | 1/3 | 1/4 | 2/3 | 0/4 | 0/4 | | |
| Day 22 | n | 3 | 5 | 2 | 23 | 33 | 0.6110 | <0.0001 |
| | Mean | 2.3 | 2.6 | 3.0 | 2.7 | 2.7 | | |
| | SD | 0.58 | 1.14 | 0.00 | 1.15 | 1.05 | | |
| | Median | 2.0 | 3.0 | 3.0 | 3.0 | 3.0 | | |
| | Min/Max | 2/3 | 1/4 | 3/3 | 0/4 | 0/4 | | |
| Day 29 | n | 3 | 5 | 2 | 22 | 32 | 0.6263 | <0.0001 |
| | Mean | 2.3 | 2.6 | 3.5 | 2.7 | 2.7 | | |
| | SD | 1.15 | 1.14 | 0.71 | 1.20 | 1.14 | | |
| | Median | 3.0 | 3.0 | 3.5 | 3.0 | 3.0 | | |
| | Min/Max | 1/3 | 1/4 | 3/4 | 0/4 | 0/4 | | |
| Final Visit | n | 3 | 6 | 2 | 23 | 34 | 0.7958 | <0.0001 |
| | Mean | 2.3 | 2.7 | 3.5 | 2.7 | 2.7 | | |
| | SD | 1.15 | 1.03 | 0.71 | 1.23 | 1.15 | | |
| | Median | 3.0 | 3.0 | 3.5 | 3.0 | 3.0 | | |
| | Min/Max | 1/3 | 1/4 | 3/4 | 0/4 | 0/4 | | |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.
[d]P-value for MTD from a regression model that models the efficacy variable as a function of MTD.
[e]P-value from a t-test testing that the mean of the total column is significantly different from 0.

Mean scores on the Pain Relief Rating Scale increased significantly from the first assessment on Day 8 to each subsequent visit for subjects overall (all p-values <0.0001). There was no significant effect of MTD on pain relief scores at any visit (all p-values ≧0.4880).

The change from baseline in the composite score from the Peripheral Neuropathy QOL Instrument is reported in Table 51.

TABLE 51

| | | Maximum Tolerated Dose (mg)[a] | | | | | P-value | |
|---|---|---|---|---|---|---|---|---|
| Visit/ Variable | Statistic | 30[b] (N = 5) | 60[c] (N = 6) | 90 (N = 2) | 120 (N = 23) | Total (N = 36) | Baseline and MTD[d] | Baseline[e] |
| Day 1 (Baseline)/ Score | n | 4 | 6 | 2 | 23 | 35 | N/A[f] | N/A |
| | Mean | 61.3 | 69.7 | 72.8 | 63.7 | 65.0 | | |
| | SD | 15.26 | 13.68 | 0.18 | 13.48 | 13.26 | | |
| | Median | 60.8 | 66.8 | 72.8 | 65.3 | 66.7 | | |
| | Min/Max | 47.1/76.4 | 49.8/86.9 | 72.7/72.9 | 35.6/87.2 | 35.6/87.2 | | |
| Day 29/ Score | n | 3 | 5 | 2 | 22 | 32 | N/A | N/A |
| | Mean | 68.3 | 75.7 | 79.0 | 75.5 | 75.0 | | |
| | SD | 13.38 | 15.88 | 4.68 | 9.93 | 10.82 | | |
| | Median | 66.3 | 79.9 | 79.0 | 75.4 | 76.5 | | |
| | Min/Max | 56.0/82.6 | 49.1/91.8 | 75.7/82.3 | 51.4/88.5 | 49.1/91.8 | | |
| Day 29/ Change from Baseline | n | 3 | 5 | 2 | 22 | 32 | 0.1397 | <0.0001 |
| | Mean | 2.4 | 8.8 | 6.2 | 12.1 | 10.3 | | |
| | SD | 10.87 | 13.35 | 4.85 | 10.77 | 10.95 | | |
| | Median | 6.9 | 10.7 | 6.2 | 12.8 | 10.4 | | |
| | Min/Max | −10.1/10.2 | −6.8/27.7 | 2.7/9.6 | −10.2/34.5 | −10.2/34.5 | | |

TABLE 51-continued

| Visit/ Variable | Statistic | Maximum Tolerated Dose (mg)[a] 30[b] (N = 5) | 60[c] (N = 6) | 90 (N = 2) | 120 (N = 23) | Total (N = 36) | P-value Baseline and MTD[d] | Baseline[e] |
|---|---|---|---|---|---|---|---|---|
| Final Visit/ Score | n | 3 | 6 | 2 | 23 | 34 | N/A | N/A |
| | Mean | 68.3 | 77.6 | 79.0 | 75.4 | 75.4 | | |
| | SD | 13.38 | 14.99 | 4.68 | 9.71 | 10.71 | | |
| | Median | 66.3 | 80.0 | 79.0 | 75.1 | 76.5 | | |
| | Min/Max | 56.0/82.6 | 49.1/91.8 | 75.7/82.3 | 51.4/88.5 | 49.1/91.8 | | |
| Final Visit/ Change from Baseline | n | 3 | 6 | 2 | 23 | 34 | 0.1828 | <0.0001 |
| | Mean | 2.4 | 7.9 | 6.2 | 11.6 | 9.8 | | |
| | SD | 10.87 | 12.11 | 4.85 | 10.76 | 10.78 | | |
| | Median | 6.9 | 7.2 | 6.2 | 12.7 | 9.9 | | |
| | Min/Max | −10.1/10.2 | −6.8/27.7 | 2.7/9.6 | −10.2/34.5 | −10.2/34.5 | | |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.
[d]P-value for MTD from a regression model that models the efficacy variable as a function of both baseline score and MTD.
[e]P-value for mean change in score from a regression model that models the efficacy variable as a function of baseline score.
[f]N/A = Not applicable.

Mean composite scores on the Peripheral Neuropathy QOL Instrument increased (i.e., improved) significantly from Day 1 (baseline) to Day 29 and to the final visit for subjects overall (both p-values <0.0001). Change from baseline to either Day 29 or the final visit was not related to MTD (all p-values ≧0.1837).

P-values for change from baseline to the final visit in individual QOL scales are reported in Table 52.

TABLE 52

| Scale | P-value |
|---|---|
| Physical Functioning | 0.0012 |
| Role Limitations | 0.0003 |
| Disease-Targeted Pain | <0.0001 |
| Energy/Fatigue | 0.0001 |
| Upper Extremities | 0.0007 |
| Balance | 0.0001 |
| Self Esteem | 0.1258 |
| Emotional Well Being | 0.0277 |
| Stigma | 0.7851 |

TABLE 52-continued

| Scale | P-value |
|---|---|
| Cognitive Function | 0.0313 |
| Emotional Role Limitations | 0.2956 |
| General Health Perceptions | <0.0001 |
| Sleep | <0.0001 |
| Social Functioning | <0.0001 |
| Sexual Function | 0.7714 |
| Health Distress | <0.0001 |
| Severity | 0.0129 |
| Disability Days | 0.1096 |
| Health Change | 0.0001 |
| Overall Health Rating | 0.0064 |
| Satisfaction with Sexual Functioning | 0.3413 |

[a]P-value for the change from baseline. A regression model was used to test whether the mean baseline value was different from the mean value at the final visit.

The majority of individual QOL scale items improved significantly between baseline and the final visit (15/21, 74.1%).

Sleep interference scores, calculated for Day 15, Day 29, and the final visit, are reported in Table 53.

TABLE 53

| Visit | Statistic | Maximum Tolerated Dose (mg)[b] 30[c] (N = 5) | 60[d] (N = 6) | 90 (N = 2) | 120 (N = 23) | Total (N = 36) | P-value MTD[e] |
|---|---|---|---|---|---|---|---|
| Day 15 | n | 3 | 5 | 2 | 23 | 33 | 0.8509 |
| | Mean | 1.4 | 2.2 | 2.2 | 1.8 | 1.8 | |
| | SD | 1.35 | 1.66 | 0.71 | 1.64 | 1.54 | |
| | Median | 1.7 | 2.0 | 2.2 | 1.3 | 1.7 | |
| | Min/Max | 0/3 | 0/4 | 2/3 | 0/5 | 0/5 | |
| Day 29 | n | 3 | 5 | 2 | 22 | 32 | 0.1405 |
| | Mean | 1.6 | 2.5 | 0.2 | 1.2 | 1.4 | |
| | SD | 1.35 | 2.09 | 0.24 | 1.29 | 1.47 | |
| | Median | 1.3 | 2.0 | 0.2 | 0.7 | 0.8 | |
| | Min/Max | 0/3 | 0/5 | 0/0 | 0/4 | 0/5 | |
| Final Visit | n | 3 | 5 | 2 | 23 | 33 | 0.1077 |
| | Mean | 1.6 | 2.5 | 0.2 | 1.1 | 1.3 | |
| | SD | 1.35 | 2.09 | 0.24 | 1.20 | 1.41 | |

TABLE 53-continued

| Visit | Statistic | Maximum Tolerated Dose (mg)[b] 30[c] (N = 5) | 60[d] (N = 6) | 90 (N = 2) | 120 (N = 23) | Total (N = 36) | P-value MTD[e] |
|---|---|---|---|---|---|---|---|
| | Median | 1.3 | 2.0 | 0.2 | 0.7 | 1.0 | |
| | Min/Max | 0/3 | 0/5 | 0/0 | 0/4 | 0/5 | |

[a]The score for Day 15 is the average of the Sleep Rating Scale scores from the subject diary for Days 13, 14, and 15; the score for Day 29 is the average of the Day 27, 28, and 29 scores; and the Final Visit score is the average of the final 3 consecutive days of study treatment.
[b]Maximum Tolerated Dose is the last dose taken when the subject left or completed the study.
[c]This group included subjects who took two 15-mg capsules/day as well as subjects who took one 30-mg capsule/day.
[d]This group included one subject whose MTD was 45 mg.
[e]P-value for MTD from a regression model that models the efficacy variable as a function of MTD.

Figure 4:
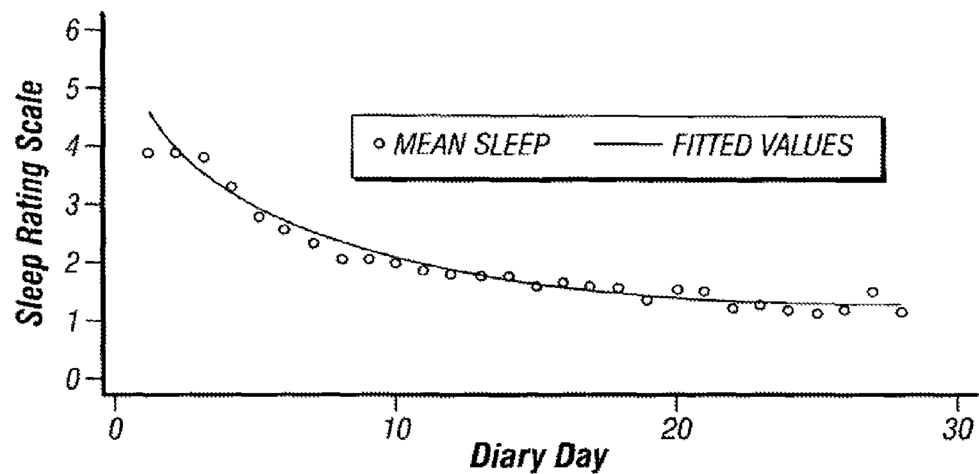
FIG. 4 depicts Mean Sleep Ratings from the Subject Diaries of subjects participating in Clinical Study #5.

Mean sleep interference scores declined during the study, indicating decreasing interference of the subjects' pain with their sleep. There was no significant effect of MTD on sleep interference scores at any visit (all p values ≧0.1077). Results from the Sleep Rating Scale are plotted by study day in FIG. 4. Sleep scores decreased significantly (regression p<0.001) from Day 2 to the final study day (the lower the score, the less pain was judged to interfere with sleep).

Figure 5:
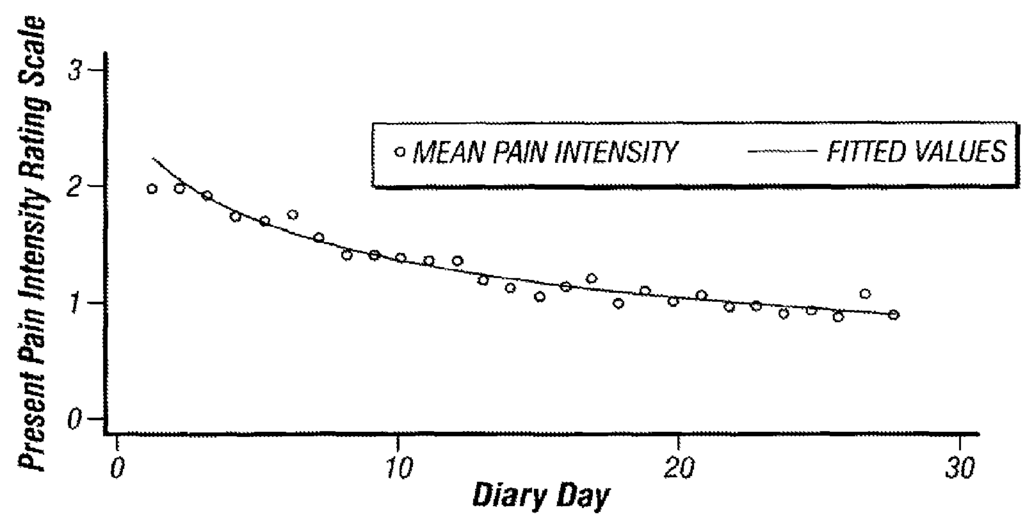
FIG. 5. Mean Present Pain Intensity Ratings from the Subject Diaries of subjects participating in Clinical Study #5.
Figure 6:
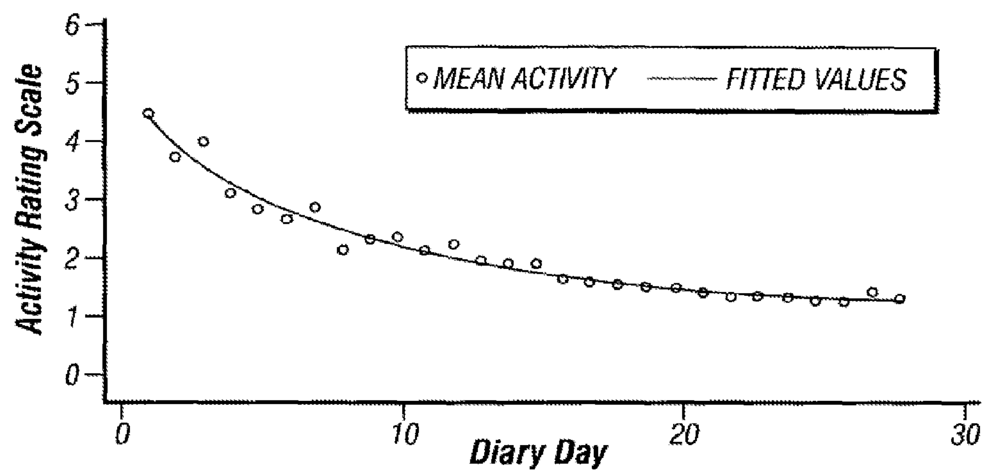
FIG. 6. Mean Activity Ratings from the Subject Diaries of subjects participating in Clinical Study #5.
Figure 7:
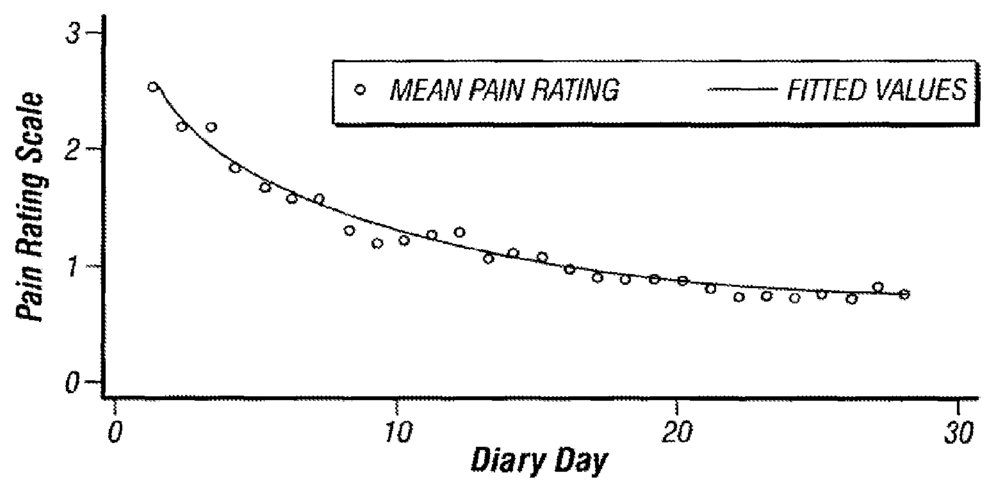
FIG. 7. Mean Pain Ratings from the Subject Diaries of subjects participating in Clinical Study #5.

Results from the Present Pain Intensity Rating Scale are plotted by study day in FIG. 5. Present Pain Intensity scores decreased significantly (regression p<0.001) from Day 2 to the final study day. Results from the Activity Rating Scale are plotted by study day in FIG. 6. Activity scores decreased significantly (regression p<0.001) from Day 1 to the final study day (the lower the score, the less pain was judged to interfere with general activity). Results from the Pain Rating Scale are plotted by study day in FIG. 7. Scores for average pain over the previous twelve hours decreased significantly (regression p<0.001) from Day 1 to the final study day.

An improvement in efficacy score was defined as an improvement from the first recorded value to the last recorded value, except for the Pain Relief Rating Scale, where an improvement was defined as a value >0 for the last recorded value. The frequencies of subjects whose score improved during the study are presented for each efficacy measure in Table 54.

TABLE 54

| Efficacy Variable | Maximum Tolerated Dose (mg)[b] 30[c] (N = 5) n (%) | 60[d] (N = 6) n (%) | 90 (N = 2) n (%) | 120 (N = 23) n (%) | Total (N = 36) n (%) | P-value MTD[e] | P-value 50%[f] |
|---|---|---|---|---|---|---|---|
| Pain Intensity Rating Scale | 2 (50.0) | 6 (100.0) | 2 (100.0) | 21 (91.3) | 31 (88.6) | 0.1698 | <0.0001 |
| Pain Relief Rating Scale | 3 (100.0) | 5 (100.0) | 2 (100.0) | 22 (95.7) | 32 (97.0) | 0.9419 | <0.0001 |
| QOL Composite Score | 2 (66.7) | 5 (83.3) | 2 (100.0) | 19 (82.6) | 28 (82.4) | 0.6877 | 0.0002 |
| Sleep Rating Scale (Diary) | 3 (100.0) | 5 (83.3) | 2 (100.0) | 20 (87.0) | 30 (88.2) | 0.7222 | <0.0001 |
| Present Pain Intensity Rating Scale (Diary) | 2 (66.7) | 3 (50.0) | 2 (100.0) | 16 (69.6) | 23 (67.6) | 0.5877 | 0.0396 |
| Activity Rating Scale (Diary) | 2 (50.0) | 5 (83.3) | 2 (100.0) | 20 (87.0) | 29 (82.9) | 0.1668 | 0.0001 |
| Pain Rating Scale (Diary) | 3 (75.0) | 5 (83.3) | 2 (100.0) | 20 (87.0) | 30 (85.7) | 0.5772 | <0.0001 |

[a]An improvement in efficacy score is an improvement from the first recorded value to the last recorded value, except for the Pain Relief Rating Scale, where an improvement is a value >0 for the last recorded value.
[b]Maximum Tolerated Dose is the last dose taken when the subject left or completed the study.
[c]This group included subjects who took two 15-mg capsules/day as well as subjects who took one 30-mg capsule/day.
[d]This group included one subject whose MTD was 45 mg.
[e]P-value for MTD from a regression model that models improvement in the efficacy variable as a function of MTD.
[f]P-value from a test that the total percent of subjects whose score improved = 50%.

A significant proportion of subjects improved during the study in every efficacy measure (all p-values ≦0.0396). Improvement was not related to MTD for any of the efficacy measures (all p-values ≧0.1668).

Subjects treated with open-label DM/Q, in the dose range of 30 mg DM/30 mg Q to 120 mg DM/120 mg Q, reported a statistically significant reduction in pain from diabetic peripheral neuropathy and in the extent to which this pain interfered with general activity and sleep. Subjects receiving this treatment also experienced statistically significant improvement in their QOL.

The CYP2D6 phenotypes of subjects, based upon their genotype results, are summarized in Table 55. There were no intermediate or ultra-rapid metabolizers in this study population.

TABLE 55

| | Maximum Tolerated Dose (mg)[a] | | | | |
|---|---|---|---|---|---|
| Phenotype | 30[b] (N = 5) n (%) | 60[c] (N = 6) n (%) | 90 (N = 2) n (%) | 120 (N = 23) n (%) | Total (N = 36) n (%) |
| Extensive Metabolizer | 5 (100.0) | 5 (83.3) | 2 (100.0) | 23 (100.0) | 35 (97.2) |
| Poor Metabolizer | 0 (0.0) | 1 (16.7) | 0 (0.0) | 0 (0.0) | 1 (2.8) |

[a]Maximum Tolerated Dose is the last dose taken when the subject left or completed the study.
[b]This group included subjects who took two 15-mg capsules/day as well as subjects who took one 30-mg capsule/day.
[c]This group included one subject whose MTD was 45 mg.

All except one subject were extensive metabolizers. Concentrations in plasma of DM increased between the visit on Day 15 and the final visit for the 90-mg and 120-mg MTDs. A similar increase in concentration was seen for the metabolite DX and for Q. Concentrations of DM, DX, and Q in plasma of extensive metabolizers at the final visit are summarized by MTD in Table 56.

TABLE 56

| Drug or Metabolite (ng/mL) | Statistic | MTD[b] (mg) 30[c] N = 5 | 60[d] N = 5 | 90 N = 2 | 120 N = 23 | Total N = 35 |
|---|---|---|---|---|---|---|
| DM | n | 3 | 5 | 2 | 23 | 33 |
| | Mean | 59.0 | 46.2 | 117.0 | 192.6 | 153.7 |
| | SD | 30.28 | 67.38 | 44.47 | 98.93 | 106.01 |
| | Median | 67.4 | 1.5 | 117.0 | 178.0 | 144.5 |
| | Min/Max | 25.4/84.2 | 0.0/150.2 | 85.5/148.4 | 48.7/388.5 | 0.0/388.5 |
| DX | n | 3 | 5 | 2 | 23 | 33 |
| | Mean | 70.7 | 65.4 | 88.4 | 146.6 | 123.9 |
| | SD | 48.49 | 67.38 | 34.83 | 96.88 | 91.94 |
| | Median | 94.6 | 58.2 | 88.4 | 122.6 | 102.6 |
| | Min/Max | 14.9/102.6 | 0.0/135.6 | 63.8/113.0 | 53.2/417.9 | 0.0/417.9 |
| Q | n | 3 | 5 | 2 | 23 | 33 |
| | Mean | 114.0 | 41.8 | 114.5 | 269.0 | 211.1 |
| | SD | 48.75 | 66.72 | 70.00 | 176.88 | 175.28 |
| | Median | 137.0 | 0.0 | 114.5 | 211.0 | 164.0 |
| | Min/Max | 58/147 | 0/153 | 65/164 | 74/681 | 0/681 |

[a]One of the thirty-six subjects was a poor metabolizer.
[b]Maximum Tolerated Dose is the last dose taken when the subject left or completed the study.
[c]This group included subjects who took two 15-mg capsules/day as well as subjects who took one 30-mg capsule/day.
[d]This group included one subject whose MTD was 45 mg.

For comparison, the poor metabolizer (MTD of 60 mg) had the following concentrations in plasma at the final visit: DM 126.4 ng/mL, DX 41.0 ng/mL, and Q 165.0 ng/mL. Correlations between the concentration of DM in plasma with pain intensity ratings on Day 15, Day 29, and the final visit are summarized in Table 57 (extensive metabolizers only).

TABLE 57

| Visit | n[b] | Correlation Coefficient | P-value |
|---|---|---|---|
| Day 15 | 33 | −0.3479 | 0.0473 |
| Day 29 | 30 | −0.1336 | 0.4817 |
| Final Visit | 33 | −0.1487 | 0.4088 |

[a]One of the thirty-six subjects was a poor metabolizer.
[b]Data were not available for all subjects.

There was a weak, negative correlation between concentration of DM in plasma and rating of pain intensity at Day 15 (coefficient of −0.3572) and negligible correlations at the other time points (≦−0.1487). The Day 15 correlation was statistically significant (p=0.0473), but the correlations at Day 29 and the final visit were not (p≧0.4088). However, a weak or nonexistent correlation between concentrations of drug in plasma and pain ratings is a typical result in pharmacodynamic studies of analgesics.

The safety results demonstrate that the combination of DM/Q, in the dose range from 30 mg DM/30 mg Q to 120 mg DM/120 mg Q, is safe and well tolerated in the treatment of subjects with pain associated with diabetic peripheral neuropathy, and provide indications of efficacy in pain reduction.

The preferred embodiments have been described in connection with specific embodiments thereof. It will be understood that it is capable of further modification, and this application is intended to cover any variations, uses, or adaptations of the invention following, in general, the principles of the invention and including such departures from the present disclosure as come within known or customary practices in the art to which the invention pertains and as may be applied to the essential features hereinbefore set forth, and as fall within the scope of the invention and any equivalents thereof. All references cited herein, including but not limited to technical literature references and patents, are hereby incorporated herein by reference in their entireties.

What is claimed is:

1. A method for treating pseudobulbar affect or emotional lability, the method comprising administering to a patient in need thereof dextromethorphan in combination with quinidine, wherein the amount of dextromethorphan administered comprises from about 20 mg/day to about 60 mg/day and wherein the amount of quinidine administered comprises from about 10 mg/day to about 30 mg/day with the proviso that the weight-to-weight ratio of dextromethorphan to quinidine is 1:0.75 or less of quinidine.

2. The method of claim 1, wherein the pseudobulbar affect or emotional lability is caused by a neurodegenerative disease or condition or a brain injury.

3. The method of claim 1, wherein the dextromethorphan and the quinidine are administered as one combined dose per day.

4. The method of claim 1, wherein the dextromethorphan and the quinidine are administered as at least two combined doses per day.

5. The method of claim 1, wherein the amount of quinidine administered comprises from about 20 mg/day to 30 mg/day.

6. The method of claim 1, wherein the amount of dextromethorphan administered comprises from about 40 mg/day to 60 mg/day.

7. The method of claim 1, wherein at least one of the quinidine and the dextromethorphan is in a form of a pharmaceutically acceptable salt.

8. The method of claim 1, wherein at least one of the quinidine and the dextromethorphan is in a form of a pharmaceutically acceptable salt selected from the group consisting of salts of free acids, inorganic salts, salts of sulfate, salts of hydrochloride, and salts of hydrobromide.

9. The method of claim 1, wherein about 20 mg quinidine sulfate is administered per day.

10. The method of claim 1, wherein about 60 mg dextromethorphan hydrobromide is administered per day.

11. The method of claim 1, wherein the dextromethorphan and quinidine are administered in separate doses.

12. The method of claim 1, wherein the weight-to-weight ratio of dextromethorphan to quinidine is 1:0.65 or less of quinidine.

13. The method of claim 1, wherein about 40 mg dextromethorphan hydrobromide is administered per day.

14. The method of claim 1, wherein about 60 mg of dextromethorphan and about 20 mg of quinidine is administered per day.

15. The method of claim 1, wherein about 40 mg of dextromethorphan and about 20 mg of quinidine is administered per day.

16. The method of claim 1, wherein about 60 mg of dextromethorphan hydrobromide and about 20 mg of quinidine sulfate is administered per day.

17. The method of claim 1, wherein about 40 mg of dextromethorphan hydrobromide and about 20 mg of quinidine sulfate is administered per day.

* * * * *